(12) United States Patent
Sayger et al.

(10) Patent No.: US 11,304,735 B2
(45) Date of Patent: Apr. 19, 2022

(54) SYSTEMS AND METHODS FOR LAPIDUS REPAIR OF BUNIONS

(71) Applicant: CrossRoads Extremity Systems, LLC, Memphis, TN (US)

(72) Inventors: Daniel Sayger, Southaven, MS (US); Michael Chad Hollis, Collierville, TN (US); Craig Squires, Cordova, TN (US)

(73) Assignee: CrossRoads Extremity Systems, LLC, Memphis, TN (US)

( * ) Notice: Subject to any disclaimer, the term of this patent is extended or adjusted under 35 U.S.C. 154(b) by 0 days.

(21) Appl. No.: 17/178,109

(22) Filed: Feb. 17, 2021

(65) Prior Publication Data

US 2021/0251670 A1 Aug. 19, 2021

Related U.S. Application Data

(60) Provisional application No. 63/125,272, filed on Dec. 14, 2020, provisional application No. 63/018,793, (Continued)

(51) Int. Cl.
*A61B 17/72* (2006.01)

(52) U.S. Cl.
CPC ...... *A61B 17/7291* (2013.01); *A61B 17/7225* (2013.01); *A61B 17/7283* (2013.01)

(58) Field of Classification Search
CPC ............ A61B 17/7291; A61B 17/7225; A61B 17/7283; A61B 17/56
See application file for complete search history.

(56) References Cited

U.S. PATENT DOCUMENTS

| 4,069,824 A | 1/1978 | Weinstock |
| 4,335,715 A | 6/1982 | Kirkley |

(Continued)

FOREIGN PATENT DOCUMENTS

| EP | 0 570 187 B1 | 7/1996 |
| WO | WO 00/006036 | 2/2000 |

(Continued)

OTHER PUBLICATIONS

Arthrex Hallux Valgus Solutions, Arthrex, Inc., www.arthrex.com 2009, 2 pp.

(Continued)

*Primary Examiner* — Ellen C Hammond
(74) *Attorney, Agent, or Firm* — Knobbe, Martens, Olson & Bear, LLP

(57) ABSTRACT

Systems, devices, and methods for performing Lapidus bunionectomy procedures are disclosed. An example method includes inserting a plurality of metatarsal pins into the first metatarsal at a first predetermined spacing relative to the first tarsometatarsal (TMT) joint, excising the first TMT joint by cutting the bases of the first metatarsal and the first cuneiform proximate the first TMT joint, inserting a plurality of cuneiform pins into the first cuneiform at a second predetermined spacing relative to the first TMT joint, compressing the first TMT joint using a compressor block such that a cut face of the first metatarsal contacts a cut face of the first cuneiform, and fixing the first TMT joint using a bone plate and a plurality of bone screws. At least one of the plurality of bone screws may be a cross screw extending at an angle of less than 90 degrees relative to the bone plate and may anchor the resected first TMT joint to the second metatarsal or the second cuneiform to prevent recurrence of the bunion.

29 Claims, 62 Drawing Sheets

Related U.S. Application Data filed on May 1, 2020, provisional application No. 62/978,683, filed on Feb. 19, 2020.

(56) References Cited

U.S. PATENT DOCUMENTS

| | | |
|---|---|---|
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,627,425 A | 12/1986 | Reese |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,757,810 A | 7/1988 | Reese |
| 4,852,558 A | 8/1989 | Outerbridge |
| 4,913,144 A | 4/1990 | Del Medico |
| 4,952,214 A | 8/1990 | Comparetto |
| 4,959,066 A | 9/1990 | Dunn et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,246,444 A | 9/1993 | Schreiber |
| 5,413,579 A | 5/1995 | Tom Du Toit |
| 5,449,360 A | 9/1995 | Schreiber |
| 5,470,335 A | 11/1995 | Du Toit |
| 5,540,695 A | 7/1996 | Levy |
| 5,578,038 A | 11/1996 | Slocum |
| 5,601,565 A | 2/1997 | Huebner |
| 5,613,969 A | 3/1997 | Jenkins, Jr. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins, Jr. |
| 5,749,875 A | 5/1998 | Paddu |
| 5,779,709 A | 7/1998 | Harris, Jr. et al. |
| 5,843,085 A | 12/1998 | Graser |
| 5,911,724 A | 6/1999 | Wehrli |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A | 2/2000 | Brainard et al. |
| 6,203,545 B1 | 3/2001 | Stoffella |
| 6,248,109 B1 | 6/2001 | Stoffella |
| 6,391,031 B1 | 5/2002 | Toomey |
| 6,547,793 B1 | 4/2003 | McGuire |
| 6,676,662 B1 | 1/2004 | Bagga et al. |
| 6,755,838 B2 | 6/2004 | Trnka |
| 6,796,986 B2 | 9/2004 | Duffner |
| 7,018,383 B2 | 3/2006 | McGuire |
| 7,112,204 B2 | 9/2006 | Justin et al. |
| 7,182,766 B1 | 2/2007 | Mogul |
| 7,540,874 B2 | 6/2009 | Trumble et al. |
| 7,572,258 B2 | 8/2009 | Stiernborg |
| 7,691,108 B2 | 4/2010 | Lavallee |
| 7,763,026 B2 | 7/2010 | Egger |
| 7,967,823 B2 | 6/2011 | Novak et al. |
| 7,972,338 B2 | 7/2011 | O'Brien |
| 8,062,301 B2 | 11/2011 | Ammann et al. |
| 8,083,746 B2 | 12/2011 | Novak |
| 8,137,406 B2 | 3/2012 | Novak et al. |
| 8,236,000 B2 | 8/2012 | Novak et al. |
| 8,262,664 B2 | 9/2012 | Justin |
| 8,277,459 B2 | 10/2012 | Sand et al. |
| 8,282,645 B2 | 10/2012 | Lawrence et al. |
| 8,313,492 B2 | 11/2012 | Wong |
| 8,409,209 B2 | 4/2013 | Ammann et al. |
| 8,496,662 B2 | 7/2013 | Novak et al. |
| 8,529,571 B2 | 9/2013 | Horan et al. |
| 8,540,777 B2 | 9/2013 | Ammann et al. |
| 8,545,508 B2 | 10/2013 | Collazo |
| D695,402 S | 12/2013 | Dacosta et al. |
| 8,652,142 B2 | 2/2014 | Geissler |
| 8,657,820 B2 | 2/2014 | Kubiak et al. |
| 8,702,715 B2 | 4/2014 | Ammann et al. |
| 8,771,279 B2 | 7/2014 | Philippon et al. |
| 8,777,948 B2 | 7/2014 | Bernsteiner |
| 8,888,785 B2 | 11/2014 | Ammann |
| 8,900,247 B2 | 12/2014 | Tseng et al. |
| 8,906,026 B2 | 12/2014 | Ammann et al. |
| 9,060,822 B2 * | 6/2015 | Lewis ............... A61B 17/8061 |
| 9,113,920 B2 | 8/2015 | Ammann |
| 9,622,805 B2 | 4/2017 | Santrock |
| 9,687,250 B2 | 6/2017 | Dayton et al. |
| 9,814,474 B2 | 11/2017 | Montoya |
| 9,907,558 B2 | 3/2018 | Fallin et al. |
| 9,936,994 B2 | 4/2018 | Smith et al. |
| 10,045,807 B2 | 8/2018 | Santrock et al. |
| 10,245,086 B2 | 4/2019 | Treace et al. |
| 10,245,088 B2 | 4/2019 | Dayton et al. |
| 10,292,713 B2 | 5/2019 | Fallin et al. |
| 10,335,220 B2 | 7/2019 | Smith et al. |
| 10,342,590 B2 | 7/2019 | Bays et al. |
| 10,376,268 B2 | 8/2019 | Fallin et al. |
| 10,470,779 B2 | 11/2019 | Fallin et al. |
| 10,512,470 B1 | 12/2019 | Bays et al. |
| 10,555,757 B2 | 2/2020 | Dayton |
| 10,561,426 B1 | 2/2020 | Dayton et al. |
| 10,575,862 B2 | 3/2020 | Bays et al. |
| 10,743,995 B2 | 8/2020 | Fallin et al. |
| 10,898,211 B2 | 1/2021 | Fallin et al. |
| 11,058,546 B2 | 7/2021 | Hollis et al. |
| 11,116,558 B2 | 9/2021 | Smith et al. |
| 11,147,590 B2 | 10/2021 | Dayton |
| 11,160,567 B2 | 11/2021 | Fallin et al. |
| 2002/0165552 A1 | 11/2002 | Duffner |
| 2004/0097946 A1 | 5/2004 | Dietzel |
| 2004/0138669 A1 | 7/2004 | Horn |
| 2005/0070909 A1 | 3/2005 | Egger |
| 2005/0149042 A1 | 7/2005 | Metzger |
| 2005/0228389 A1 | 10/2005 | Steirnborg |
| 2005/0251147 A1 | 11/2005 | Novak |
| 2005/0273112 A1 | 12/2005 | McNamara |
| 2006/0129163 A1 | 6/2006 | McGuire |
| 2006/0264961 A1 | 11/2006 | Murray |
| 2007/0010818 A1 | 1/2007 | Stone |
| 2007/0265634 A1 | 11/2007 | Weinstein |
| 2007/0276383 A1 | 11/2007 | Rayhack |
| 2008/0015603 A1 | 1/2008 | Collazo |
| 2008/0039850 A1 | 2/2008 | Rowley |
| 2008/0147073 A1 | 6/2008 | Ammann |
| 2008/0195215 A1 | 8/2008 | Morton |
| 2008/0269908 A1 | 10/2008 | Warburton |
| 2009/0036931 A1 | 2/2009 | Pech |
| 2009/0054899 A1 | 2/2009 | Ammann |
| 2009/0210010 A1 | 8/2009 | Strnad et al. |
| 2009/0222047 A1 | 9/2009 | Graham |
| 2010/0125300 A1 * | 5/2010 | Blitz ............... A61B 17/8061 606/281 |
| 2010/0130981 A1 | 5/2010 | Richards |
| 2010/0152782 A1 | 6/2010 | Stone et al. |
| 2011/0178524 A1 | 7/2011 | Lawrence |
| 2011/0188550 A1 | 8/2011 | Orbay |
| 2011/0213376 A1 | 9/2011 | Maxson et al. |
| 2011/0224734 A1 | 9/2011 | Schelling |
| 2012/0016426 A1 | 1/2012 | Robinson |
| 2012/0185056 A1 | 7/2012 | Warburton |
| 2012/0191199 A1 | 7/2012 | Raemisch |
| 2012/0303033 A1 | 11/2012 | Weiner et al. |
| 2013/0012949 A1 | 1/2013 | Fallin |
| 2013/0090662 A1 | 4/2013 | Hanson et al. |
| 2013/0172942 A1 * | 7/2013 | Lewis ............... A61B 17/8061 606/281 |

(56) References Cited

U.S. PATENT DOCUMENTS

| | | |
|---|---|---|
| 2013/0226248 A1 | 8/2013 | Hatch |
| 2013/0226252 A1 | 8/2013 | Mayer |
| 2013/0331845 A1 | 12/2013 | Horan |
| 2014/0188139 A1 | 7/2014 | Fallin |
| 2014/0194999 A1 | 7/2014 | Orbay |
| 2014/0343555 A1 | 11/2014 | Russi |
| 2015/0057667 A1 | 2/2015 | Ammann |
| 2015/0245858 A1 | 9/2015 | Ammann |
| 2016/0015426 A1 | 1/2016 | Dayton |
| 2016/0192950 A1 | 7/2016 | Dayton et al. |
| 2016/0192970 A1 | 7/2016 | Dayton et al. |
| 2016/0213384 A1* | 7/2016 | Fallin ............... A61B 17/151 |
| 2016/0235414 A1 | 8/2016 | Hatch et al. |
| 2016/0324532 A1 | 11/2016 | Montoya et al. |
| 2016/0324555 A1 | 11/2016 | Brumfield et al. |
| 2016/0354127 A1* | 12/2016 | Lundquist ............ A61B 17/809 |
| 2017/0007305 A1 | 1/2017 | Hollis et al. |
| 2017/0014143 A1* | 1/2017 | Dayton ................. A61B 17/15 |
| 2017/0014173 A1 | 1/2017 | Smith et al. |
| 2017/0042598 A1* | 2/2017 | Santrock ............. A61B 17/151 |
| 2017/0042599 A1 | 2/2017 | Bays et al. |
| 2017/0049576 A1 | 2/2017 | Guilford et al. |
| 2017/0079669 A1 | 3/2017 | Bays et al. |
| 2017/0164989 A1 | 6/2017 | Weiner et al. |
| 2017/0172638 A1 | 6/2017 | Santrock et al. |
| 2017/0196602 A1* | 7/2017 | Lundquist ............ A61B 17/809 |
| 2018/0125504 A1 | 5/2018 | Dayton et al. |
| 2019/0175238 A1 | 6/2019 | Dayton et al. |
| 2019/0274745 A1 | 9/2019 | Smith et al. |
| 2019/0328435 A1 | 10/2019 | Bays et al. |
| 2019/0328436 A1 | 10/2019 | Bays et al. |
| 2019/0357919 A1 | 11/2019 | Fallin et al. |
| 2020/0015856 A1 | 1/2020 | Treace et al. |
| 2020/0078025 A1 | 3/2020 | Fallin et al. |
| 2020/0138491 A1* | 5/2020 | Brigido ................. A61B 17/84 |
| 2020/0197021 A1* | 6/2020 | Dayton ................. A61B 17/15 |
| 2020/0375644 A1* | 12/2020 | Smith ................... A61B 17/15 |
| 2021/0022879 A1* | 1/2021 | Hollis ............... A61B 17/1775 |
| 2021/0026357 A1 | 2/2021 | Hollis et al. |
| 2021/0077192 A1* | 3/2021 | Perler ................ A61B 17/151 |
| 2021/0282823 A1* | 9/2021 | Day .................. A61B 17/1728 |
| 2021/0307763 A1 | 10/2021 | Fallin et al. |
| 2021/0338450 A1 | 11/2021 | Hollis et al. |

FOREIGN PATENT DOCUMENTS

| | | |
|---|---|---|
| WO | WO 04/075775 | 9/2004 |
| WO | WO 04/089227 | 10/2004 |
| WO | WO 05/041785 | 5/2005 |
| WO | WO 07/008348 | 1/2007 |
| WO | WO 08/097781 | 8/2008 |
| WO | WO 16/134154 | 8/2016 |
| WO | WO 16/134160 | 8/2016 |
| WO | WO 17/011589 | 1/2017 |
| WO | WO 17/031000 | 2/2017 |
| WO | WO 17/049056 | 3/2017 |
| WO | WO 21/021640 | 2/2021 |
| WO | WO 21/026357 | 2/2021 |

OTHER PUBLICATIONS

Comprehensive Solutions for Forefoot and Midfood Surgery using the Mini TightRope System, Arthrex, Inc., www.arthrex.com 2012, 15 pp.

DiDomenico, Lawrence A., et al. "Lapidus Bunionectomy: First Metatarsal-Cuneiform Arthrodesis," Souhterland, Chapter 31, Aug. 18, 2012.

Distal Extremities Orthopaedic Update, Arthrex, Inc., www.arthrex.com, 2014, 24 pp.

Dobbe, et al., "Computer-Assisted and Patient-Specific 3-D Planning and Evaluation of a Single-Cut Rotational Osteotomy for Complex Long-Bone Deformities", Med Biol Eng Comput (2011) 49:1363-1370.

Foot & Ankle Repair and Reconstruction Technology, Arthrex GmbH, www.arthrex.com, 2016, 86 pp.

Gregg, Julie, et al., "Plantar Plate Repair and Weil Osteotomy for Meteatarsophalangeal Joint Instability", Foot and Ankle Surgery 13(2007) 116-121.

Meyer, D.C., et al., "A New Methodology for the Planning of Single-Cut Corrective Osteotomies of Mal-Aligned Long Bones", Clinical Biomechanics 20(2005) 223-227.

Oscillating Saw Attachment for EPD/APD, Colibri II and Small Electric Drive, Synthes GmbH, www.synthes.com, 2012, 2 pp.

Scarf Osteotomy Technical Information Sheet, TALUS group of GECO, www.geco-medical.org, 2004, 2 pp.

Shurnas, Paul S., M.D., et al., Proximal Metatarsal Opening Wedge Osteotomy: PMOW—Arthrex LPS System, Arthrex, Inc., www.arthrex.com, 2008, 1 pp.

Speed Triad Medial Technique, BioMedical Enterprises, www.bme-tx.com, 2015, 2 pp.

The Accu-Cut Osteotomy Guide System, BioPro Implants, www.bioproimplants.com, Brochure No. 16932 Rev07, 2 pp.

The Accu-Cut Osteotomy Guide System, BioPro Implants, www.bioproimplants.com, Brochure No. 17136, Rev4, 2 pp.

The Next Generation in Foot & Ankle Repair and Reconstruction Technology, Arthrex, Inc., www.arthrex.com, 2016, 76 pp.

Weil, Lowell Jr., et al., "Anatomic Plantar Plate Repair Using the Weil Metatarsal Osteotomy Approach", Foot & Ankle Specialist, http://fas.sagepub.com/, 2011, 7 pp.

International Search Report and Written Opinion dated Jul. 22, 2021 in application No. PCT/US21/18398.

* cited by examiner

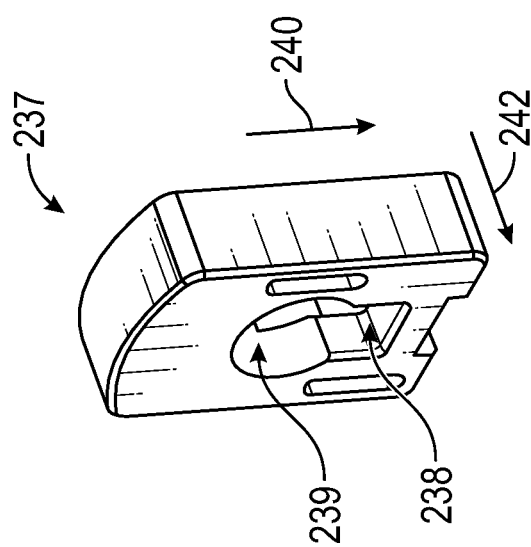
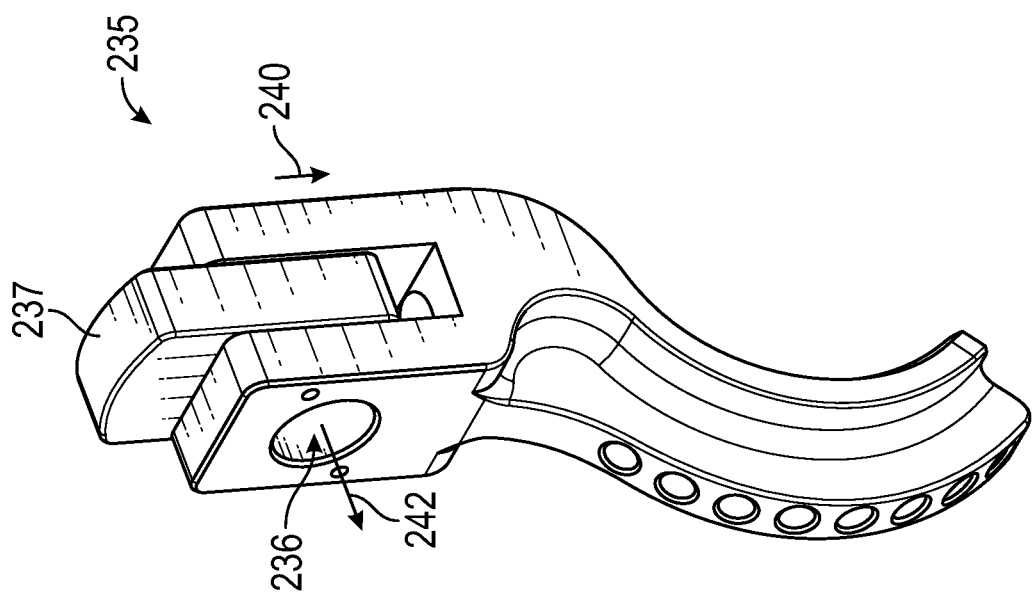
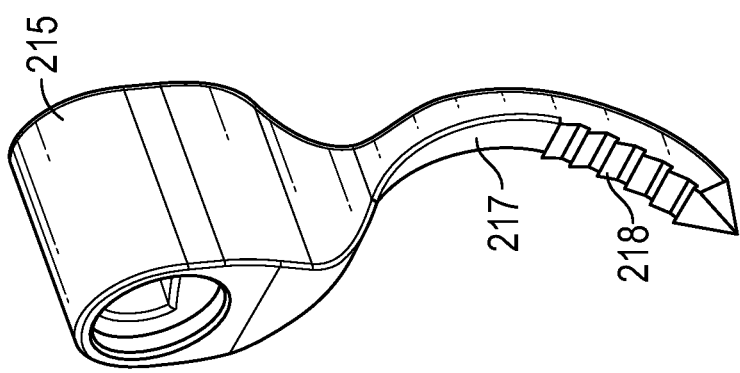

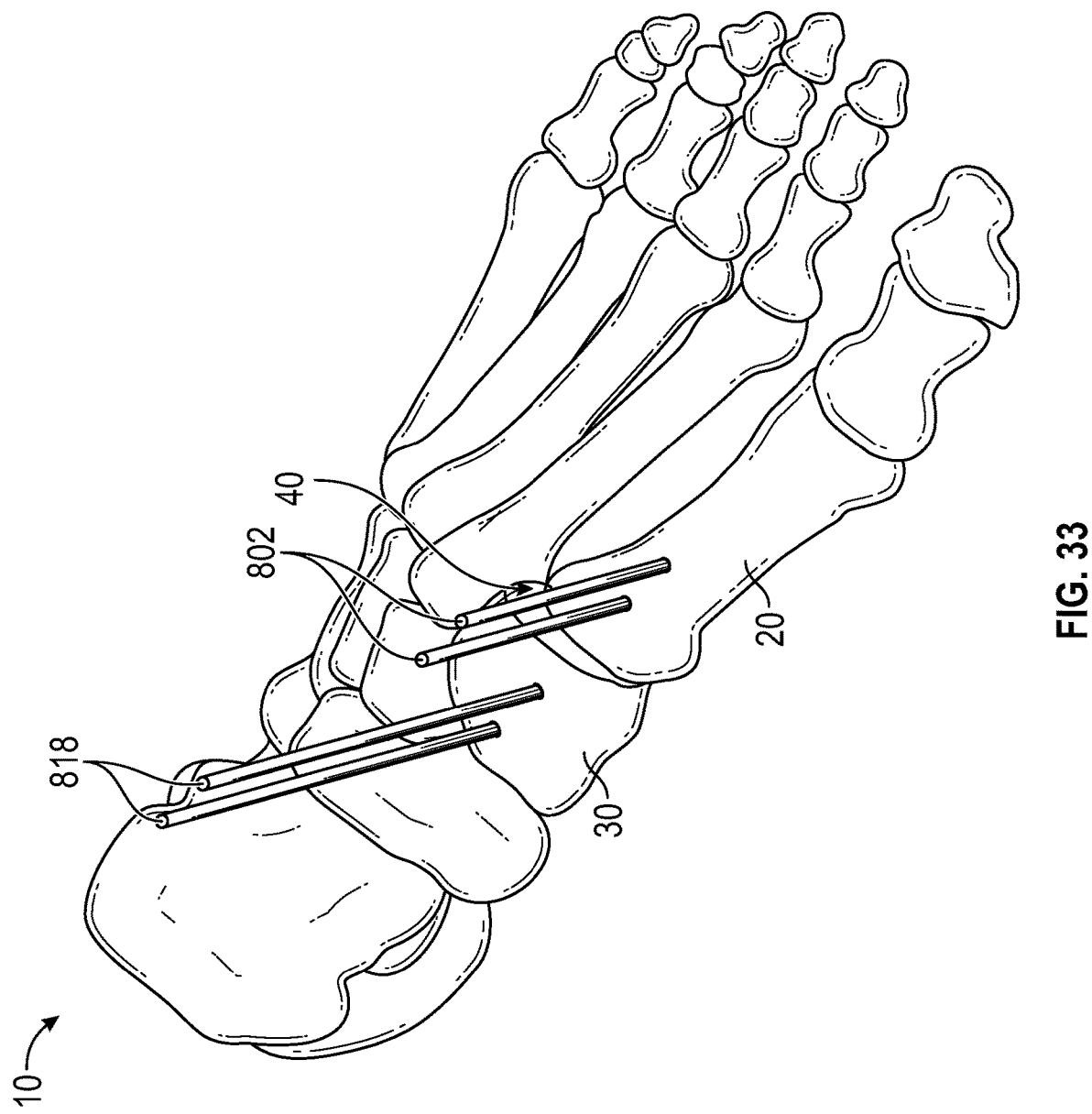

SYSTEMS AND METHODS FOR LAPIDUS REPAIR OF BUNIONS

CROSS-REFERENCE TO RELATED APPLICATIONS

This application claims the benefit of U.S. Provisional Application Ser. No. 62/978,683, filed Feb. 19, 2020, titled SYSTEMS AND METHODS FOR LAPIDUS REPAIR OF BUNIONS; U.S. Provisional Application Ser. No. 63/018,793, filed May 1, 2020, titled SYSTEMS AND METHODS FOR LAPIDUS REPAIR OF BUNIONS; and U.S. Provisional Application Ser. No. 63/125,272, filed Dec. 14, 2020, titled SYSTEMS AND METHODS FOR LAPIDUS REPAIR OF BUNIONS, all of which are incorporated by reference herein in their entirety and for all purposes.

FIELD

The present disclosure relates to medical devices and more particularly to systems and methods for repair of bunions using the Lapidus bunionectomy technique.

BACKGROUND

Bunions are a progressive disorder typically beginning with a leaning of the big toe, which can gradually change the angle of the bones and produce a characteristic bump on the medial side of the metatarsal near the joint of the metatarsal with the proximal phalanx. Specifically, the bunion is the prominence made of bone and at times an inflamed bursa. Hallux valgus is the condition in which the big toe deviates from the normal position toward the direction of the second toe.

Bunion correction or repair is a common surgery with over 100,000 surgeries performed annually in the U.S. In the Lapidus bunionectomy procedure for bunion correction, the first tarsometatarsal joint is fused to correct deformity of the joint and to prevent further movement of the joint. However, existing Lapidus bunionectomy techniques may be difficult to perform with the desired precision.

SUMMARY

Example embodiments described herein have innovative features, no single one of which is indispensable or solely responsible for their desirable attributes. Without limiting the scope of the claims, some of the advantageous features will now be summarized.

In a first aspect, a method of correcting a bunion comprises inserting a plurality of metatarsal pins into a first metatarsal of a foot at a first predetermined spacing relative to a first tarsometatarsal (TMT) joint, excising the first TMT joint of the foot, inserting a plurality of cuneiform pins into the first cuneiform at a second predetermined spacing relative to the first TMT joint, compressing the first TMT joint using a compressor block such that a cut face of the first metatarsal contacts a cut face of the first cuneiform, and fixing the first TMT joint. The excising comprises cutting a base of the first metatarsal proximate the first TMT joint and cutting a base of a first cuneiform of the foot proximate the first TMT joint.

In some embodiments, the first TMT joint is fixed using a bone plate and a plurality of bone screws, and at least one of the plurality of bone screws is a cross screw extending at an angle of less than 90 degrees relative to the bone plate. In some embodiments, the cross screw extends through the bone plate, the first metatarsal, and at least a portion of a second metatarsal of the foot or a second cuneiform of the foot.

In some embodiments, the method further comprises placing a staple through the bone plate such that a first leg of the staple is seated within the first cuneiform and a second leg of the staple is seated within the first metatarsal. In some embodiments, the bone plate comprises a cross screw aperture shaped to guide placement of the cross screw such that the second leg of the staple does not impede placement of the cross screw.

In some embodiments, the plurality of metatarsal pins are inserted prior to excising the first TMT joint.

In some embodiments, the plurality of cuneiform pins are inserted prior to cutting the base of the first cuneiform.

In some embodiments, the method further comprises placing a cut guide across a dorsal side of the first TMT joint prior to inserting the plurality of metatarsal pins and the plurality of cuneiform pins. The cut guide may comprise a body, a plurality of proximal pin holes extending parallel through the body, a plurality of distal pin holes extending through the body parallel to the proximal pin holes, and a joint-seeking paddle extending downward from the body between the proximal pin holes and the distal pin holes such that, when the joint-seeking paddle is at least partially disposed within the first TMT joint, the distal pin holes define the first predetermined spacing relative to the first TMT joint and the proximal pin holes define the second predetermined spacing relative to the first TMT joint. In some embodiments, the cut guide further comprises a proximal slot extending through the body and a distal slot extending through the body on an opposite side of the joint-seeking paddle relative to the proximal slot, such that the distal slot defines a cutting plane for cutting the base of the first metatarsal and the proximal slot defines a cutting plane for cutting the base of the first cuneiform.

In some embodiments, the method further comprises, prior to compressing the first TMT joint, adjusting an alignment of the first metatarsal within a frontal plane of the foot using a control handle coupled to the plurality of metatarsal pins and adjusting an alignment of the first metatarsal within a transverse plane of the foot using a linear reducer comprising a medial hook disposed on a medial side of the first metatarsal and a lateral hook disposed on a lateral side of a second metatarsal of the foot, the lateral hook having an adjustable spacing relative to the medial hook. In some embodiments, the method further comprises inserting a medial hook pin through an aperture of the medial hook and into the first metatarsal to rotationally fix the first metatarsal relative to the medial hook prior to adjusting the alignment of the first metatarsal within the transverse plane. In some embodiments, at least one of the medial hook and the lateral hook comprises a radiolucent material. In some embodiments, the control handle comprises a handle portion and an engagement portion, the engagement portion comprising a plurality of pin apertures spaced apart at a same spacing as a distance between the metatarsal pins. In some embodiments, adjusting the alignment of the first metatarsal within the frontal plane comprises sliding the pin apertures over the metatarsal pins such that the engagement portion is proximate the first metatarsal, and rotating the first metatarsal about a longitudinal axis of the first metatarsal by applying torque to the control handle. In some embodiments, adjusting the alignment of the first metatarsal within the transverse plane comprises reducing the adjustable spacing between the lateral hook and the medial hook to bring a distal end of the first metatarsal closer to the second metatarsal. In some embodiments, the transverse plane alignment of the first metatarsal is adjusted while the first metatarsal is rotationally fixed relative to the medial hook of the linear reducer. In some embodiments, the plurality of cuneiform pins are inserted subsequent to adjusting the alignment of the first metatarsal in the frontal plane and the transverse plane.

In some embodiments, the compressor block comprises a body comprising a top surface and a bottom surface, a plurality of proximal pin holes extending through the body from the top surface to the bottom surface at a first angle of less than 90 degrees relative to the top surface and the bottom surface, and a plurality of distal pin holes extending through the body from the top surface to the bottom surface at the first angle relative to top surface and the bottom surface such that the proximal and distal pin holes are more closely spaced at the bottom surface relative to the top surface. In some embodiments, compressing the first TMT joint comprises inserting the cuneiform pins into the proximal pin holes at the bottom surface, inserting the metatarsal pins into the distal pin holes at the bottom surface, and sliding the compressor block along the cuneiform pins and the metatarsal pins toward the first TMT joint. In some embodiments, the compressor block further comprises at least one cross pin hole extending therethrough, each of the at least one cross pin holes defining a linear path passing diagonally through the first TMT joint when the compressor block is aligned proximate the first TMT joint on the cuneiform pins and the metatarsal pins. In some embodiments, the method further comprises, after compressing the first TMT joint, inserting a cross pin through the at least one cross pin hole to temporarily fix the first TMT joint, removing the cuneiform pins and the metatarsal pins from the foot, and removing the compressor block by sliding the compressor block away from the first TMT joint along the cross pin. In some embodiments, the method further comprises removing the cross pin after at least partially fixing the first TMT joint.

In some embodiments, the method further comprises placing a reversible cut guide across a dorsal side of the first TMT joint prior to inserting the plurality of metatarsal pins and the plurality of cuneiform pins, the reversible cut guide comprising a body, a plurality of first pin holes extending parallel through the body a plurality of second pin holes extending through the body parallel to the proximal pin holes, and a joint-seeking paddle extending downward from the body between the proximal pin holes and the distal pin holes such that, when the joint-seeking paddle is at least partially disposed within the first TMT joint, the first pin holes define the first predetermined spacing relative to the first TMT joint; and a slot extending through the body parallel to a plane of the joint-seeking paddle such that the slot defines a cutting plane for cutting the base of the first metatarsal or the base of the first cuneiform. In some embodiments, the base of the first metatarsal and the base of the first cuneiform are cut through the slot, the method further comprising, after cutting the base of the first metatarsal and prior to cutting the base of the first cuneiform, removing the reversible cut guide from the first TMT joint and placing the reversible cut guide across the dorsal side of the first TMT joint in a reversed orientation such that the slot defines a cutting plane for cutting the base of the first cuneiform.

In some embodiments, the method further comprises, prior to fixing the first TMT joint, re-cutting the base of the first metatarsal or the base of the first cuneiform to remove additional tissue. In some embodiments, the re-cutting is performed using a re-cut guide disposed on the metatarsal pins or the cuneiform pins, the re-cut guide defining a predetermined re-cut spacing smaller than a predetermined spacing defined by a cut guide used for the excising of the first TMT joint.

In some embodiments, the method further comprises, prior to fixing the first TMT joint, performing a frontal plane realignment comprising additional rotation within the frontal plane of the first metatarsal. In some embodiments, the frontal plane realignment is performed simultaneously with the compressing of the first TMT joint and the compressor block is configured as a realignment guide comprising angularly displaced pin holes such that placing the compressor block compresses the first TMT joint and maintains the additional rotation. In some embodiments, the frontal plane realignment is performed prior to the compressing of the first TMT joint and the frontal plane realignment comprises inserting, through a realignment guide, a plurality of replacement metatarsal pins at the first predetermined spacing relative to the first TMT joint, the replacement metatarsal pins being angularly displaced relative to the metatarsal pins; and aligning the replacement metatarsal pins linearly with the cuneiform pins prior to compressing the first TMT joint.

In a second aspect, a method of correcting a bunion comprises placing a cut guide across a dorsal side of a first tarsometatarsal (TMT) joint of a foot such that a plurality of first pin holes of the cut guide are disposed proximate a first metatarsal of the foot, a plurality of second pin holes of the cut guide are disposed proximate a first cuneiform of the foot, and a joint-seeking paddle of the cut guide is at least partially disposed within the first TMT joint; inserting a plurality of metatarsal pins into the first metatarsal through the first pin holes; cutting a base of the first metatarsal proximate the first TMT joint through a slot extending through the cut guide between the first pin holes and the joint-seeking paddle; removing the cut guide from the foot; replacing the cut guide across the dorsal side of the first TMT joint in a reversed configuration in which the metatarsal pins extend through the second pin holes; adjusting an alignment of the first metatarsal within at least one of a frontal plane and a transverse plane of the foot; inserting a plurality of cuneiform pins into the first cuneiform through the first pin holes; cutting a base of the first cuneiform proximate the first TMT joint through the slot; compressing the first TMT joint using a compressor block such that a cut face of the first metatarsal contacts a cut face of the first cuneiform; and fixing the first TMT joint.

In a third aspect, a bunion correction kit comprises a cut guide, a linear reducer, a control handle, and a compressor block. The cut guide comprises a body, a plurality of first pin holes extending parallel through the body and spaced apart at a first distance, a plurality of second pin holes extending through the body parallel to the first pin holes, the plurality of second pin holes spaced apart at the first distance, a joint-seeking paddle extending from the body between the proximal pin holes and the distal pin holes, and a slot extending through the body parallel to the joint-seeking paddle between the joint-seeking paddle and the first pin holes, the slot configured to guide cutting of a base of a first metatarsal or a first cuneiform when the joint-seeking paddle is at least partially disposed within a tarsometatarsal (TMT) joint. The linear reducer comprises a medial hook and a lateral hook, wherein a spacing between the medial hook and the lateral hook is adjustable to implement a transverse plane correction when the medial hook is seated against a medial side of the first metatarsal and the lateral hook is seated against a lateral side of a second metatarsal. The control handle comprising a handle portion and an engagement portion, the engagement portion comprising pin apertures spaced apart at the first distance. The compressor block comprises a body having a top surface and a bottom surface, a plurality of proximal pin holes extending through the body from the top surface to the bottom surface at a first angle of less than 90 degrees relative to the top surface and the bottom surface, and a plurality of distal pin holes extending through the body from the top surface to the bottom surface at the first angle relative to the top surface and the bottom surface, wherein the distal pin holes are convergent relative to the proximal pin holes such that the proximal and distal pin holes are more closely spaced at the bottom surface relative to the top surface.

In some embodiments, the bunion correction kit further comprises a re-cut guide, the re-cut guide comprising a body, a plurality of pin holes extending through the body and spaced apart at the first distance, a joint-seeking paddle extending from the body, and a slot extending through the body parallel to the joint-seeking paddle between the joint-seeking paddle and the pin holes, wherein the slot of the re-cut guide is closer to the pin holes of the re-cut guide as compared to a corresponding distance between the slot of the cut guide and the first pin holes of the cut guide.

In some embodiments, the compressor block is configured as a frontal plane realignment guide, at least two of the plurality of proximal pin holes being angularly displaced relative to at least two of the plurality of distal pin holes.

In some embodiments, the bunion correction kit further comprises one or more bone screws and a bone plate configured to receive the one or more bone screws, wherein the bone plate is configured to receive at least one of the one or more bone screws as a cross screw extending at an angle of less than 90 degrees relative to the bone plate.

In a fourth aspect, a linear reducer configured for adjusting a transverse plane alignment of a first metatarsal comprises a shaft having a proximal end and a distal end; a medial hook coupled to the shaft at the distal end, at least a portion of the medial hook comprising a concave curved surface shaped to seat against a medial side of a first metatarsal; a lateral hook slidably coupled to the shaft at an intermediate position between the proximal and distal ends, at least a portion of the medial hook comprising a concave curved surface shaped to seat against a lateral side of a second metatarsal while the medial hook is seated against the medial side of the first metatarsal; and a handle coupled to the shaft adjacent to a proximal side of the lateral hook, the linear position of the handle being adjustable along the shaft to move the lateral hook relative to the medial hook so as to implement a transverse plane correction when the medial hook is seated against a medial side of the first metatarsal and the lateral hook is seated against a lateral side of the second metatarsal.

In some embodiments, the shaft comprises a threaded exterior surface and wherein the handle comprises a threaded aperture extending therethrough and engaged with the threaded exterior surface of the shaft such that the linear position of the handle is adjustable by twisting the handle about the shaft.

In some embodiments, the medial hook comprises one or more apertures extending through the concave curved surface so as to accommodate a pin extending therethrough into the first metatarsal. In some embodiments, the medial hook is coupled to the shaft by a quick-release coupling movable from a locked position to an unlocked position and, in the unlocked position, the medial hook is slidable along a longitudinal axis of the shaft. In some embodiments, at least one of the medial hook and the lateral hook comprises a radiolucent material. In some embodiments, the radiolucent material comprises carbon fiber.

In a fifth aspect, a cut guide configured to guide cutting of a first metatarsal and a first cuneiform in a bunion correction procedure comprises a body comprising a first end and a second end opposite the first end along a longitudinal axis of the cut guide; a plurality of first pin holes extending parallel through the body proximate the first end, the first pin holes spaced apart along the longitudinal axis at a predetermined spacing; a plurality of second pin holes extending through the body proximate the second end and parallel to the first pin holes, the second pin holes spaced apart along the longitudinal axis at the predetermined spacing; a cutting slot extending through the body perpendicular to the longitudinal axis at a first intermediate location between the first pin holes and the second pin holes, the cutting slot sized and shaped to guide cutting of a bone by a sawblade inserted therethrough; and a joint-seeking paddle extending from a bone-facing surface of the body perpendicular to the longitudinal axis at a second intermediate location between the cutting slot and the second pin holes such that the cut guide can be placed across a first tarsometatarsal (TMT) joint with the joint-seeking paddle seated within the first TMT joint in either a metatarsal cutting orientation in which the cutting slot guides cutting a base of the first metatarsal or a cuneiform cutting orientation in which the cutting slot guides cutting a base of the first cuneiform.

In some embodiments, the cut guide further comprises one or more longitudinal apertures extending through the body perpendicular to and intersecting the cutting slot.

In some embodiments, the cut guide does not include a second cutting slot.

In some embodiments, the cut guide further comprises one or more convergent pin holes extending through the body at locations laterally displaced relative to the longitudinal axis, wherein each convergent pin hole meets the bone-facing surface at a first distance from the longitudinal axis and meets an upper surface of the body opposite the bone-facing surface at a second distance from the longitudinal axis, the second distance being greater than the first distance.

In some embodiments, the cutting slot comprises an intermediate section having a first width and terminal sections at opposite ends of the intermediate section, the terminal sections having a second width greater than the first width.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

FIGS. 3A-3H depict example linear reducers configured to be used in the Lapidus bunionectomy procedures described herein.

FIGS. 33-35 are perspective views of the bones of a foot, sequentially illustrating a re-cutting portion of an example Lapidus bunionectomy procedure performed using the example bunionectomy devices disclosed herein.

DETAILED DESCRIPTION

The following description is directed to certain implementations for the purpose of describing the innovative aspects of this disclosure. However, a person having ordinary skill in the art will readily recognize that the teachings herein can be applied in a multitude of different ways.

Generally described, the systems, devices, and methods described herein provide improved methods and tools that can be used to perform a Lapidus bunionectomy with desirable precision. Some or all of the tools and/or components described herein may be provided in a kit and can include a plurality of optional and/or interchangeable components that may be selected, positioned, secured, and or used at the time of the bunionectomy procedure. Accordingly, the Lapidus bunionectomy systems, devices, and methods disclosed herein may allow a surgeon to perform a bunionectomy more effectively, efficiently, and/or precisely than would be possible with conventional devices and procedures.

The embodiments described herein can be manufactured from a number of different materials or combinations of materials. Nitinol, stainless steel, titanium, and/or other materials may have desirable material properties for certain components described herein. Stainless steel and/or titanium may not possess shape memory or super elasticity, but may possess the mechanical properties for embodiments that may benefit from mechanical manipulation to achieve multiple configurations. Still other materials such as PEEK or other polymers may also possess material properties beneficial for the embodiments described herein. A combination of materials may also be preferred. For example, a combination of nitinol and titanium (e.g., a nitinol plate with titanium screws) may be the materials of choice for some embodiments. Those skilled in the art are aware of the typical materials and combinations of materials applicable to the current technology.

Figure 1:
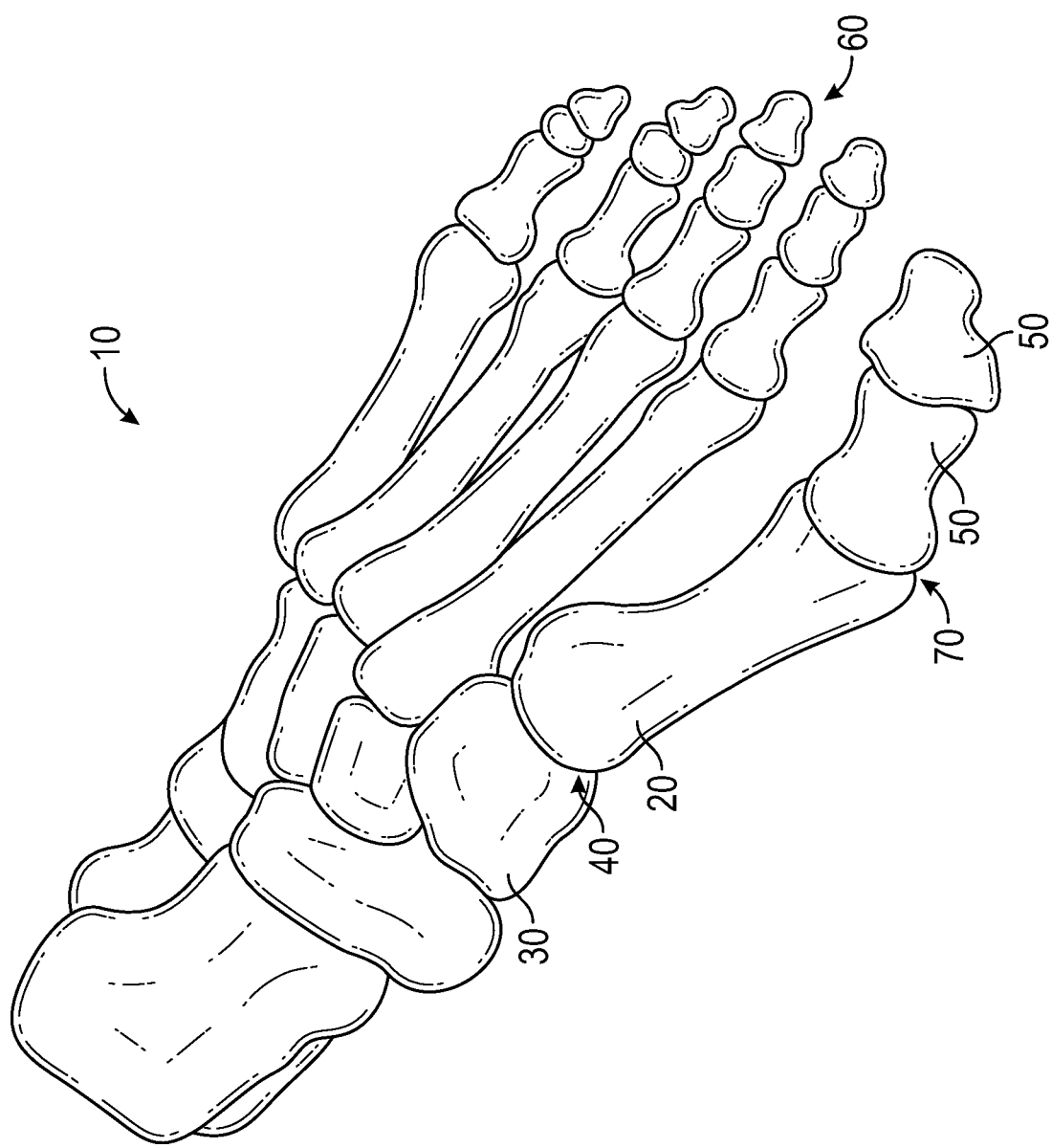
FIG. 1 is a perspective view of the bones of a foot having a bunion.

FIG. 1 is a perspective view of the bones of a foot 10 having a bunion, also known as hallux valgus. The foot 10 includes a first metatarsal 20 which articulates at its proximal end with the first cuneiform 30 (also known as the medial cuneiform) at the first tarsometatarsal (TMT) joint 40. The distal end of the first metatarsal 20 articulates with the phalanges 50 of the big toe. Intermetatarsal angle is defined as the angle between an axis of one metatarsal in relation to a second metatarsal, in the anatomic transverse plane. Rotation is defined as axial rotation about the axis of the metatarsal, in the anatomic frontal plane. A bunion as shown in FIG. 1 is characterized by an increased intermetatarsal angle and/or rotation of the first metatarsal 20 at the first TMT joint 40 such that the first metatarsal 20 extends away, or medially, from the remainder of the foot 10. When a bunion is present, the phalanges 50 of the big toe are typically angled inward, or laterally, toward the other phalanges 60, resulting in the characteristic bump at the metatarsophalangeal joint 70 which is the most prominent external indication of a bunion. The protruding metatarsophalangeal joint 70 may further be associated with a swollen bursal sac or osseous anomaly which may cause discomfort, difficulty with wearing shoes, and other inconveniences to the person having the bunion.

With reference to FIGS. 2A-7F, various devices and components are provided for use with an improved Lapidus bunionectomy procedure for correcting the TMT joint deformity of FIG. 1. Although the following description is made with reference to the Lapidus bunionectomy procedure, it will be understood that the various devices and components described herein are not limited to such procedures and may equally be used in other orthopedic procedures as will be understood by those skilled in the art.

Figure 2A:
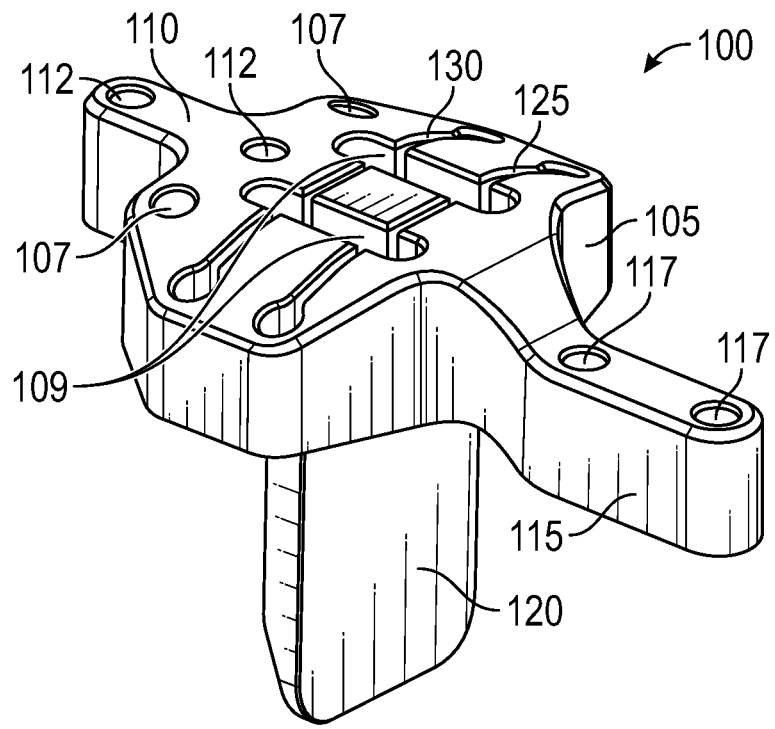
FIGS. 2A-2D depict an example cut guide configured as a cutting guide and a pin guide for the Lapidus bunionectomy procedures described herein.
Figure 2B:
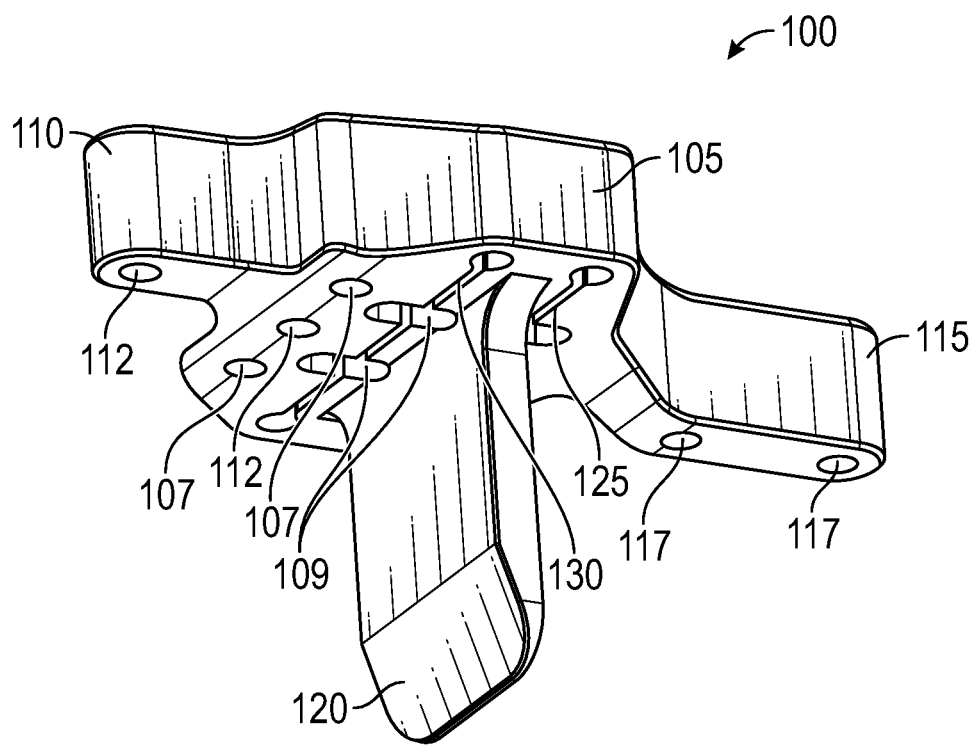
Figure 2C:
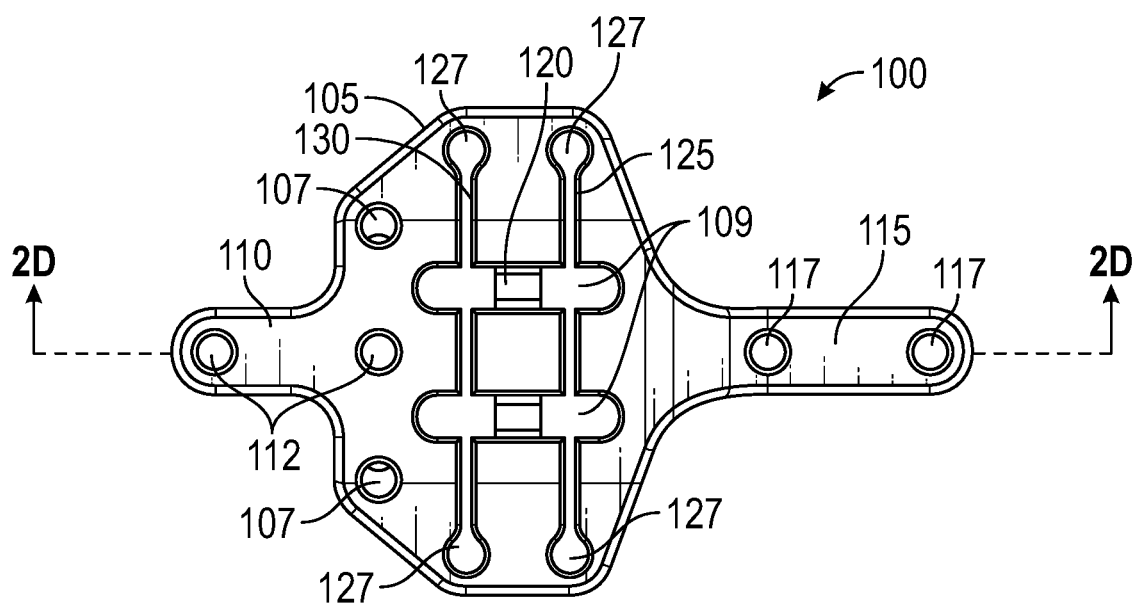
Figure 2D:
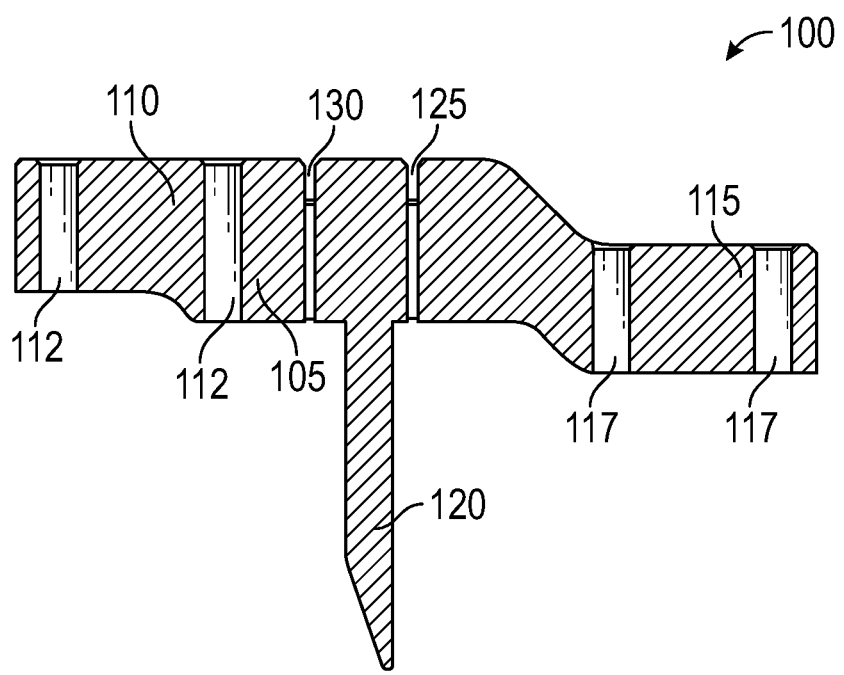

FIGS. 2A-2D depict an example cut guide 100 configured as a cutting guide and a pin guide for the Lapidus bunionectomy procedures described herein. FIGS. 2A and 2B are upper and lower perspective views of the cut guide 100, respectively. FIG. 2C is a top plan view of the cut guide 100. FIG. 2D is a cross-sectional side elevation view of the cut guide 100 taken about the line 2D-2D in FIG. 2C. The cut guide 100 may be a single integrally formed component and may comprise a metal, a plastic, or other suitable material.

The cut guide 100 generally includes a body 105, a proximal extension 110, a distal extension 115, and a paddle 120. The paddle 120 is sized and shaped to seat within a joint such as a TMT joint (e.g., between the first metatarsal and the first cuneiform), for example, after removing soft tissue such as the joint capsule around the joint. The relatively narrower and sloped terminal portion of the paddle 120 may facilitate insertion of the paddle 120 into the joint. In some embodiments, the paddle 120 is integrally formed with the body 105.

The body 105 of the cut guide 100 includes a distal slot 125 and a proximal slot 130. The distal slot 125 and the proximal slot 130 each pass through the full thickness of the body 105 and are sized and shaped to serve as a positioning guide for a sawblade in order to facilitate precise saw cuts at each side of the joint. For example, the distal slot 125 may be positioned at a predetermined distance relative to the distal plane of the paddle 120 to facilitate cutting the base of the first metatarsal when the paddle 120 is positioned within the first TMT joint. Similarly, the proximal slot 130 may be positioned on the opposite side (proximal plane) of the paddle to facilitate cutting the first cuneiform. The distal slot 125 and the proximal slot 130 may be identically or similarly shaped (e.g., may have the same length and/or width) such that the metatarsal and cuneiform cuts can be performed with the same or same type of saw blade. In some embodiments, the distal slot 125 and the proximal slot 130 may be parallel to each other and/or to the paddle 120, or may be angled relative to the plane of the paddle 120. In some embodiments, relatively wider terminal sections 127 at the ends of the slots 125, 130 may be provided for the placement of additional guide wires during cutting to prevent a saw blade from making an excessively wide cut when using the cut guide 100.

Proximal pin holes 112 extend through the full thickness of the cut guide 100. One or both of the proximal pin holes 112 can be disposed on the proximal extension 110 or within the body 105. The proximal pin holes 112 can each have a substantially circular profile sized to accommodate a surgical pin or wire for temporarily securing the cut guide to the foot. The proximal pin holes 112 serve as a guide such that two proximal pins or wires can be inserted at a predetermined spacing relative to each other and relative to the plane along which the first cuneiform is cut by a saw blade through the proximal slot 130. The proximal pin holes 112 extend vertically parallel to each other, as shown in FIG. 2D.

Distal pin holes 117 extend through the full thickness of the distal extension 115. Similar to the proximal pin holes 112, the distal pin holes 117 can each have a substantially circular profile sized to accommodate a surgical pin or wire for temporarily securing the cut guide to the foot, and may have the same diameter as the proximal pin holes 112. The distal pin holes 117 serve as a guide such that two distal pins or wires can be inserted at a predetermined spacing relative to each other and relative to the plane along which the first metatarsal is cut by a saw blade through the distal slot 125. The distal pin holes 117 extend vertically parallel to each other and parallel to the proximal pin holes 112, as shown in FIG. 2D. A plane which intersects the axes of the proximal pin holes 112 may be coplanar with a plane which intersects the axes of distal pin holes 117. The combination of the pin holes form a linear array of holes, spanning the TMT joint. A bottom or bone-facing surface of the distal extension 115 may not be coplanar with a bottom or bone-facing surface of the body 105 and/or the proximal extension 110, which may allow the cut guide 100 to be placed closer to the bone while allowing space for the osseous anatomy of the proximal metatarsal and the medial cuneiform. Further details are provided in U.S. Pat. No. 10,292,713, which is incorporated herein by reference.

In some embodiments, the body 105 of the cut guide 100 further includes one or more additional openings, such as additional convergent pin holes 107 and/or longitudinal apertures 109. The convergent pin holes 107 may be utilized to insert one or more additional pins or wires if additional stability is desired during a bunionectomy procedure. The longitudinal apertures 109 extend transverse to the slots 125, 130 and may provide an opening to facilitate x-ray visualization and/or any other suitable surgical imaging procedure to confirm and/or monitor the alignment of the cut guide during a bunionectomy procedure.

Figure 2E:
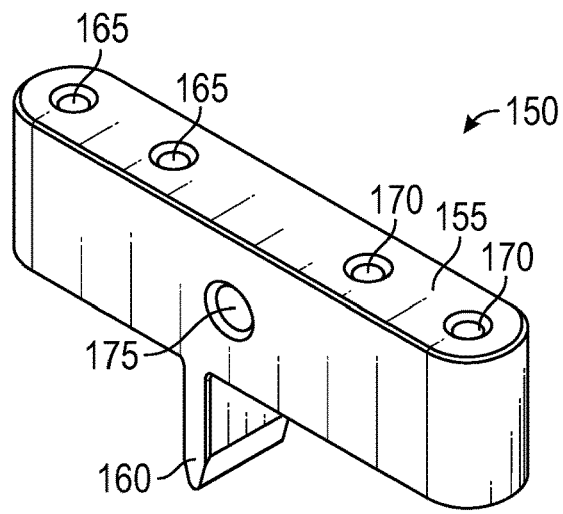
FIGS. 2E-2G depict an example free-hand pin guide for orienting the insertion of pins in the absence of the cut guide of FIGS. 2A-2D.
Figure 2F:
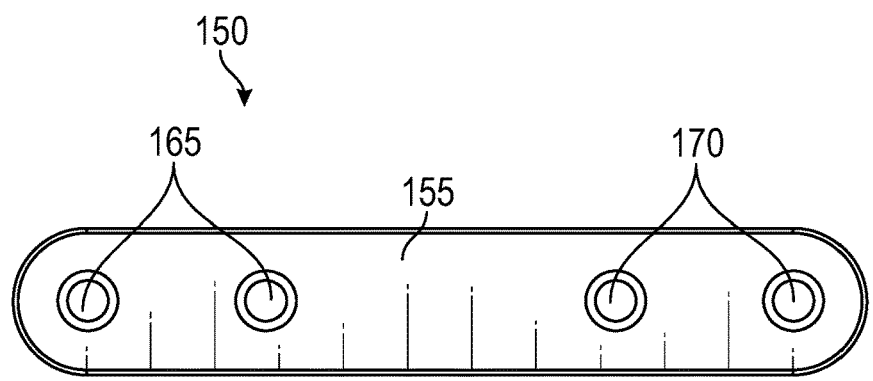
Figure 2G:
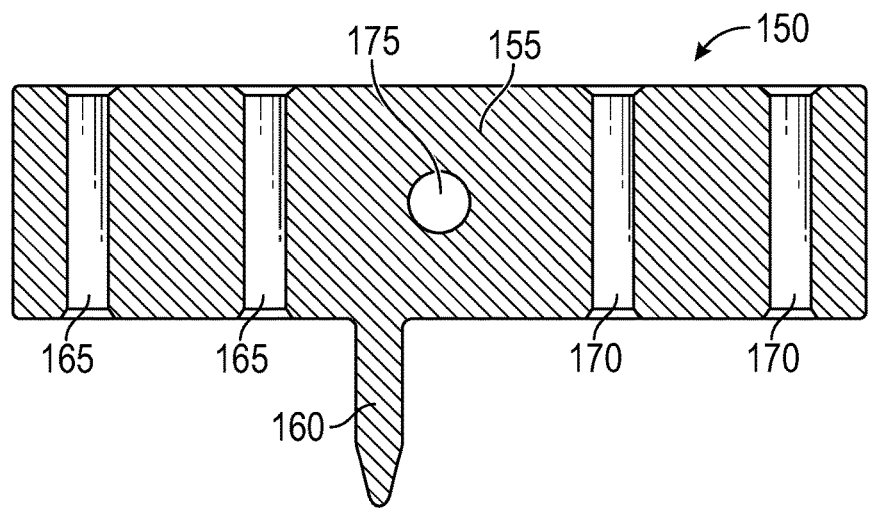

FIGS. 2E-2G depict an example free-hand pin guide 150 including an array of pin holes spanning the TMT joint for orienting the insertion of pins in the absence of the cut guide 100 of FIGS. 2A-2D. In some bunionectomy procedures, the cut guide 100 may not be used, for example, if the cut guide 100 does not fit within a joint, due to a surgeon's preference, or for any other reason that causes free-hand joint cuts to be made rather than cuts using the cut guide 100. The free-hand pin guide 150 generally comprises a body 155 and a paddle 160. Proximal pin holes 165 and distal pin holes 170 extend through the full thickness of the body 155. The proximal pin holes 165 may have the same relative spacing as the proximal pin holes 112 of the cut guide 100. Similarly, the distal pin holes 170 may have the same relative spacing as the distal pin holes 117 of the cut guide 100. A handle attachment aperture 175, which may be threaded, is provided for attaching a side-mounted handle which may assist the user in placing the free-hand pin guide 150. Similar to the proximal pin holes 112 and distal pin holes 117 of the cut guide 100, the proximal pin holes 165 and distal pin holes 170 of the free-hand pin guide 150 extend vertically parallel to each other. However, the spacing from the paddle 160 of the proximal pin holes 165 and the distal pin holes 170 of the free-hand pin guide 150 is slightly smaller than that of the proximal and distal pin holes 112, 117 relative to the paddle 120 of the cut guide 100 to compensate for the free-hand pin guide 150 being applied after the cuts have been made. Thus, the free-hand pin guide 150 allows the placement of pins or wires following a free-hand cut with the same spacing relative to the first TMT joint as if the cut guide 100 had been used to perform the cuts.

Figure 2H:
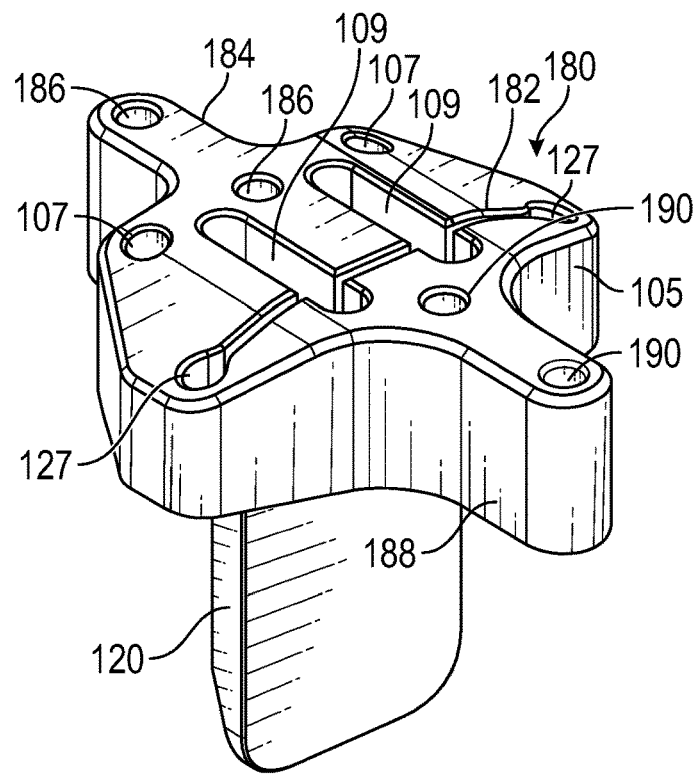
FIGS. 2H-2K depict an example cut guide configured as a cutting guide and a pin guide for the Lapidus bunionectomy procedures described herein.
Figure 2I:
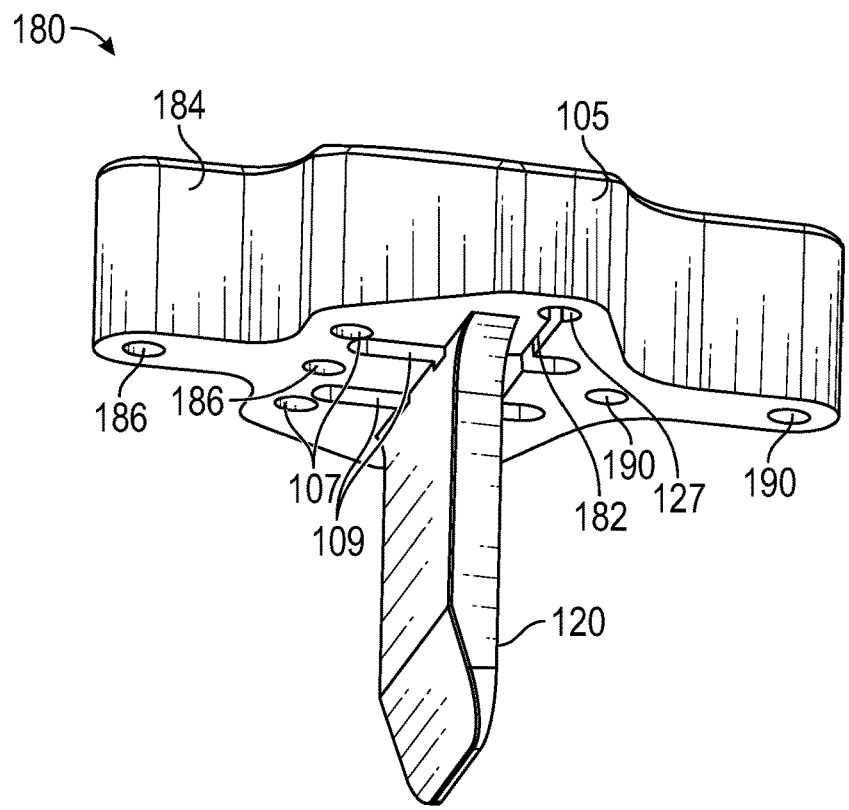
Figure 2J:
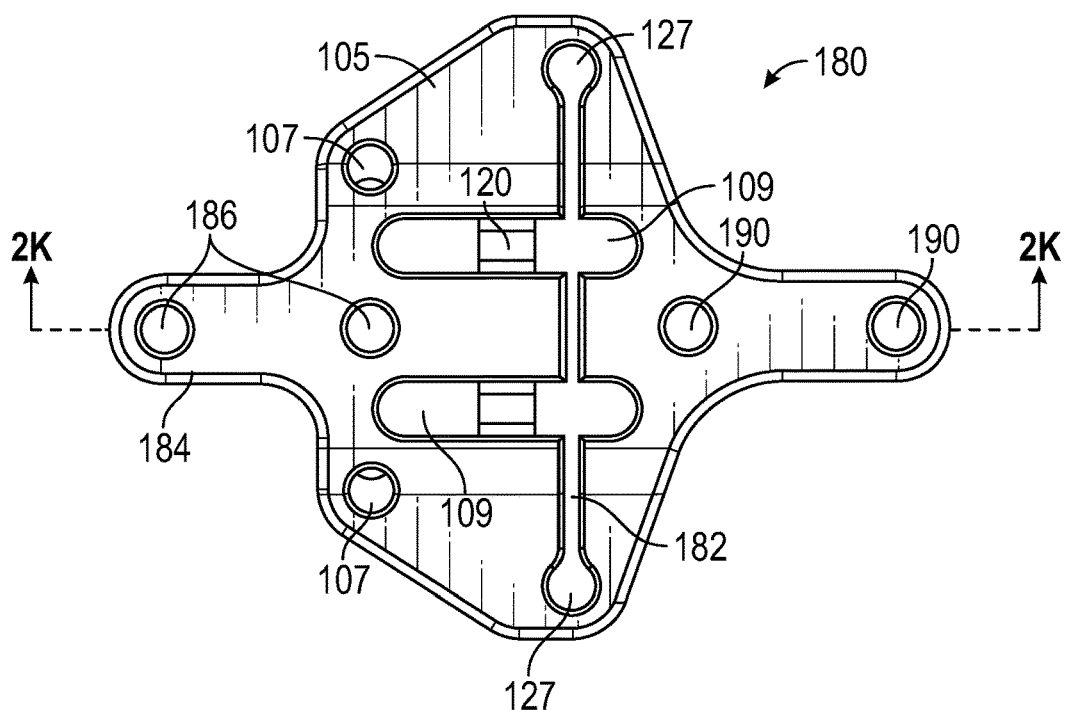
Figure 2K:
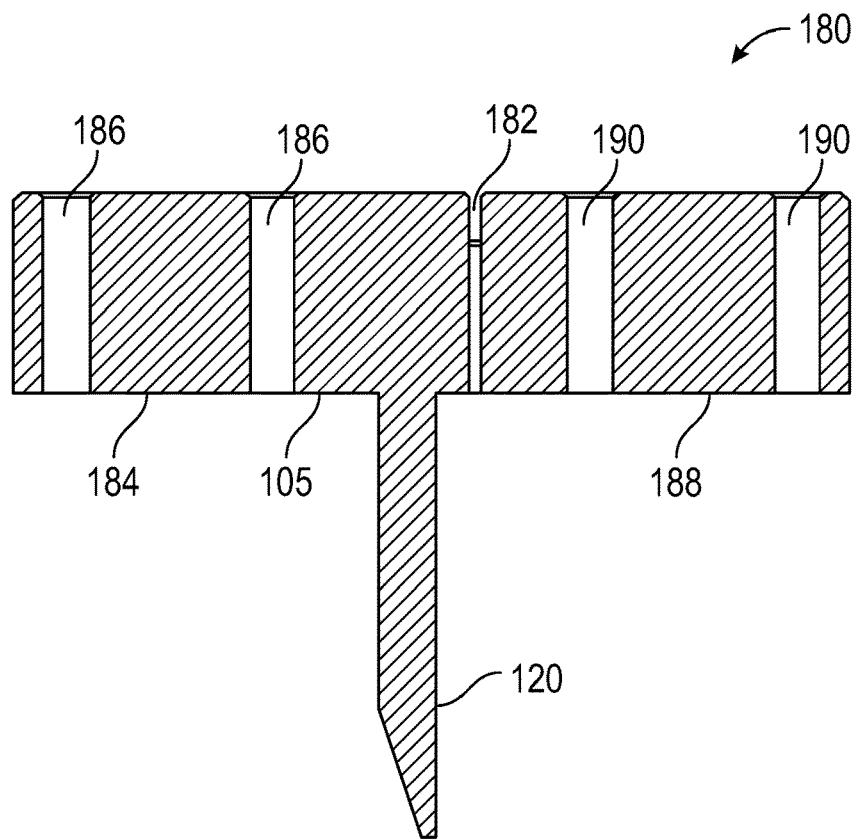

FIGS. 2H-2K depict an example reversible cut guide 180 configured as a cutting guide and a pin guide for the Lapidus bunionectomy procedures described herein. FIGS. 2H and 2I are upper and lower perspective views of the cut guide 180, respectively. FIG. 2J is a top plan view of the cut guide 180. FIG. 2K is a cross-sectional side elevation view of the cut guide 180 taken about the line 2K-2K in FIG. 2J. The cut guide 180 may be a single integrally formed component and may comprise a metal, a plastic, or other suitable material. The cut guide 180 is similar to the cut guide 100 of FIGS. 2A-2D, but may be reversible and is configured with a single slot 182 rather than proximal and distal slots 125, 130 of FIGS. 2A-2D.

The cut guide 180 generally includes a body 105, a first extension 184, a second extension 188, and a paddle 120. The paddle 120 is sized and shaped to seat within a joint such as a TMT joint (e.g., between the first metatarsal and the first cuneiform), for example, after removing soft tissue such as the joint capsule around the joint. The relatively narrower and sloped terminal portion of the paddle 120 may facilitate insertion of the paddle 120 into the joint. In some embodiments, the paddle 120 is integrally formed with the body 105.

The body 105 of the cut guide 180 includes a single cutting slot 182. The slot 182 passes through the full thickness of the body 105 and is sized and shaped to serve as a positioning guide for a sawblade in order to facilitate precise saw cuts at each side of the joint. For example, the slot 182 may be positioned at a predetermined distance relative to the plane of the adjacent surface of the paddle 120 to facilitate cutting the base of the first metatarsal or the first cuneiform, depending on the orientation of the cut guide 180, when the paddle 120 is positioned within the first TMT joint. In some embodiments, the slot 182 may be parallel to the paddle 120, or may be angled relative to the plane of the paddle 120. In some embodiments, relatively wider terminal sections 127 at the ends of the slot 182 may be provided for the placement of additional guide wires during cutting to prevent a saw blade from making an excessively wide cut when using the cut guide 180.

First pin holes 186 extend through the full thickness of the cut guide 180. One or both of the first pin holes 186 can be disposed on the first extension 184 or within the body 105. The first pin holes 186 can each have a substantially circular profile sized to accommodate a surgical pin or wire for temporarily securing the cut guide to the foot. The first pin holes 186 serve as a guide such that two pins or wires can be inserted at a predetermined spacing relative to each other and relative to the second pin holes 190. The first pin holes 186 extend vertically parallel to each other, as shown in FIG. 2K.

Second pin holes 190 extend through the full thickness of the cut guide 180. Similar to the first pin holes 186, the second pin holes 190 can each have a substantially circular profile sized to accommodate a surgical pin or wire for temporarily securing the cut guide 180 to the foot, and may have the same diameter as the first pin holes 186. The second pin holes 190 serve as a guide such that two distal pins or wires can be inserted at a predetermined spacing relative to each other and relative to the plane along which the first metatarsal or first cuneiform is cut by a saw blade through the slot 182. The second pin holes 190 extend vertically parallel to each other and parallel to the first pin holes 186, as shown in FIG. 2K. A plane which intersects the axes of the first pin holes 186 may be coplanar with a plane which intersects the axes of second pin holes 190. The combination of the pin holes form a linear array of holes, spanning the TMT joint. A bottom or bone-facing surface of the second extension 188 may be coplanar or substantially coplanar with a bottom or bone-facing surface of the body 105 and/or the first extension 184, which may allow the cut guide 180 to be placed across the TMT joint in either of two opposite orientations with the paddle 120 seated within the joint.

In some embodiments, the body 105 of the cut guide 180 further includes one or more additional openings, such as additional convergent pin holes 107 and/or longitudinal apertures 109. The convergent pin holes 107 may be utilized to insert one or more additional pins or wires if additional stability is desired during a bunionectomy procedure. The longitudinal apertures 109 extend transverse to the slot 182 and may provide an opening to facilitate x-ray visualization and/or any other suitable surgical imaging procedure to confirm and/or monitor the alignment of the cut guide during a bunionectomy procedure.

Figure 2L:
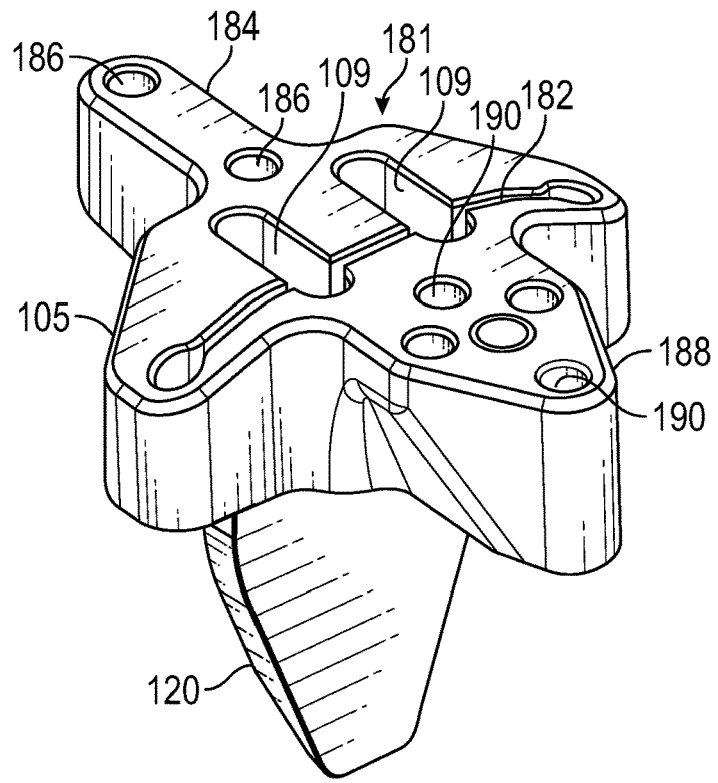
FIGS. 2L-2N depict an example cut guide configured as a cutting guide and a pin guide for the Lapidus bunionectomy procedures described herein.
Figure 2M:
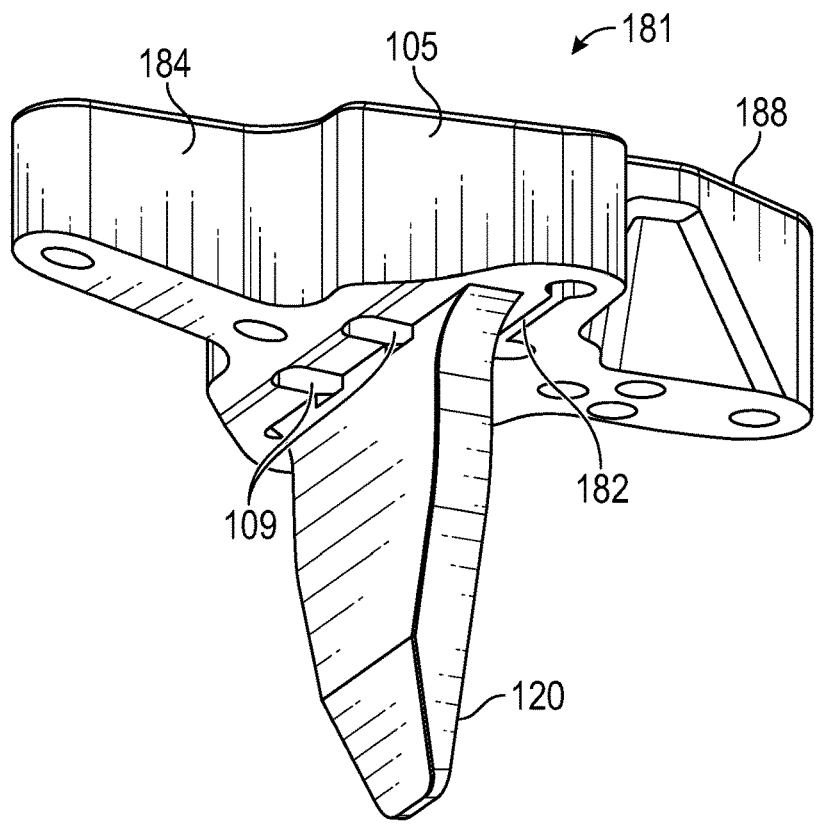
Figure 2N:
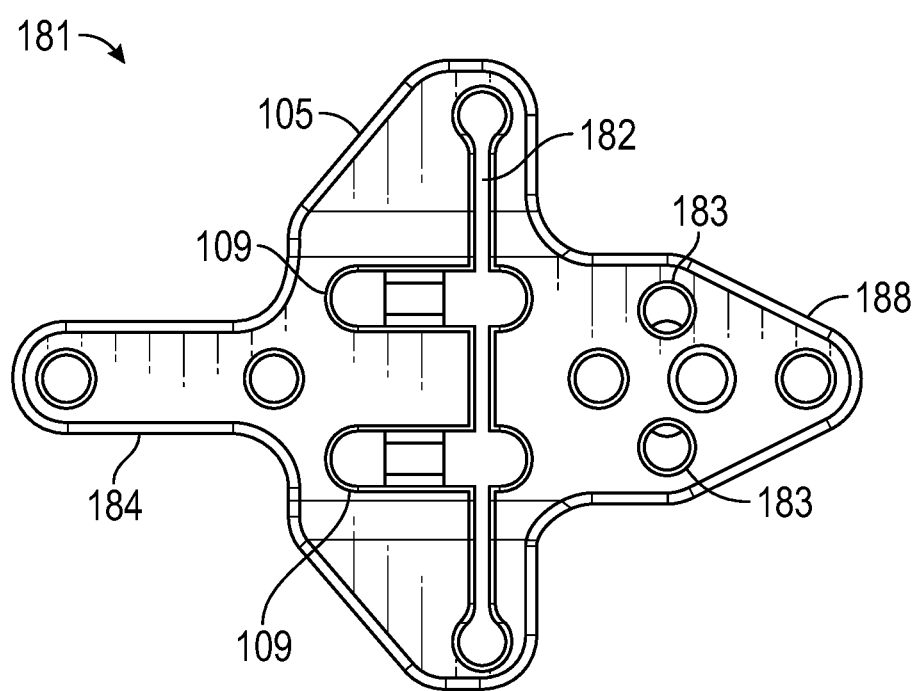

FIGS. 2L-2N depict a further example reversible cut guide 181 configured as a cutting guide and a pin guide for the Lapidus bunionectomy procedures described herein. FIGS. 2L and 2M are upper and lower perspective views of the cut guide 181, respectively. FIG. 2N is a top plan view of the cut guide 181. The cut guide 181 may be a single integrally formed component and may comprise a metal, a plastic, or other suitable material. The cut guide 181 is similar to the cut guide 180 of FIGS. 2H-2K, including a reversible configuration with a single slot 182.

The cut guide 181 generally includes a body 105, a first extension 184, a second extension 188, and a paddle 120. The first extension 184 and the second extension 188 can include first pin holes 186 and second pin holes 190 as described above with reference to FIGS. 2H-2K. The paddle 120 is sized and shaped to seat within a joint such as a TMT joint (e.g., between the first metatarsal and the first cuneiform), for example, after removing soft tissue such as the joint capsule around the joint. The relatively narrower and sloped terminal portion of the paddle 120 may facilitate insertion of the paddle 120 into the joint. In some embodiments, the paddle 120 is integrally formed with the body 105.

In the example embodiment of FIGS. 2L-2N, the body 105 of the cut guide 181 further includes one or more additional openings, such as additional convergent pin holes 183, extending through the second extension 188. The convergent pin holes 183 may be utilized to insert one or more additional pins or wires if additional stability is desired during a bunionectomy procedure. Similar to the cut guide 180 of FIGS. 2H-2K, longitudinal apertures 109 extend transverse to the slot 182 and may provide an opening to facilitate x-ray visualization and/or any other suitable surgical imaging procedure to confirm and/or monitor the alignment of the cut guide during a bunionectomy procedure.

Figure 3A:
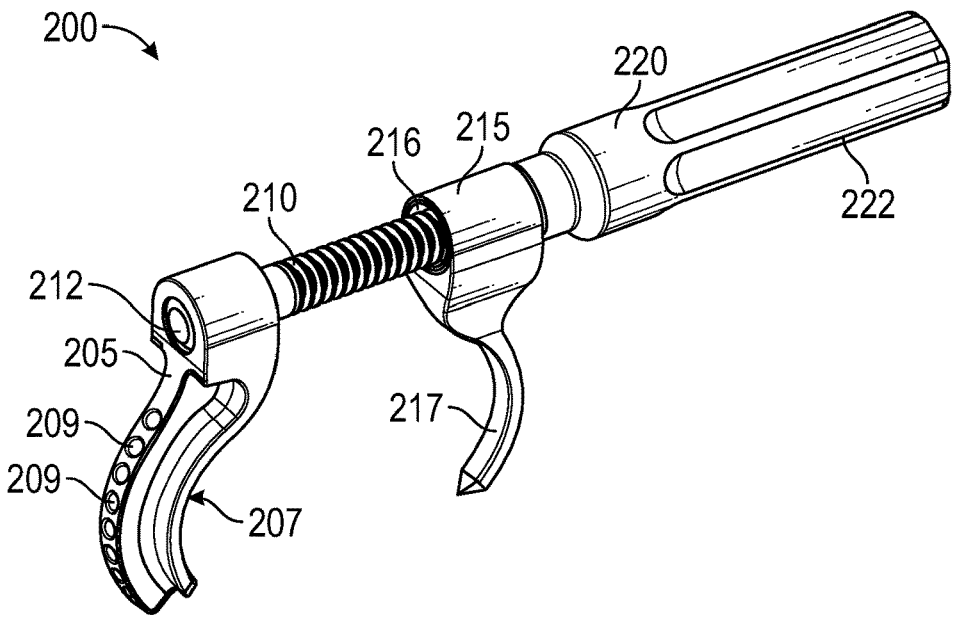
Figure 3B:
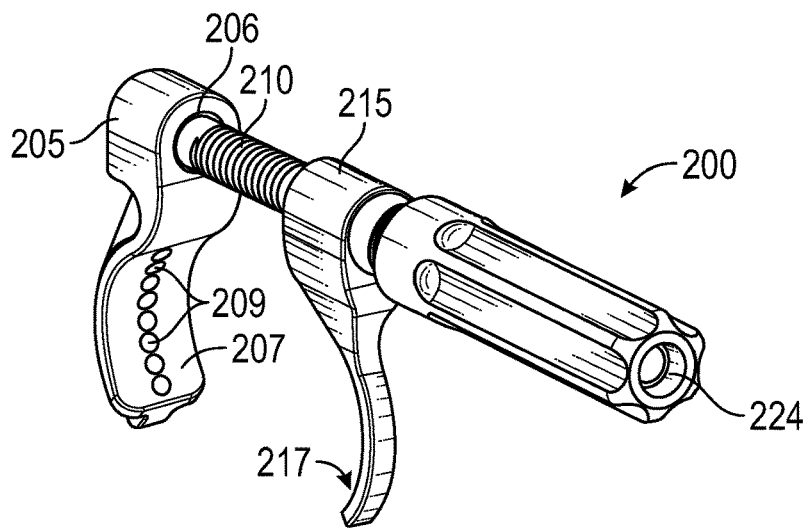
Figure 3C:
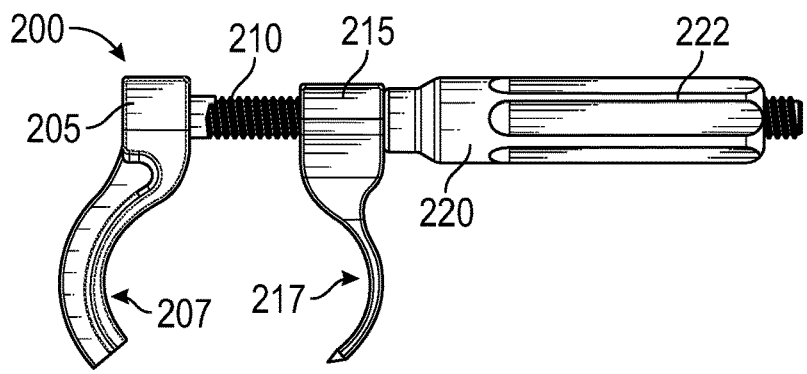

FIGS. 3A-3H depict an example linear reducer 200 configured to be used in the Lapidus bunionectomy procedures described herein. With reference to FIGS. 3A-3C, the linear reducer 200 includes a medial hook 205, a threaded shaft 210, a lateral hook 215, and a handle 220. As will be described in greater detail with reference to FIGS. 10-14, the linear reducer 200 is suitable for applying correction within the transverse plane during a Lapidus bunionectomy procedure by moving the first and second metatarsals closer together to reduce the intermetatarsal angle, as well as maintaining the desired correction of the frontal plane when a pin is placed within medial hook pin holes 209.

The medial hook 205 includes a coupling aperture 206 sized and shaped to couple to a first end 212 of the threaded shaft 210. In some embodiments, the medial hook 205 may be fixedly coupled to the threaded shaft 210 such that the medial hook 205 is neither rotatable nor translatable relative to the threaded shaft 210. The medial hook 205 includes a curved engagement surface 207 configured to rest against the medial side of the foot. One or more medial hook pin holes 209 extend from the engagement surface 207 through the full thickness of the medial hook 205 such that a pin may be placed through the medial hook 205 to temporarily secure the medial hook 205 to the toe.

The lateral hook 215 includes a coupling aperture 216 sized and shaped to receive the threaded shaft 210 therethrough. The lateral hook 215 may have a smooth interior surface having a diameter at least as large as the full diameter of the threaded shaft 210 such that the lateral hook 215 can translate along the threaded shaft 210 without rotating. Other features of the coupling aperture may include a non-cylindrical profile such that, when the lateral hook 215 is assembled to the threaded shaft 210, the non-cylindrical profile prevents rotation of the lateral hook 215 about the axis of the threaded shaft 210. The lateral hook 217 includes a curved engagement surface 217 configured to rest against the lateral side of a bone such as the second metatarsal. In some embodiments, the engagement surface 217 may be inserted through an incision between, for example, the second and third toes such that the engagement surface 217 can be placed against the lateral side of the second metatarsal for transverse plane correction.

In various embodiments, the components of the linear reducer 200 may comprise a variety of materials. For example, the handle 220, the threaded shaft 210, the medial hook 205, and/or the lateral hook 205 may comprise a metal, a plastic or polymeric material, or the like. In some embodiments, the medial hook 205 and/or the lateral hook 215 may comprise a radiolucent material. Advantageously, a radiolucent material may be at least partially transmissive to x-rays or other radiation associated with medical imaging, so as to facilitate imaging of the bones of the foot while the linear reducer 200 is applied. Example radiolucent materials suitable for the medial hook 205 and/or the lateral hook 215 include carbon fiber, polymeric materials, and/or composite materials such as a carbon fiber reinforced polymer.

The handle 220 includes one or more grip features 222 such as knurling to facilitate a user's grip while rotating the handle 220. A threaded aperture 224 extends longitudinally through the handle 220. The interior threading of the threaded aperture 224 is sized and spaced to mesh with the exterior threading of the threaded shaft 210. In some embodiments, only a portion of the threaded aperture 224 is threaded, for example, with any remaining length drilled to a larger diameter to allow clear pass-through of the threaded shaft 210. Thus, the interior threading of the threaded aperture 224 allows the handle 220 to be translated to a desired position along the threaded shaft 210 by rotating the handle 220 about the threaded shaft 210. Accordingly, when a user wishes to decrease the spacing between the medial hook 205 and the lateral hook 215, the user twists the handle 220 clockwise about the threaded shaft 210 such that the handle 220 pushes the lateral hook 215 along the threaded shaft 210 toward the medial hook 205. Friction between the interior threading of the threaded aperture 224 and the exterior threading of the threaded shaft 210 prevents the lateral hook 215 and handle 220 from being pushed outward away from the medial hook 205 unless the handle 220 is twisted.

FIG. 3D illustrates an alternative embodiment of the lateral hook 215. In the alternative lateral hook 215 of FIG. 3D, the engagement surface 217 includes one or more bone engagement features 218 configured to provide an improved grip on the lateral surface of the second metatarsal bone during a Lapidus bunionectomy. In some cases, the bone engagement features 218 may reduce the probability of the lateral hook 215 sliding upward away from the second metatarsal during or following reduction of the intermetatarsal angle within the transverse plane.

Figure 3G:
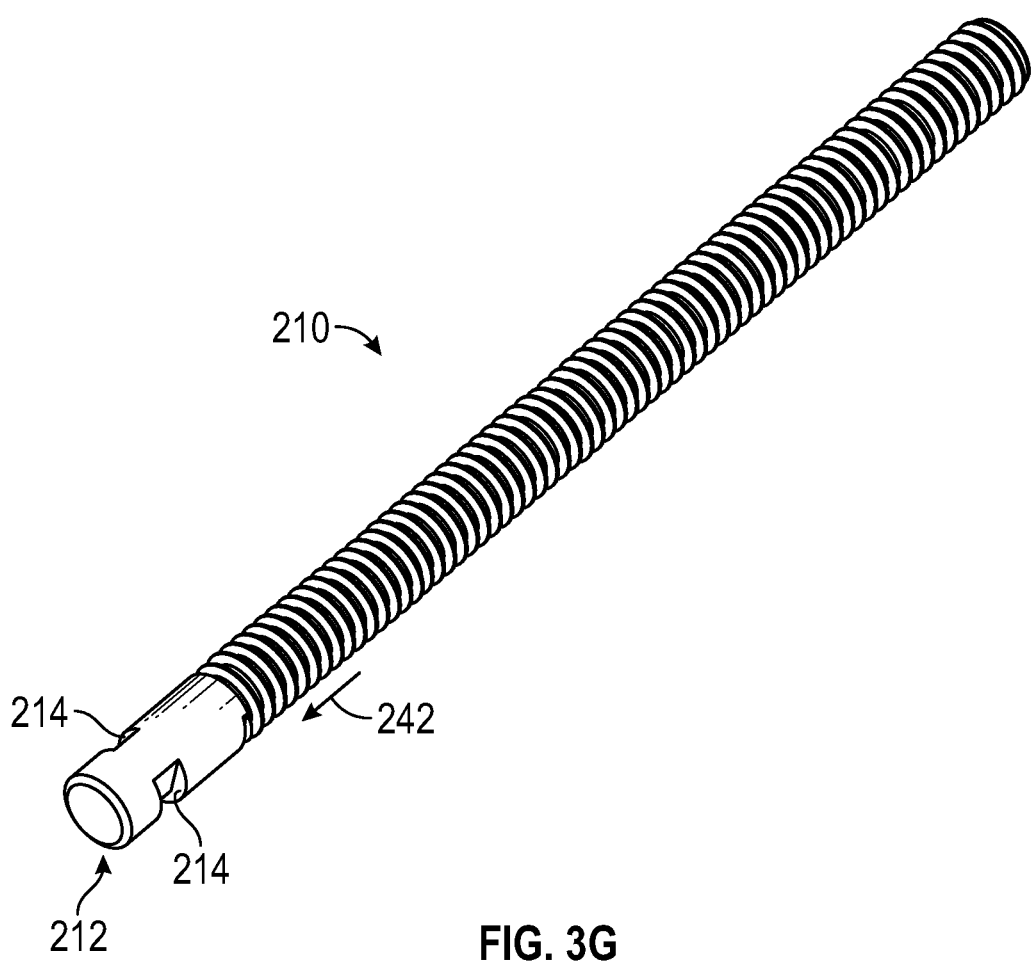

FIGS. 3E-3G illustrate a quick-release feature that may be incorporated at the medial hook of the linear reducer 200. In a quick-release embodiment of the linear reducer 200, the fixedly coupled medial hook 205 of FIGS. 3A-3C is replaced by a quick-release medial hook 235. The quick-release medial hook 235 includes an aperture 236 large enough to slidably accommodate the threaded shaft 210. A quick-release insert 237 is insertable within the upper portion of the quick-release medial hook 235. The quick-release insert 237 has a coupling aperture 239 including a locking portion 238 configured to interlock with notches 214 near the first end 212 of the threaded shaft 210. Thus, when the quick-release insert 237 is in the raised position shown in FIG. 3E, the locking portion 238 is engaged within the notches 214 to fixedly couple the quick-release medial hook 235 to the threaded shaft.

When it is desired to remove the linear reducer 200 from the foot, the quick-release insert 237 is pushed downward along the direction 240. As the quick-release insert 237 moves downward, the locking portion 238 disengages from the notches 214 in the threaded shaft 210, such that the entire quick-release medial hook becomes slidable along a longitudinal direction 242 relative to the threaded shaft 210. For example, with the quick-release medial hook 235 pinned to the bone, the threaded shaft 210 may be removed through the coupling aperture 216 of the lateral hook 215, and the lateral hook 215 may be removed from the foot substantially vertically. The medial hook 205 may then be unpinned and removed from the foot easily.

Figure 3H:
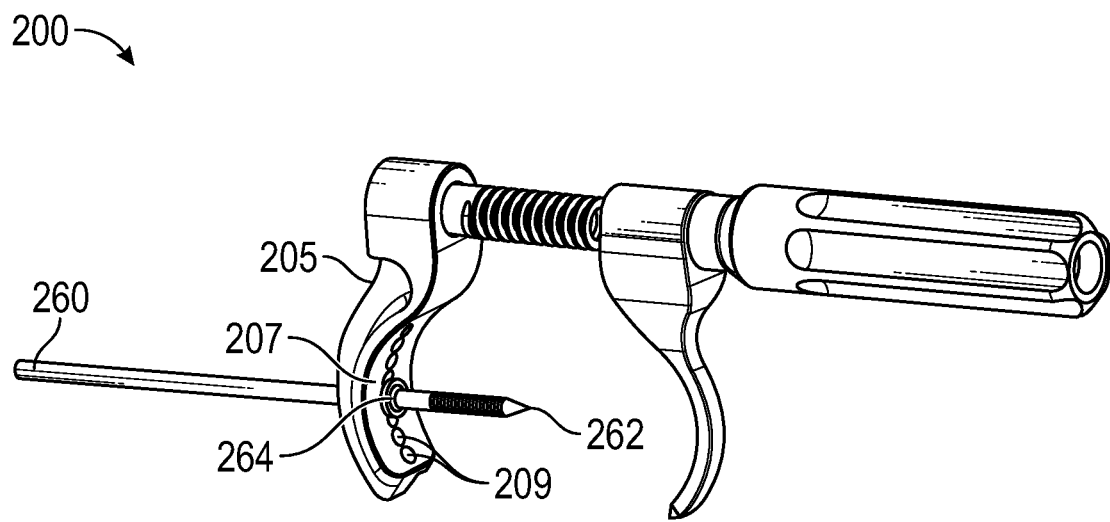

Referring now to FIG. 3H, in some embodiments a shouldered pin 260 may be used in conjunction with the linear reducer 200. Although any type of pin may be used, a shouldered pin 260 may advantageously prevent damage to the skin of the medial side of a foot when the linear reducer 200 is used. The shouldered pin 260 includes a tip 262 which enters the foot and a shoulder 264 which extends radially outward from the sides of the shouldered pin 260. The shoulder 264 is preferably larger than the medial hook pin holes 209 such that the shoulder 264 prevents the shouldered pin 260 from sliding outward through the medial hook pin hole 209. Accordingly, when the shouldered pin 260 is inserted into the medial side of a first metatarsal and the linear reducer 200 is manipulated to reduce the intermetatarsal angle of the foot, the lateral force exerted by the medial hook 205 is transferred to the first metatarsal via the shoulder 264, rather than through the skin along the engagement surface 207, reducing the probability of compression and/or damage to the skin of the foot. In some embodiments, a shouldered pin 260 may be used in conjunction with the quick-release medial hook 235 depicted in FIGS. 3E-3G.

Figure 4A:
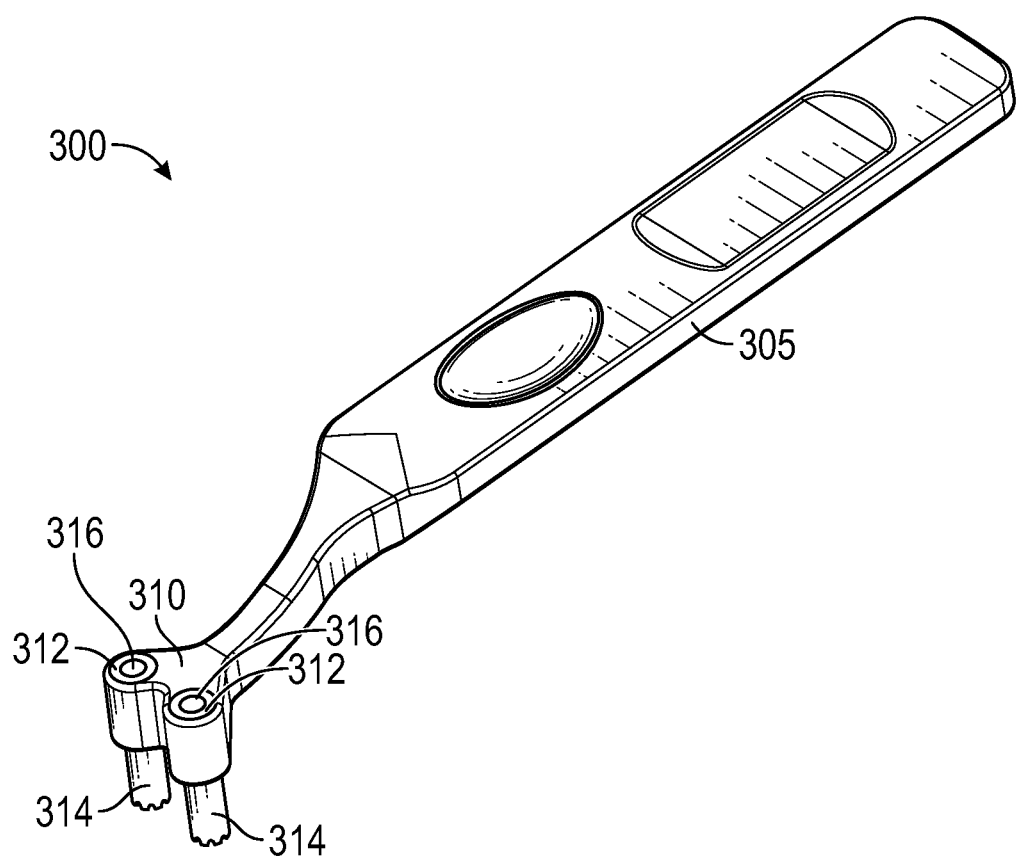
FIGS. 4A and 4B depict an example control handle configured to be used in the Lapidus bunionectomy procedures described herein.
Figure 4B:
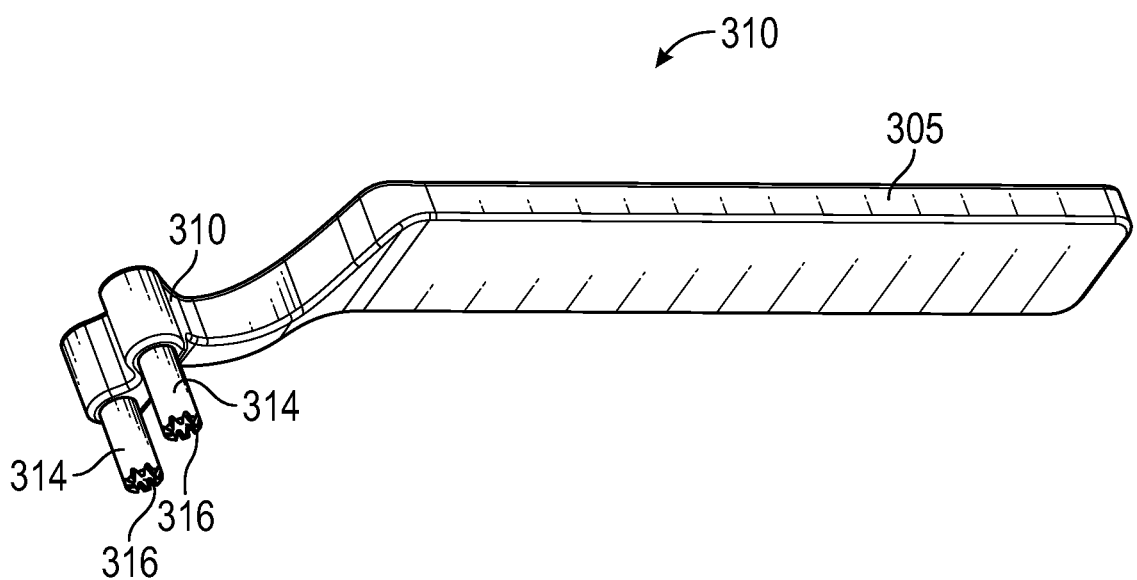

FIGS. 4A and 4B depict an example control handle 300 configured to be used in the Lapidus bunionectomy procedures described herein. As will be described in greater detail with reference to FIGS. 11-14, the linear reducer 200 is suitable for applying correction within the frontal plane or other planes during a Lapidus bunionectomy procedure by rotating the first metatarsal relative to the first cuneiform. The control handle 300 is only one example of a handle that could be attached to the cut guide 100. Those skilled in the art will appreciate that a variety of attachments may be made between a control handle and the cut guide 100 without departing from the scope of the present technology.

The control handle 300 includes a handle 305 and an engagement portion 310 connected to the handle. Apertures 312 within the engagement portion 310 and/or pin guides 314 disposed within the apertures 312 are spaced to receive pins placed within the first metatarsal according to the spacing of the distal pin holes 117 or 170 of the cut guide 100 or the free-hand pin guide 150. The spacing of the apertures 312 also corresponds to the spacing of the proximal pin holes 112 or 165. The spaces 316 within the pin guides 314 are suitably large to receive surgical pins or wires.

Figure 5A:
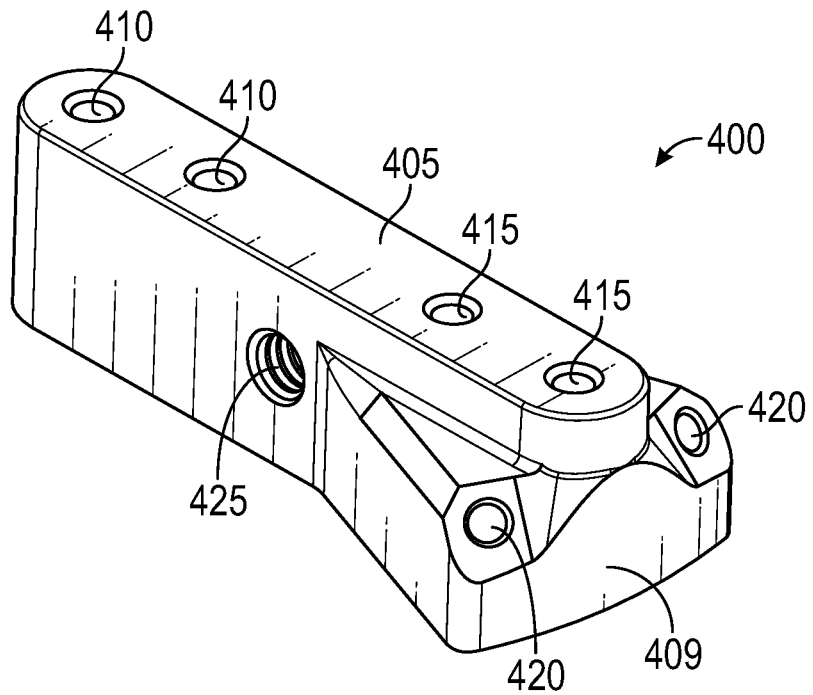
FIGS. 5A-5D depict an example compressor block configured to be used in the Lapidus bunionectomy procedures described herein.
Figure 5B:
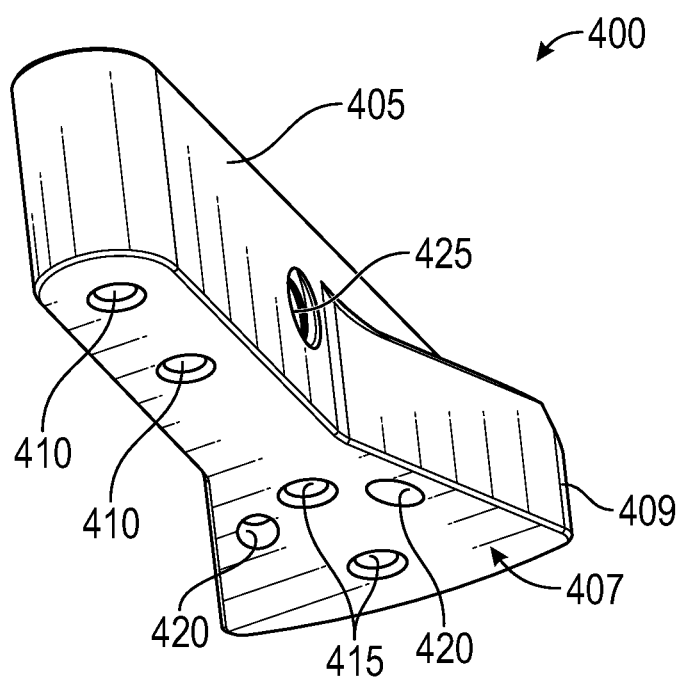
Figure 5C:
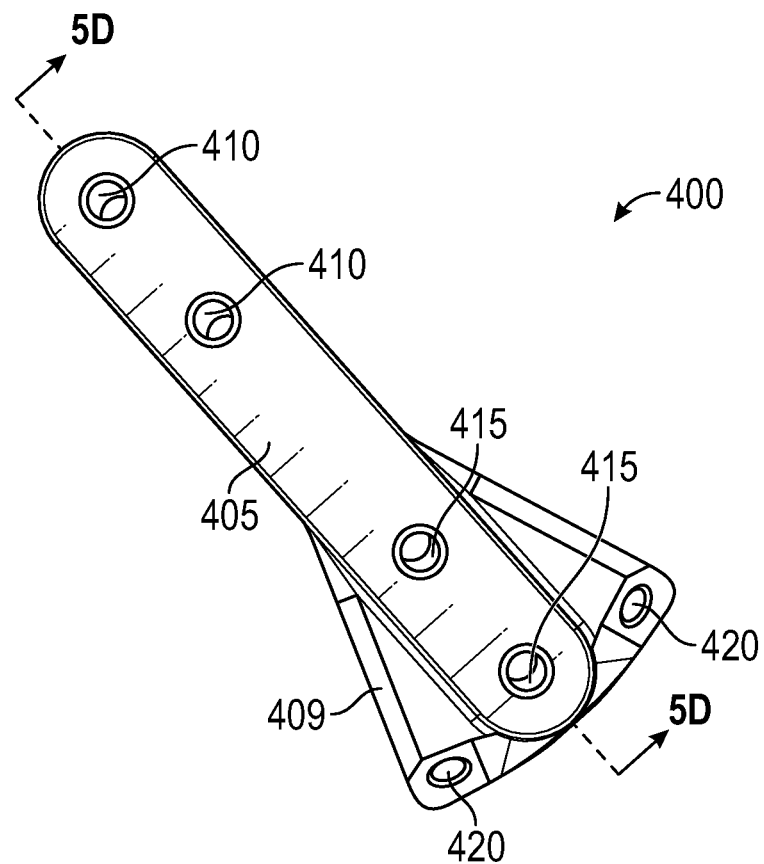
Figure 5D:
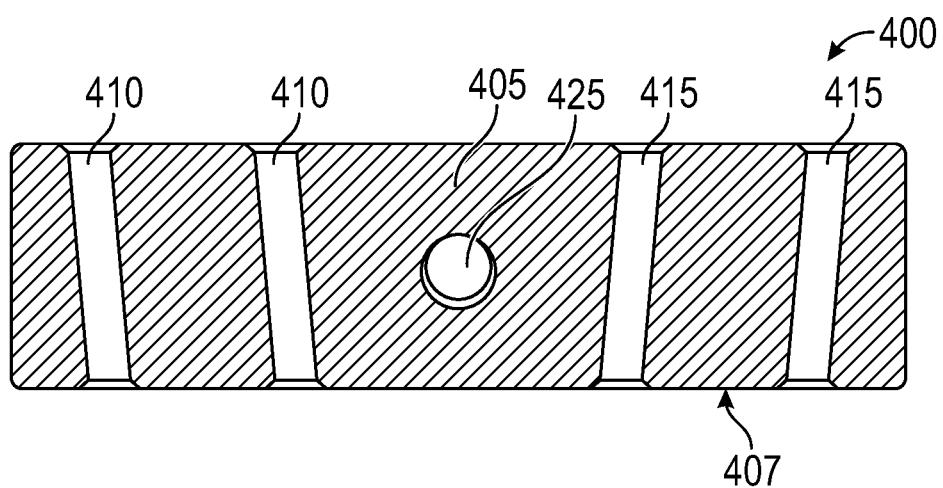

FIGS. 5A-5D depict an example compressor block 400 configured to be used in the Lapidus bunionectomy procedures described herein. FIGS. 5A and 5B are upper and lower perspective views of the compressor block 400, respectively. FIG. 5C is a top plan view of the compressor block 400. FIG. 5D is a cross-sectional side elevation view of the compressor block 400 taken about the line 5D-5D in FIG. 5C. As will be described in greater detail, with reference to FIGS. 16-18, the compression block 400 is configured to assist in compressing and fixing a resected joint that has been free-hand cut or cut using the cut guide 100.

Figure 15:
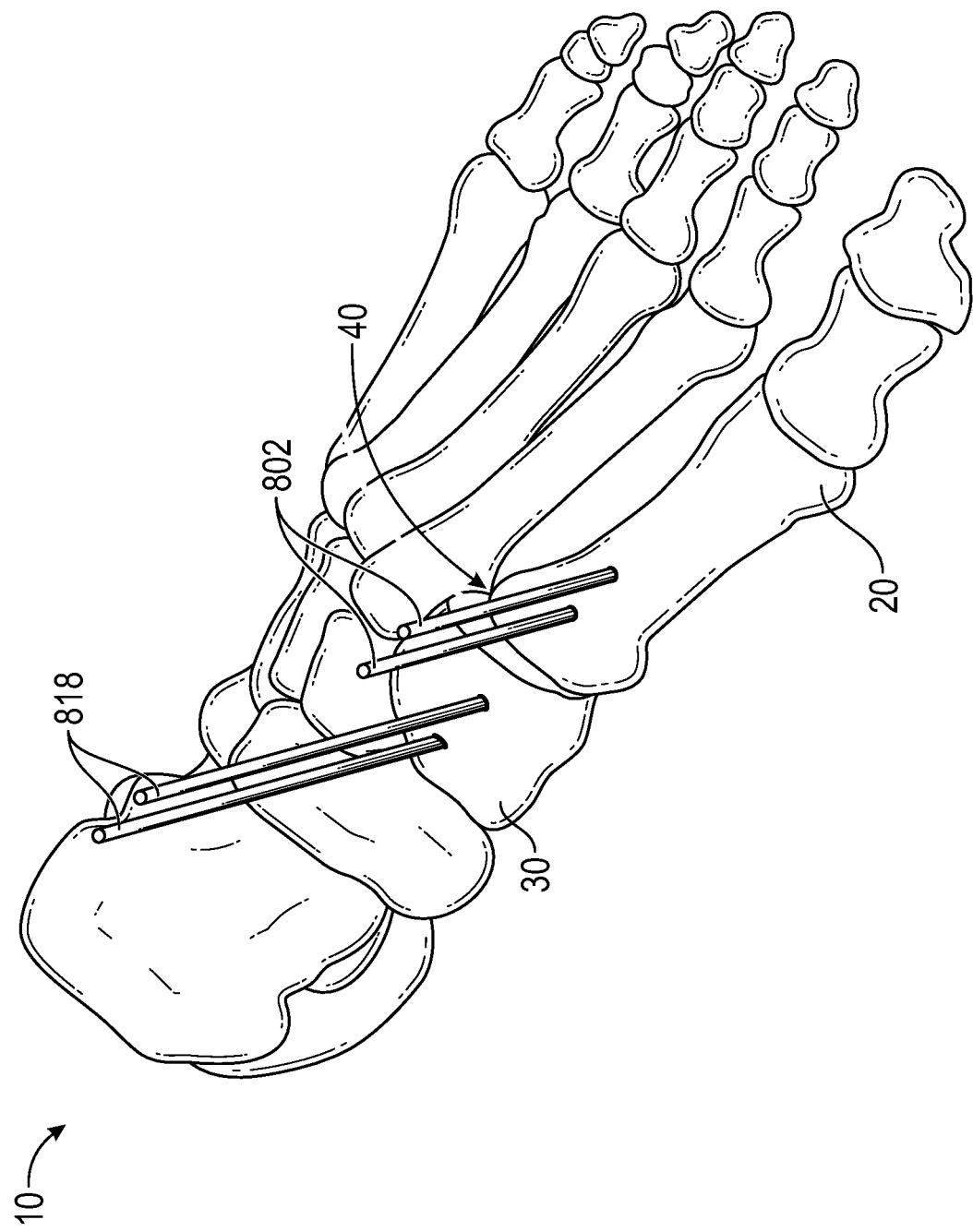
Figure 16:
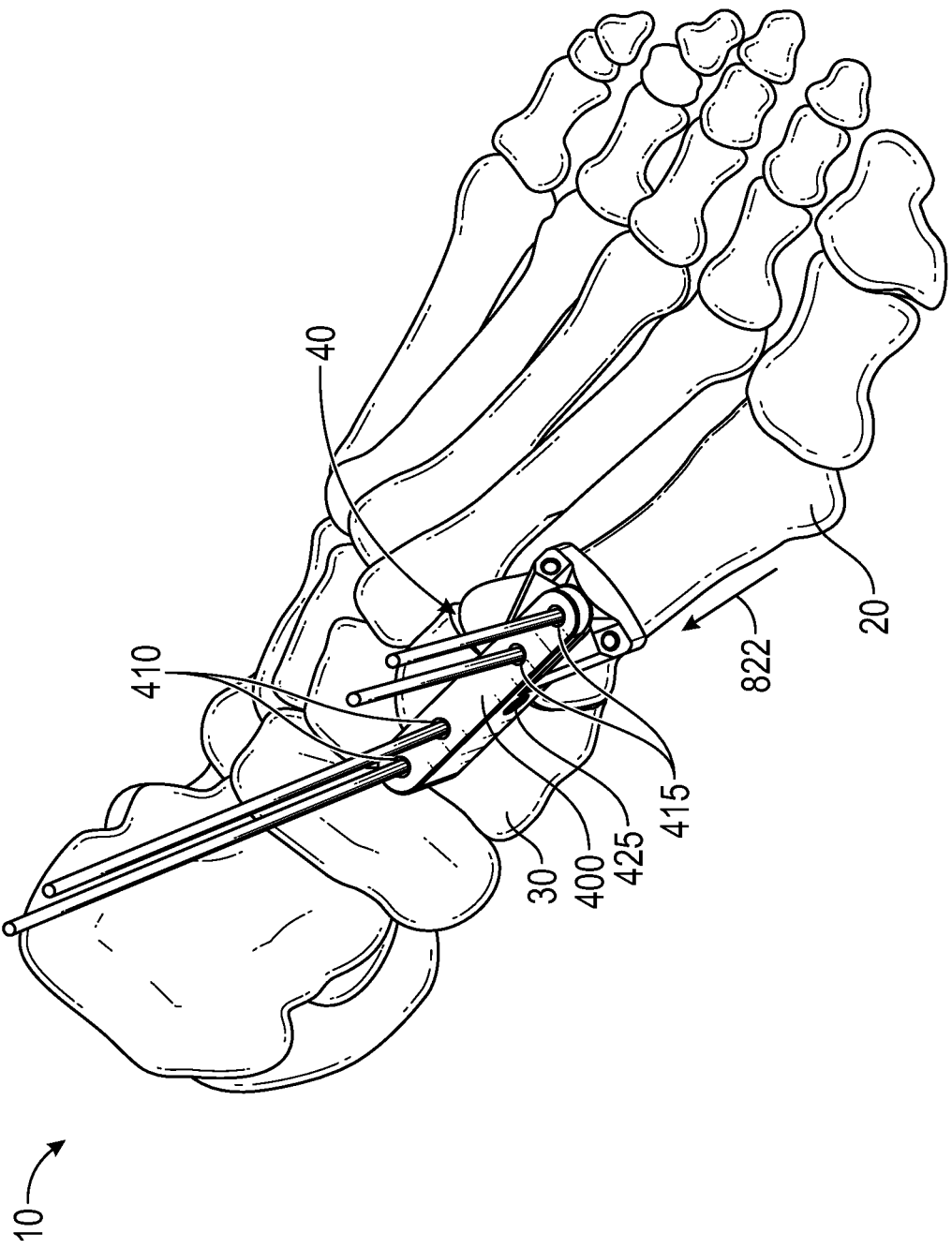

The compressor block 400 includes a body 405 having proximal pin holes 410 and distal pin holes 415 extending therethrough. The proximal pin holes 410 are spaced relative to each other by the same spacing as that of the proximal pin holes 112, 165 of the cut guide 100 and the free-hand pin guide 150. Similarly, the distal pin holes 415 are spaced relative to each other by the same spacing as that of the distal pin holes 117, 170 of the cut guide 100 and the free-hand pin guide 150. However, the proximal pin holes 410 and the distal pin holes 415 are each located closer to the center of the compressor block 400 than the proximal pin holes 112, 165 and the distal pin holes 117, 170 of the cut guide 100 and the free-hand pin guide 150. Additionally, as shown in the cross-sectional view of FIG. 5D, the proximal pin holes 410 and the distal pin holes 415 are not parallel and are disposed at converging angles such that their spacing at the bottom edge 407 of the compressor block 400 is relatively closer. Thus, parallel pins threaded into the proximal apertures 410 and the distal apertures 415 are compressed closer together as the compressor block 400 slides downward over the pins, as shown in FIGS. 15-16. A handle attachment aperture 425, which may be threaded, is provided for attaching a side-mounted handle which may assist the user in sliding the compressor block 400 downward to compress pins or wires passing through the compressor block 400.

Figure 17:
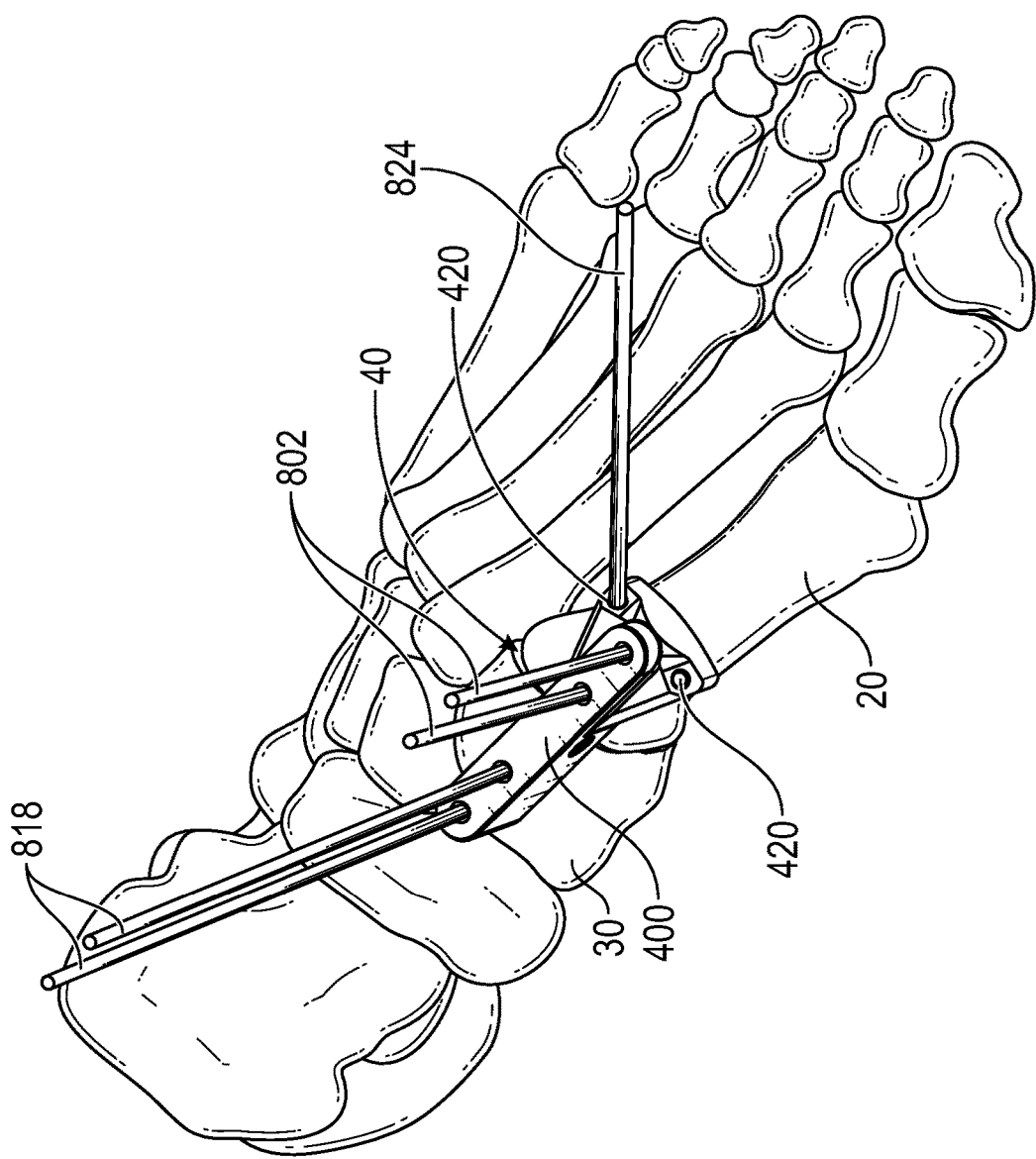
Figure 18:
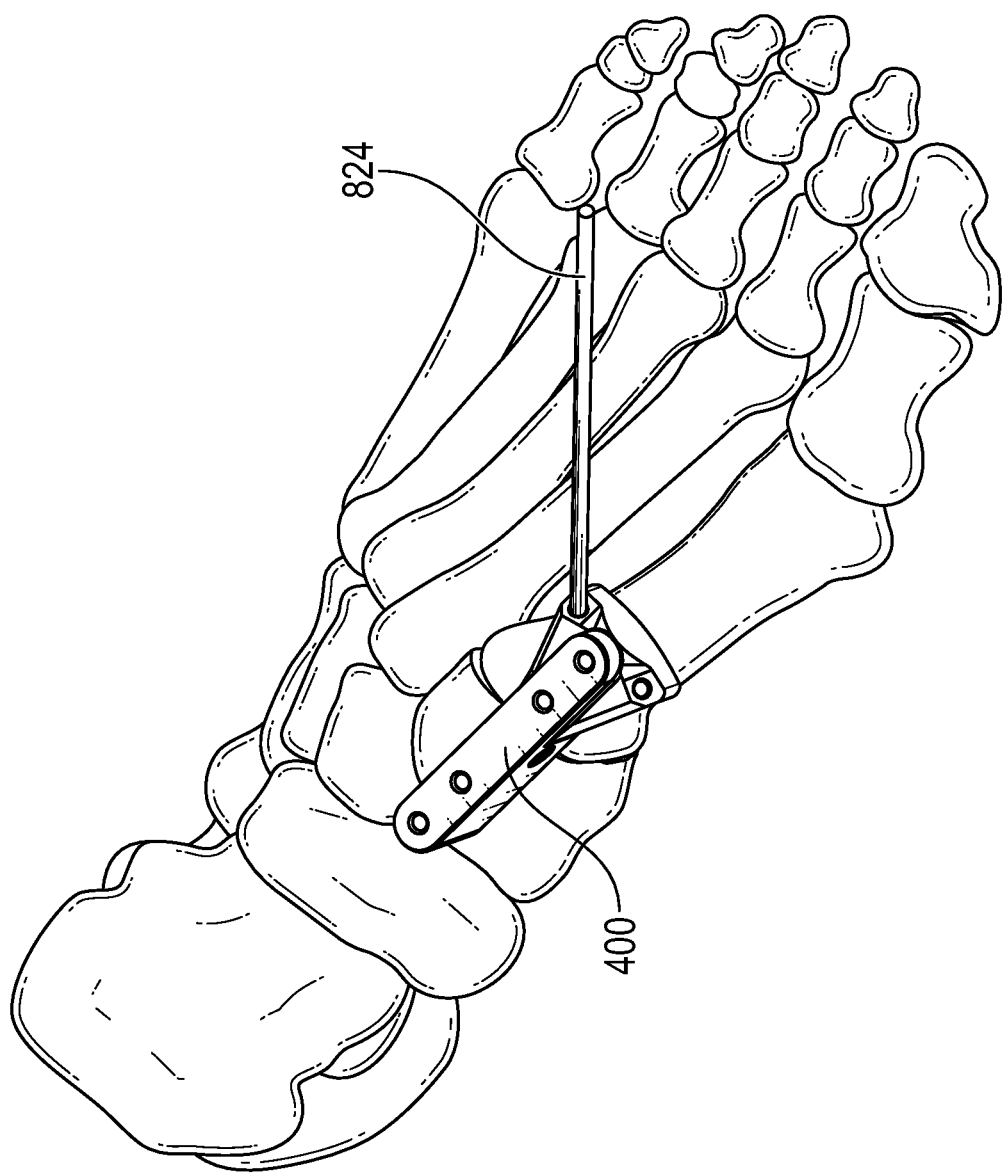

The compressor block 400 further includes widened section 409 containing cross pin holes 420. As shown in FIGS. 5A and 5B, each cross pin hole 420 extends downward and inward from an outer edge of the widened section 409 such that a pin or wire inserted into a cross pin hole 420 exits the bottom edge 407 of the compressor block 400 relatively nearer the centerline of the compressor block 400. As shown in FIGS. 16-18, the cross pin holes 420 are aligned such that, when the compressor block 400 is used in conjunction with the cut guide 100 or free-hand pin guide 150 at the first TMT joint, the compressor block 400 brings the cut faces of the resected first TMT joint into contact with each other and a pin inserted through either cross pin hole 420 will extend at an angle through the interface of the compressed joint to temporarily maintain contact at the joint face until the first cuneiform and the first metatarsal can be fixed by a plate or other fixing component.

FIGS. 6A-6G depict an example bone plate 500 and cross screw 530 configured to be used in the Lapidus bunionectomy procedures described herein. The bone plate 500 and/or the cross screw 530 can be formed of a variety of metals or alloys. For example, the bone plate may be formed of titanium, a shape-memory alloy such as nitinol, or the like.

The bone plate 500 is sized and shaped to be applied across a resected first TMT joint. Accordingly, the bone plate 500 comprises a body 505 including a staple aperture 510, cuneiform screw apertures 515, a metatarsal screw aperture 520, and a cross screw aperture 525. The staple aperture 510 includes two holes 512 sized and shaped to accommodate the two legs of a bone staple such that one of the legs is seated within the first cuneiform near the cuneiform screw apertures 515 and the other leg is seated within the first metatarsal near the metatarsal screw aperture 520 and the cross screw aperture 525.

The staple aperture 510 and each of the screw apertures 515, 520, 525 is shaped to include a countersink to reduce motion of staples and/or screws seated therein. In addition, the countersinks may allow a staple or screw applied therein to not extend significantly above the outer surface of the body 505 of the bone plate 500. Due to the angle at which a cross screw must be applied in the cross screw aperture 525, the cross screw aperture 525 has an elliptical shape when viewed perpendicular to the bone plate 500 (e.g., corresponding to a cylindrical profile along a screw path through the cross screw aperture 525) and includes a shelf 527 occupying approximately one half of the perimeter of the cross screw aperture 525. The shelf 527 is shaped to engage with the head of a cross screw when the cross screw is inserted at a pre-drilled angle, such that the cross screw securely engages the bone plate 500 and seats within the countersink.

Figure 6A:
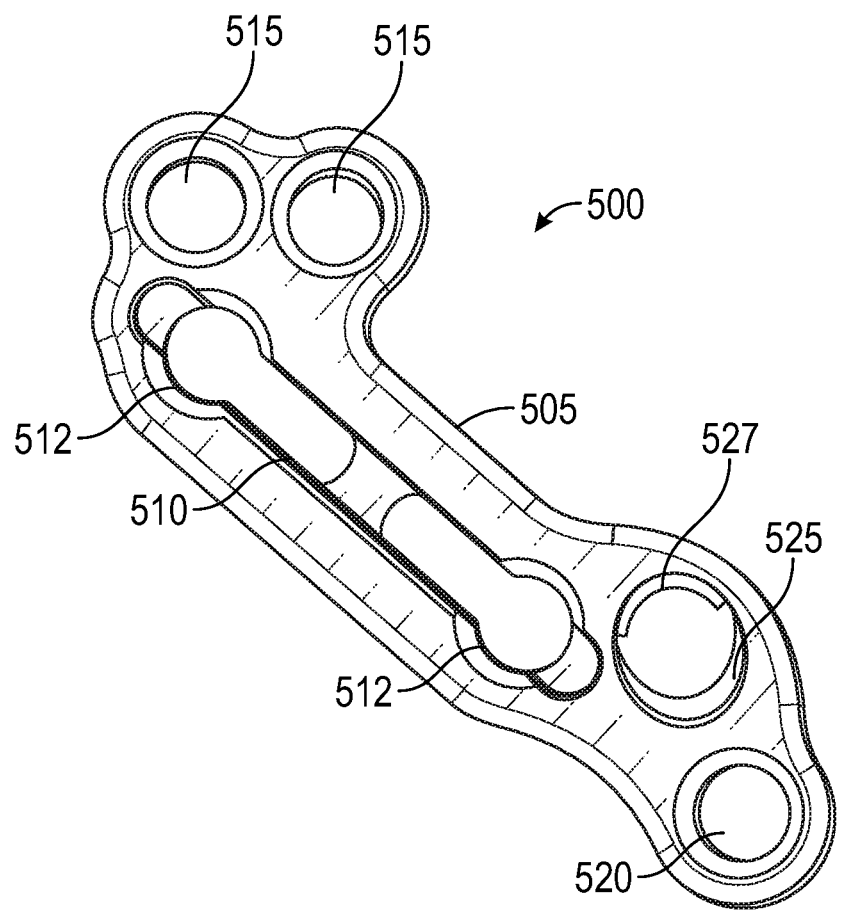
FIGS. 6A-6G depict an example bone plate and cross screw configured to be used in the Lapidus bunionectomy procedures described herein.
Figure 6B:
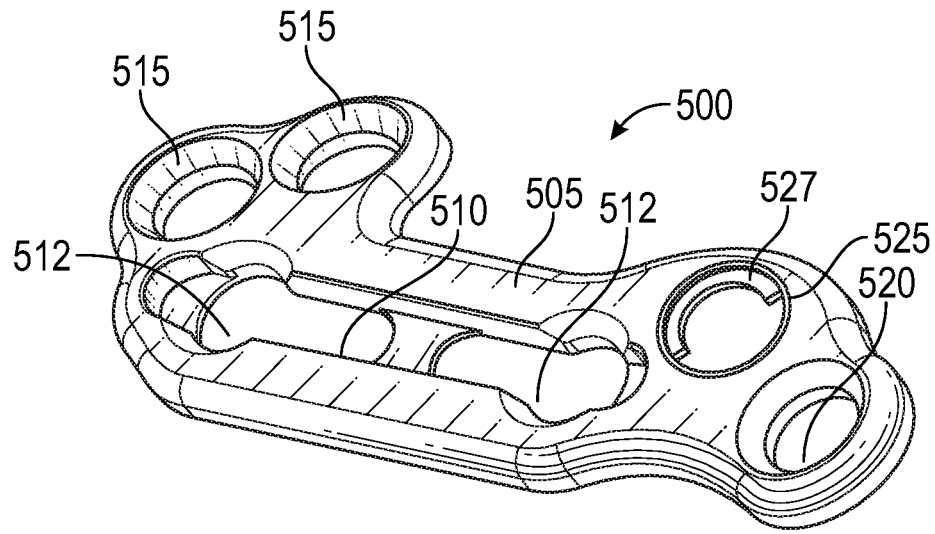
Figure 6C:
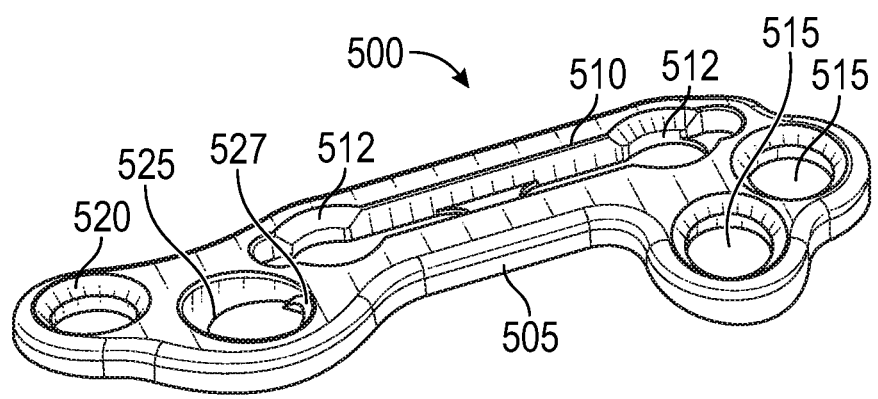
Figure 6D:
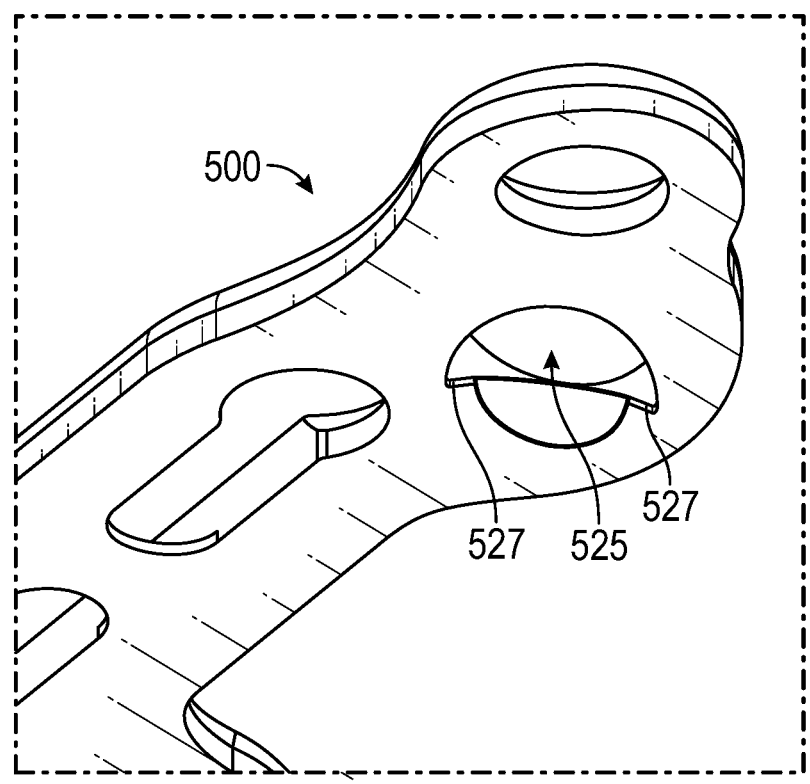
Figure 6E:
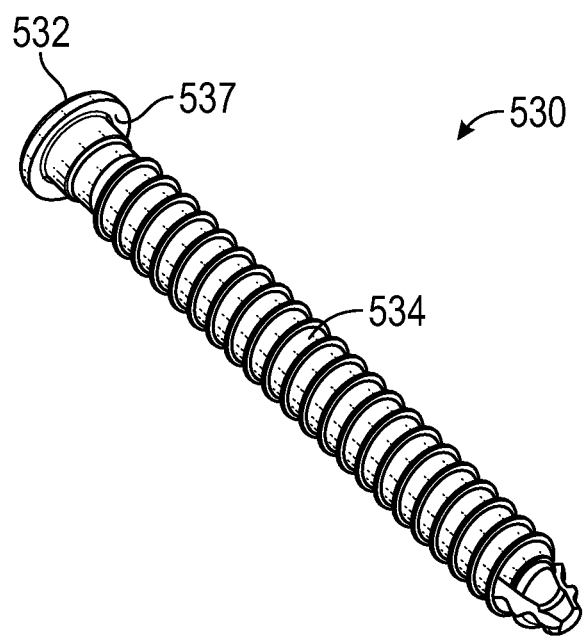
Figure 6F:
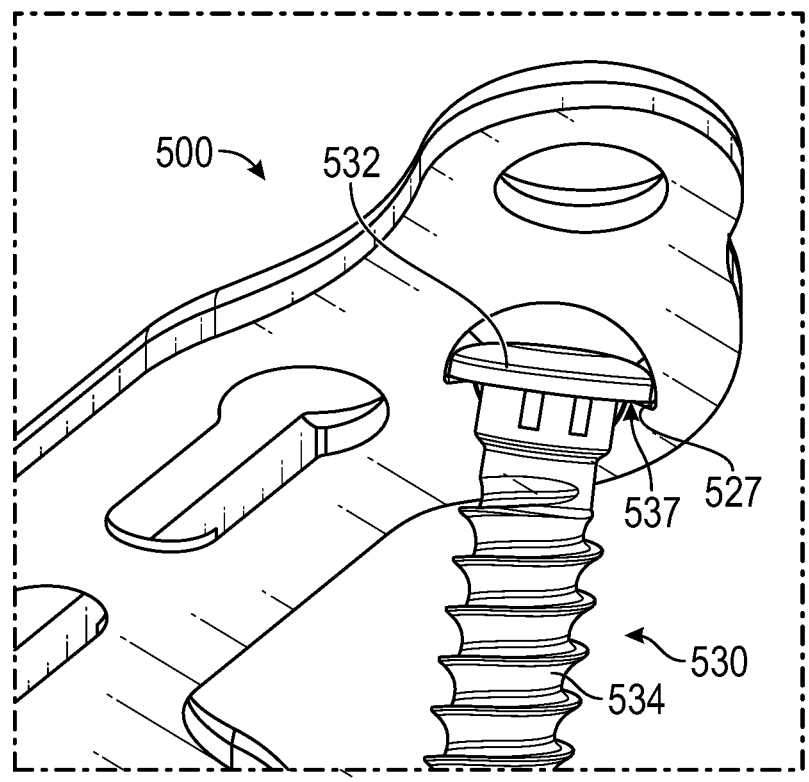
Figure 6G:
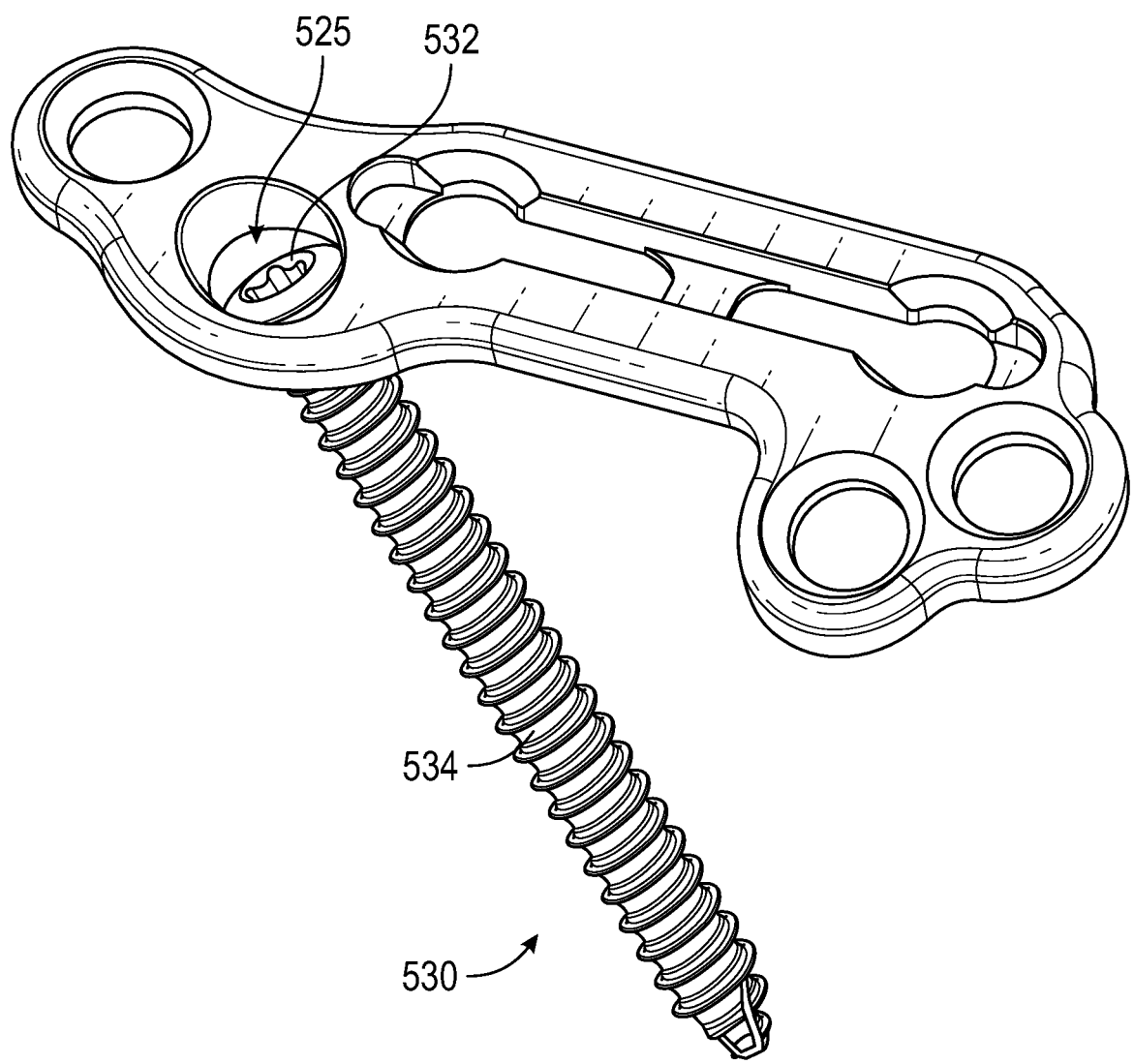

FIG. 6D is an expanded partial view of the bone plate 500, illustrating in detail the cross screw aperture 525 and the shelf 527. FIG. 6E illustrates an example cross screw 530 configured to be seated within the cross screw aperture 525, including a head 532 and a threaded shaft 534. As shown in FIG. 6D, which is taken perpendicular to an axis of a cross screw path, the shelf 527 can be canted or tapered such that an inner edge of the shelf 527 is higher relative to an outer edge where the shelf 527 meets the interior wall of the cross screw aperture 525. As shown in FIG. 6E, the head 532 of the cross screw 530 has an undercut shelf 537. The shelf 537 is tapered downward as the diameter increases in this embodiment. Accordingly, as shown in FIGS. 6F and 6G, when the cross screw 530 is inserted through the cross screw aperture 525, the undercut shelf 537 of the head 532 of the cross screw 530 engages with the upwardly tapering shelf 527 of the bone plate 500 such that the bone screw 530 seats at the desired angle within the bone.

Figure 7A:
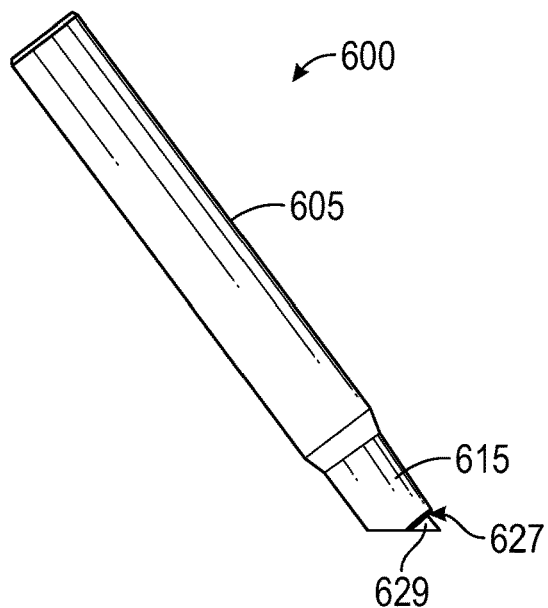
FIGS. 7A-7C depict an example fixed-angle cross screw drill guide configured to be used in the Lapidus bunionectomy procedures described herein.
Figure 7B:
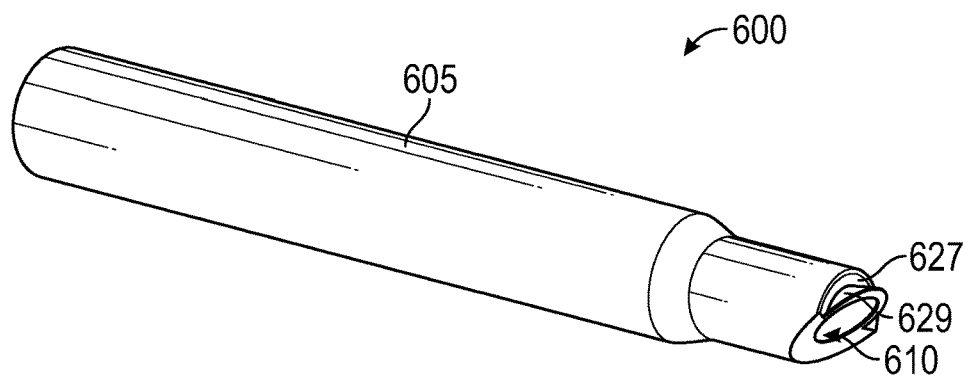
Figure 7C:
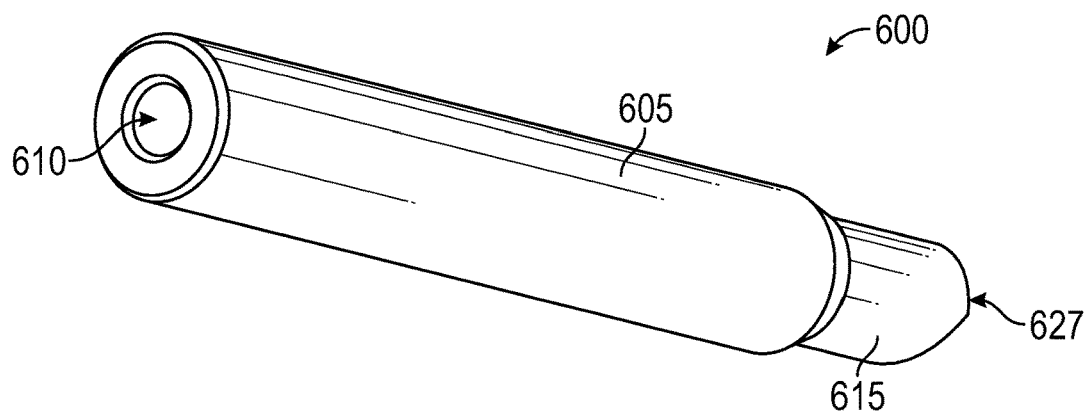
Figure 7D:
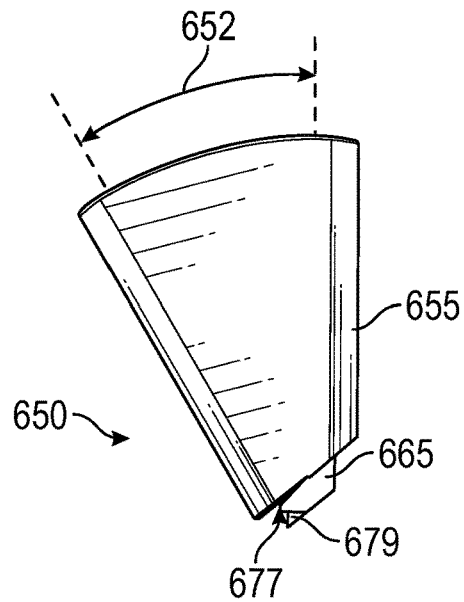
FIGS. 7D-7F depict an example variable-angle cross screw drill guide configured to be used in the Lapidus bunionectomy procedures described herein.
Figure 7E:
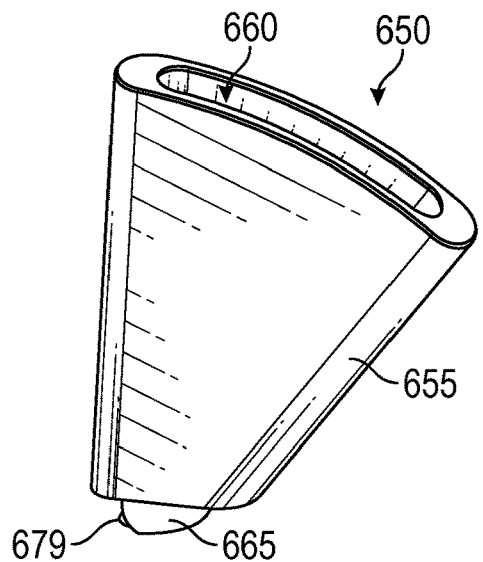
Figure 7F:
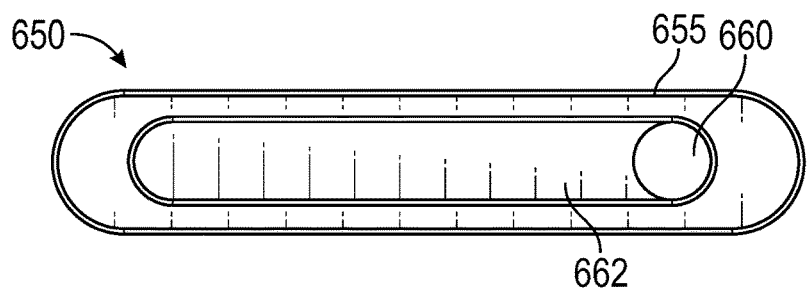

FIGS. 7A-7F depict example cross screw drill guides configured to be used in conjunction with the bone plate 500 when applying the cross screw through the cross screw aperture 525. FIGS. 7A-7C depict an example fixed-angle cross screw drill guide 600. FIGS. 7D-7F depict an example variable-angle cross screw drill guide 650 which allows a surgeon to select one of a range of angles for insertion of the cross screw.

The fixed-angle cross screw drill guide 600 includes a body 605 and a tip 615. A lengthwise aperture 610 extends through the full length of the body 605. The diameter of the lengthwise aperture 610 may be selected such that a drill bit, suitably sized to drill a pilot hole for a cross screw, can fit through the lengthwise aperture 610. In some embodiments, the diameter of the lengthwise aperture 610 may be selected such that a k-wire or other guide structure can fit through the lengthwise aperture 610, such that the guide may be removed and a cannulated drill bit may be used to drill a pilot hole. The tip 615 includes a shelf engagement surface 627 and a toe 629. The toe 629 and the shelf engagement surface 627 are shaped such that the toe 629 can be seated within the cross screw aperture 525 with the shelf engagement surface 627 seated against the shelf 527 of the cross screw aperture 525. The elliptical shape of the cross screw aperture 525 defines a single stable orientation for seating the tip 615 of the fixed-angle cross screw drill guide 600 therein. The fixed-angle cross screw drill guide 600 facilitates consistent and reproducible application of a cross screw at a predetermined suitable angle to prevent bunion recurrence. Additionally, the fixed-angle cross screw drill guide 600 can force the entry of the drill bit into bone at a location concentric with the radius of curvature of the shelf 527 of the bone plate 500 (e.g., because a screw may still be able to pass through the bone plate 500 even if the hole is incorrectly drilled). Moreover, the fixed-angle cross screw drill guide 600 establishes the drill bit at an angle that prevents the cross screw from interfering with the staple leg, prevents the cross screw from crossing the TMT joint, and directs the cross screw toward the base of the second metatarsal or the second cuneiform.

The variable-angle cross screw drill guide 650 similarly includes a body 655 and a tip 665, as well as an aperture 660 extending through the body 655. The tip 665 has the same shape as the tip 615 of the fixed-angle cross screw drill guide 600, including a shelf engagement surface 677 and a toe 679, such that the elliptical shape of the cross screw aperture 525 similarly defines a single stable orientation for seating the tip 665 of the variable-angle cross screw drill guide 650 therein. The variable-angle cross screw drill guide 650 has a generally wedge-shaped body 655 surrounding a wedge-shaped slot 662 in communication with the aperture 660. The wedge-shaped slot 662 accommodates a range 652 of drilling angles whose paths pass through the aperture 660. Thus, while the elliptical shape of the cross screw aperture 525 defines a single seating orientation of the variable-angle cross screw drill guide 650, the wedge-shaped slot 662 allows the surgeon to select a variety of angles within a predetermined plane. The available drilling paths can range from a first extreme path which is perpendicular or nearly perpendicular relative to the bone plate 500, to a second extreme path at a smaller angle relative to the bone plate 500. Depending on the geometry of the bone structure of an individual foot, the variable-angle cross screw drill guide 650 can allow a surgeon to select a cross screw trajectory, for example, to enter the second metatarsal or the second cuneiform as desired.

With reference to FIGS. 8-24, an example Lapidus bunionectomy using certain devices disclosed herein will be described. Although the procedure of FIGS. 8-24 illustrates a particular implementation of a Lapidus bunionectomy using a specific subset of the devices disclosed herein, it will be understood that the components and steps illustrated and described with reference to FIGS. 8-24 may equally be applied in different sequences and/or with different combinations of components to correct a bunion.

Figure 8:
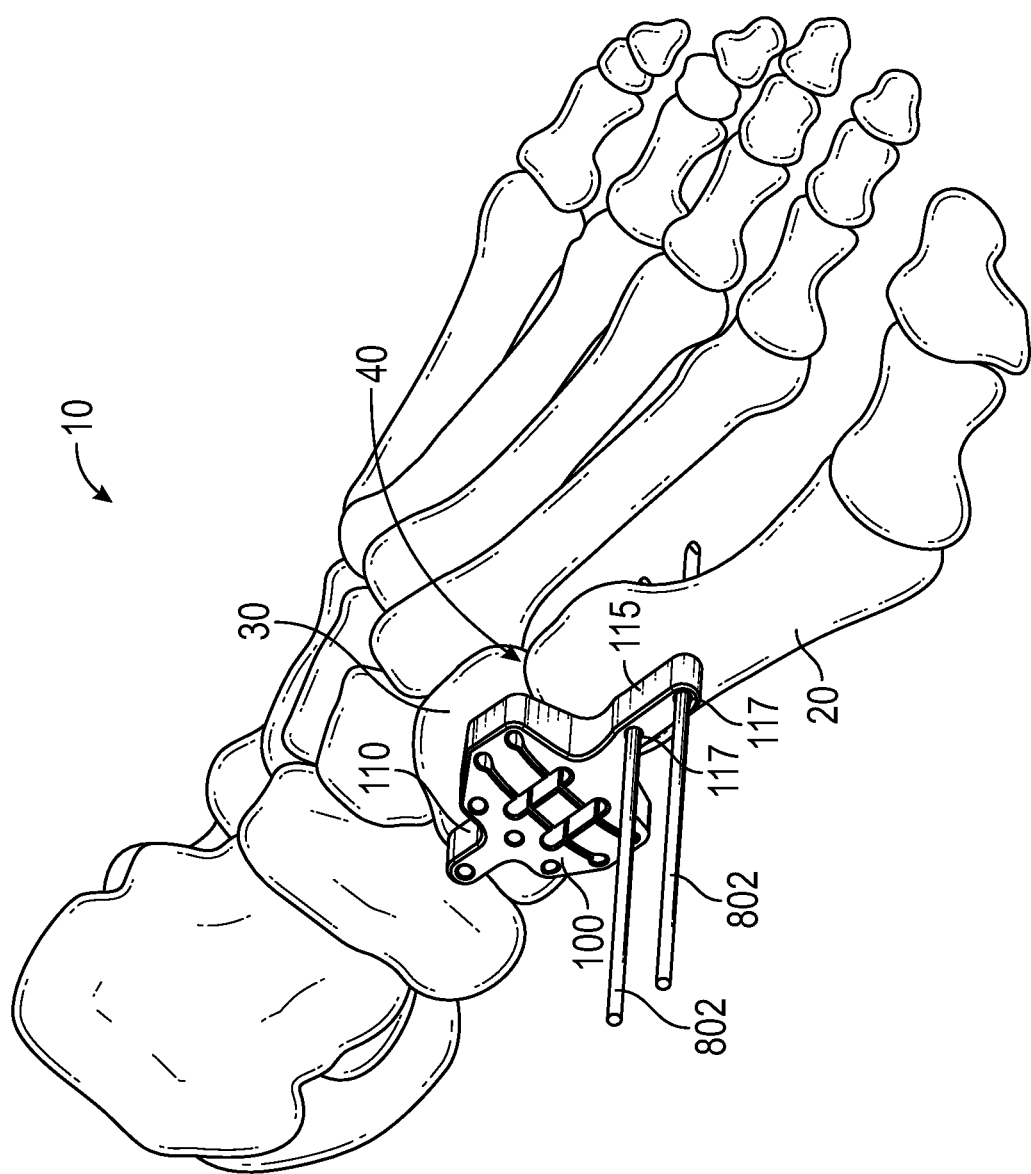
FIGS. 8-24 are perspective views of the bones of a foot, sequentially illustrating an example Lapidus bunionectomy procedure performed using the example bunionectomy devices disclosed herein.

FIGS. 8-24 depict the bones of a foot 10 initially having a bunion. Similar to the foot 10 of FIG. 1, the foot 10 includes a first metatarsal 20 that is angled and rotated relative to the first cuneiform 30 at the first TMT joint 40 such that the big toe has an undesirable medial protrusion and an increased intermetatarsal angle. As shown in FIG. 8, the procedure may begin by placing and temporarily securing the cut guide 100 of FIGS. 2A-2D. Prior to placing the cut guide, the surgeon may prepare the first TMT joint 40 by making an incision such as a dorsomedial incisions to expose the first TMT joint 40 and excising soft tissue around the joint, such as the joint capsule or other soft tissue, to expose the first TMT joint 40 and create a space in which the paddle 120 (FIGS. 2A-2D) of the cut guide 100 can be seated.

Once the joint has been prepared, the cut guide 100 is placed by seating the paddle 120 (not visible in FIG. 8) within the first TMT joint 40 such that proximal extension 110 sits adjacent to or against the first cuneiform 30 and the distal extension 115 sits adjacent to or against the first metatarsal 20. The paddle 120 is inserted into the first TMT joint 40 such that the cut guide 100 is oriented along the axis of the first metatarsal 20. The alignment of the cut guide 100 may be confirmed under fluoroscopy or other suitable imaging technique before proceeding.

When the cut guide 100 has been placed and is suitably aligned, the cut guide 100 is temporarily secured relative to the first metatarsal 20 by inserting two metatarsal pins 802 or wires through the distal pin holes 117 of the distal extension 115 and into or through the first metatarsal 20. The metatarsal pins 802 or wires, as well as any of the other pins or wires described in the following description, may be, for example, a Kirschner wire ("K-wire"), or any other suitable type of wire or pin that can be placed into the bone to secure the cut guide 100.

Figure 9:
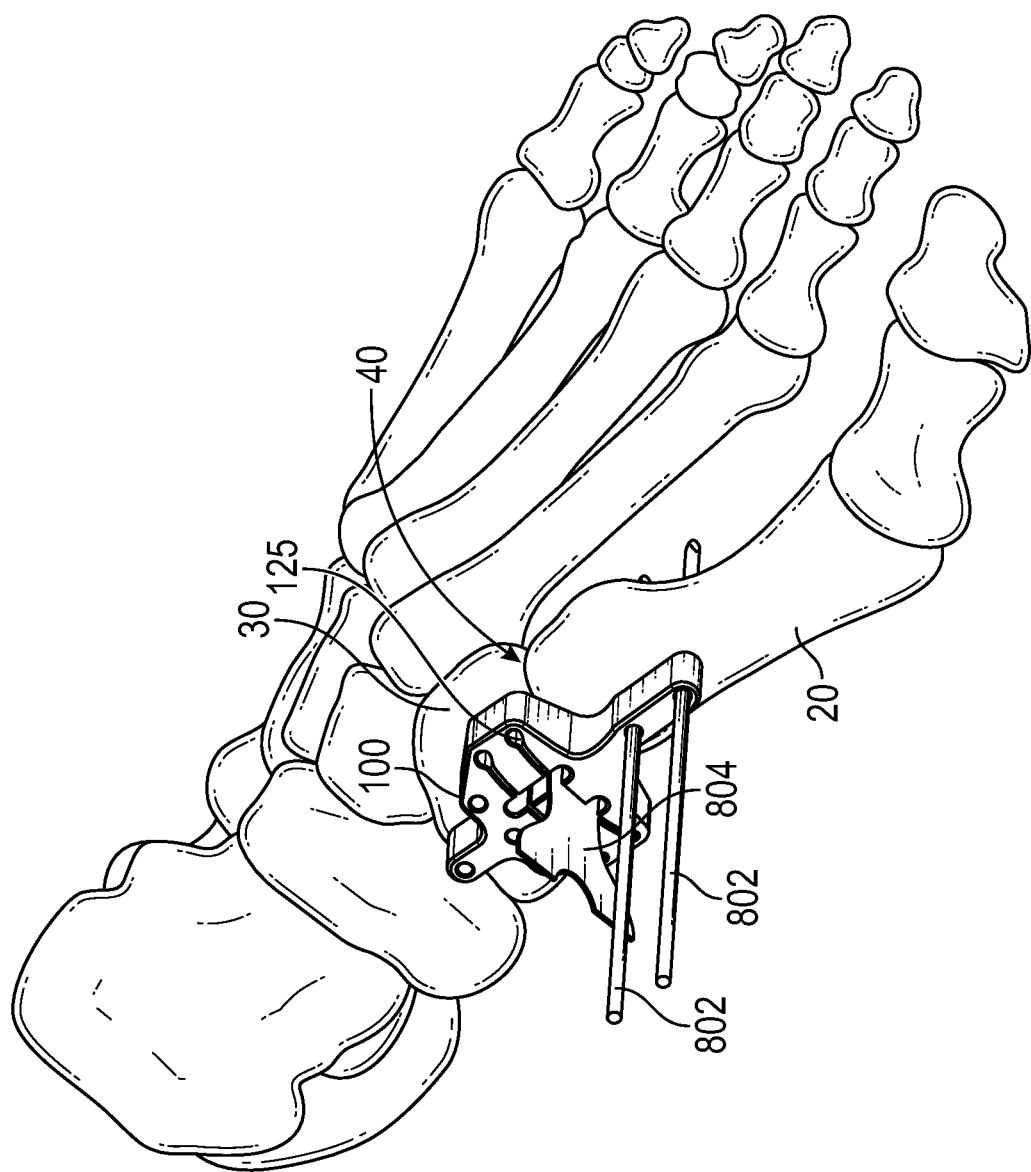

Continuing to FIG. 9, once the metatarsal pins 802 or wires are inserted, the base of the first metatarsal 20 is cut using a saw blade 804 inserted through the distal slot 125 of the cut guide 100.

Figure 10:
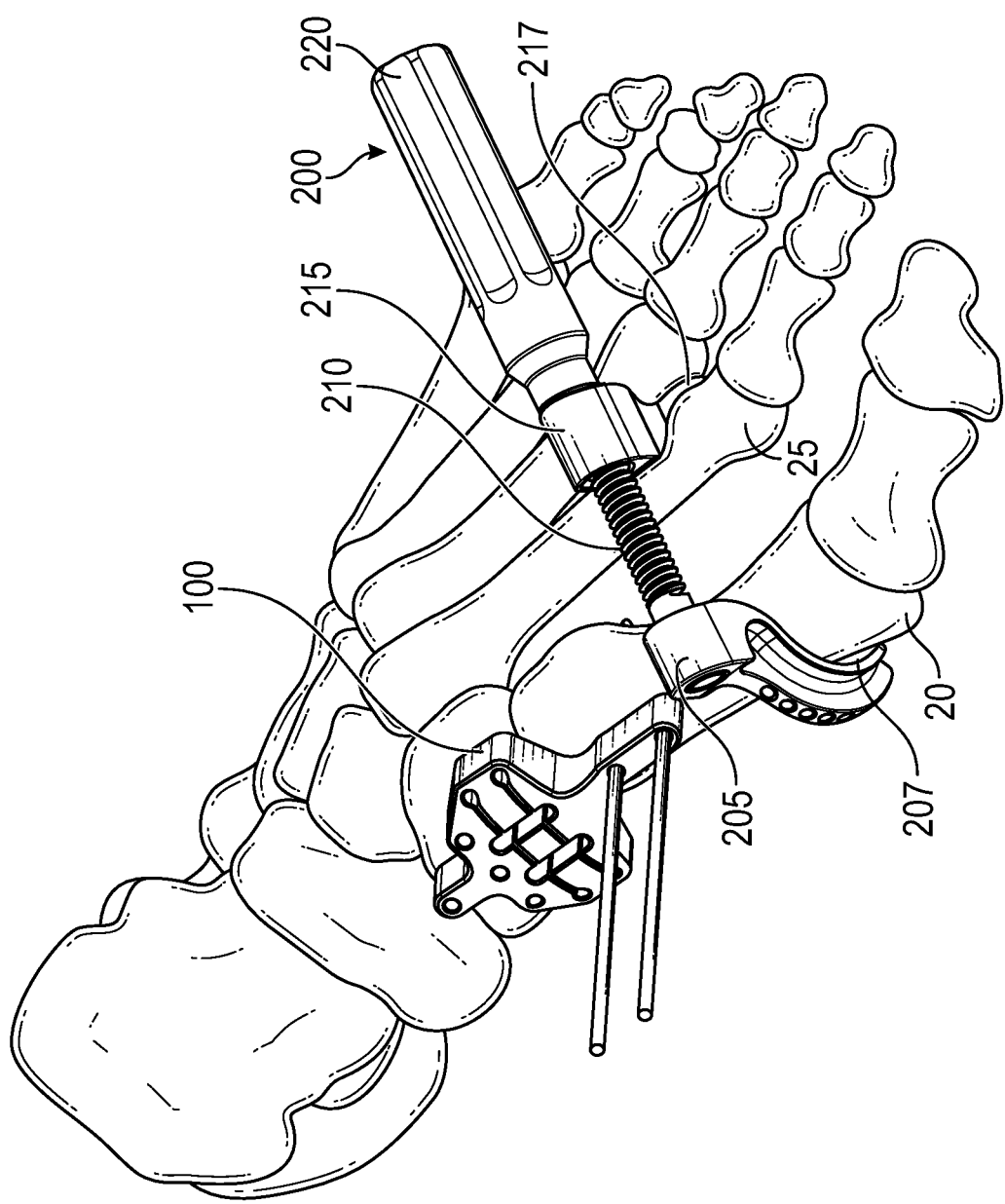

With reference to FIG. 10, a linear reducer 200 may be provisionally placed around the first metatarsal 20 and the second metatarsal 25. In some embodiments, an incision is made lateral of the second metatarsal 25 between the second and third toes to accommodate insertion of the lateral hook 215 such that the engagement surface 217 contacts the lateral side of the second metatarsal 25. The engagement surface 207 of the medial hook 205 is placed against the medial side of the first metatarsal 20, and the handle 220 of the linear reducer 200 may be turned clockwise relative to the threaded shaft 210 until the handle 220 contacts the lateral fork 215. The initial placement of the linear reducer 200 may be a provisional placement, without initially inserting any pins through the medial fork 205.

Figure 11:
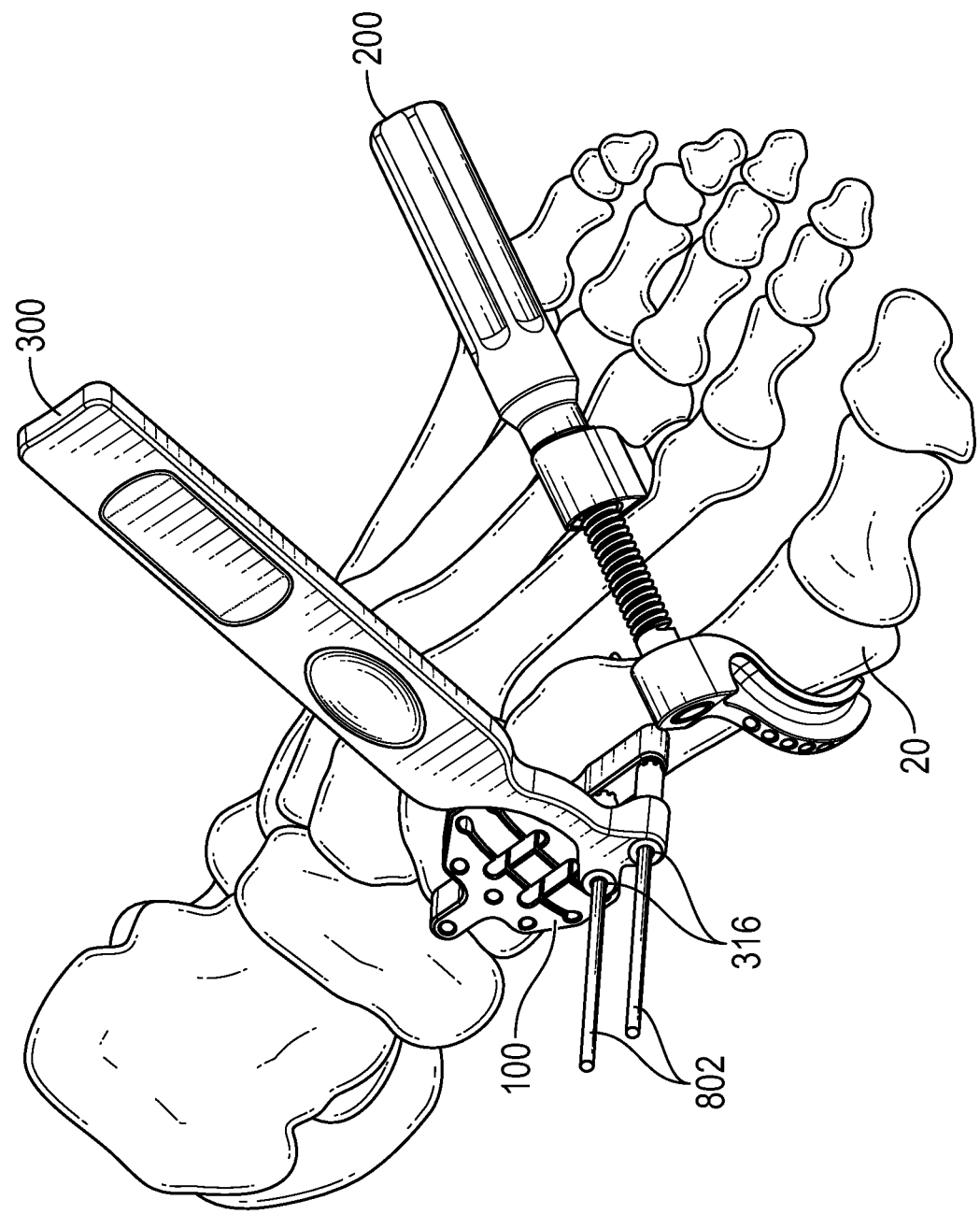
Figure 12:
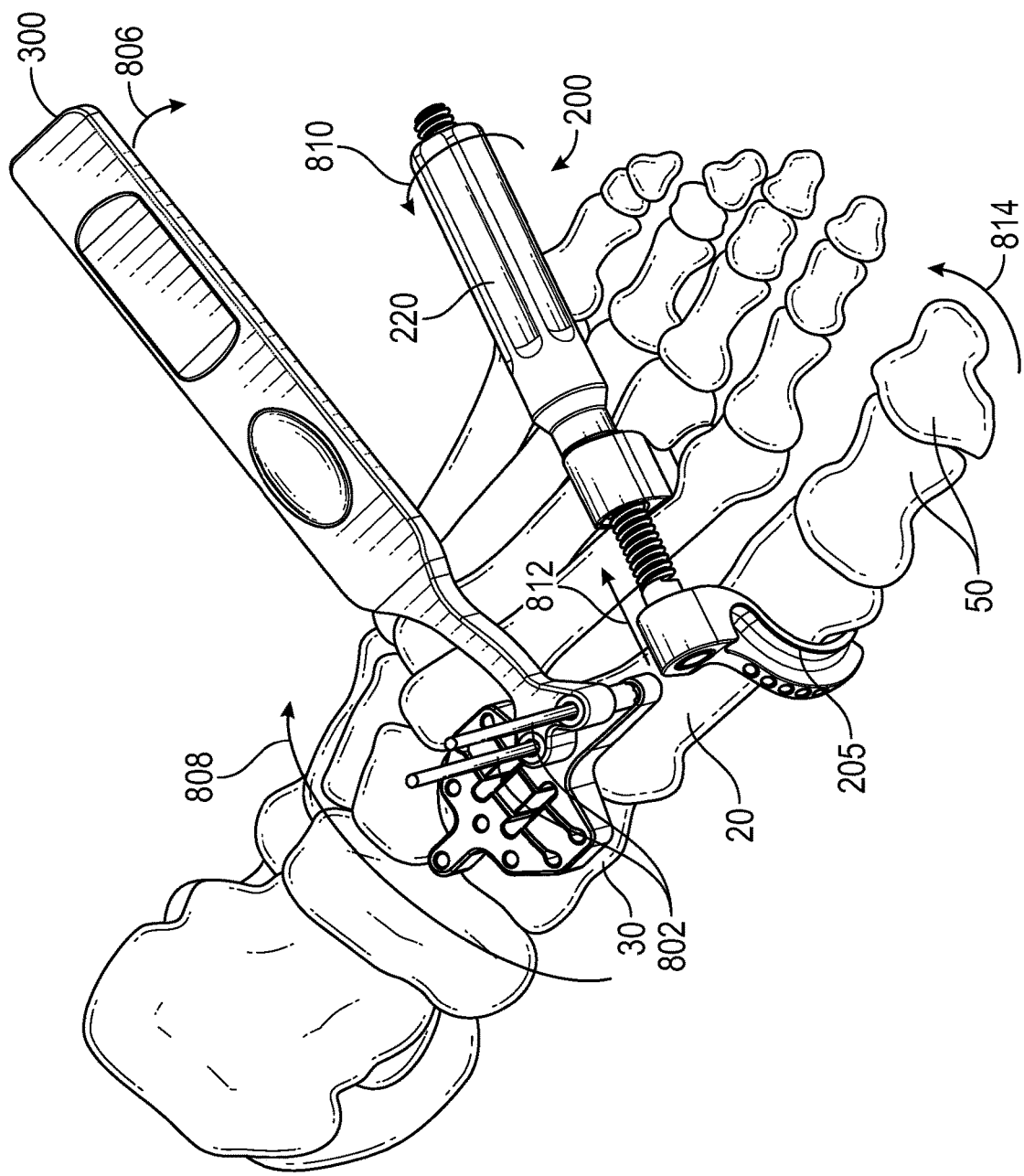

Continuing to FIG. 11, a control handle 300 may further be placed by inserting the metatarsal pins 802 through the spaces 316 within the pin guides 314 of the control handle 300. With reference to FIG. 12, the control handle 300 may then be rotated within the frontal plane to correct for rotation about the axis of the first metatarsal 20. For example, when a clockwise rotation 806 imparted to the control handle 300, the torque applied to the control handle 300 is transferred via the metatarsal pins 802 such that the first metatarsal and the phalanges 50 of the big toe are rotated clockwise 808. Additionally, any necessary adjustment of the joint within the sagittal plane may be applied manually at this time. In some embodiments, other corrections, such as application of torque in the transverse plane to reduce the intermetatarsal angle, could also be applied using the control handle 300. When the frontal plane and sagittal plane have been suitably corrected using the control handle 300, the surgeon may then proceed to adjust the position of the first metatarsal 20 in the transverse plane.

Figure 13:
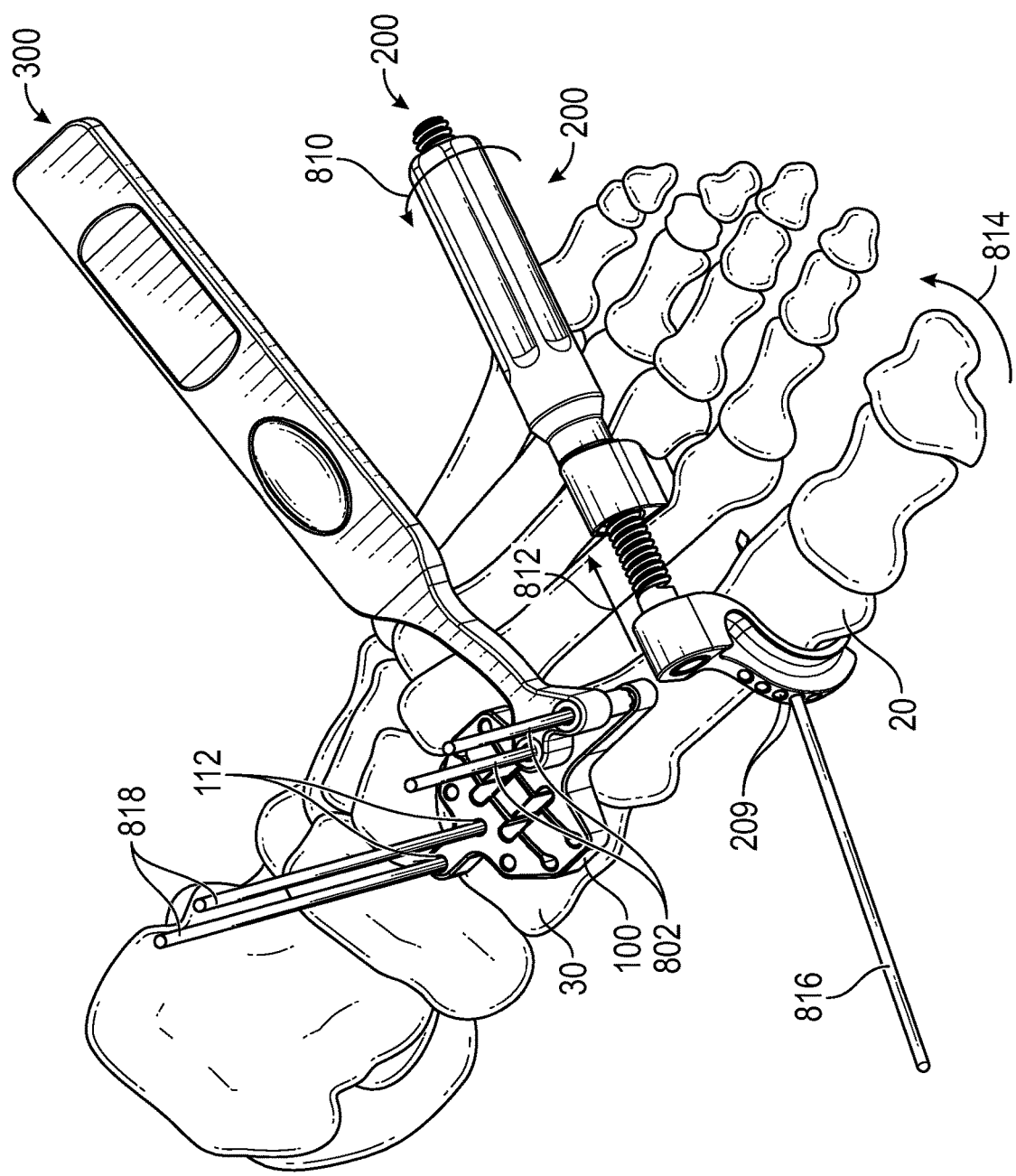

Referring jointly to FIGS. 12 and 13, the transverse plane may be corrected using the linear reducer 200. In some implementations, a medial hook pin 816 is inserted through one of the medial hook pin holes 209 and into or through the first metatarsal 20 to fix the rotational position of the first metatarsal 20 in the frontal plane (e.g., locking in the frontal plane correction previously applied using the control handle 300). The medial hook pin may be a shouldered pin, such that lateral pressure exerted by the medial hook 205 is applied directly to the first metatarsal 20 through the pin shoulder rather than being applied through the skin along the engagement surface 207 of the medial hook.

With or without insertion of a medial hook pin 816, a transverse plane correction may be applied by turning the handle 220 of the linear reducer 200. For example, a clockwise rotation 810 of the handle 220 reduces the distance along the threaded shaft between the medial fork 205 and the lateral fork 215, causing the medial fork 205 to move laterally along direction 812 relative to the lateral fork 215. As a result, the medial fork 205 applies a lateral force to the first metatarsal 20 in the transverse plane, causing a corresponding lateral movement 814 of the first metatarsal 20 within the transverse plane.

At this stage, the misalignment of the first TMT joint 40 has been addressed. With continued reference to FIG. 13, two cuneiform pins 818 or wires are inserted through the proximal pin holes 112 of the cut guide and into or through the first cuneiform 30. The cuneiform pins 818 or wires temporarily secure the cut guide 100 relative to the first cuneiform 30. At this point, the four pins 802 and 814 form an array that establishes and/or locks the surgeon's desired correction.

Figure 14:
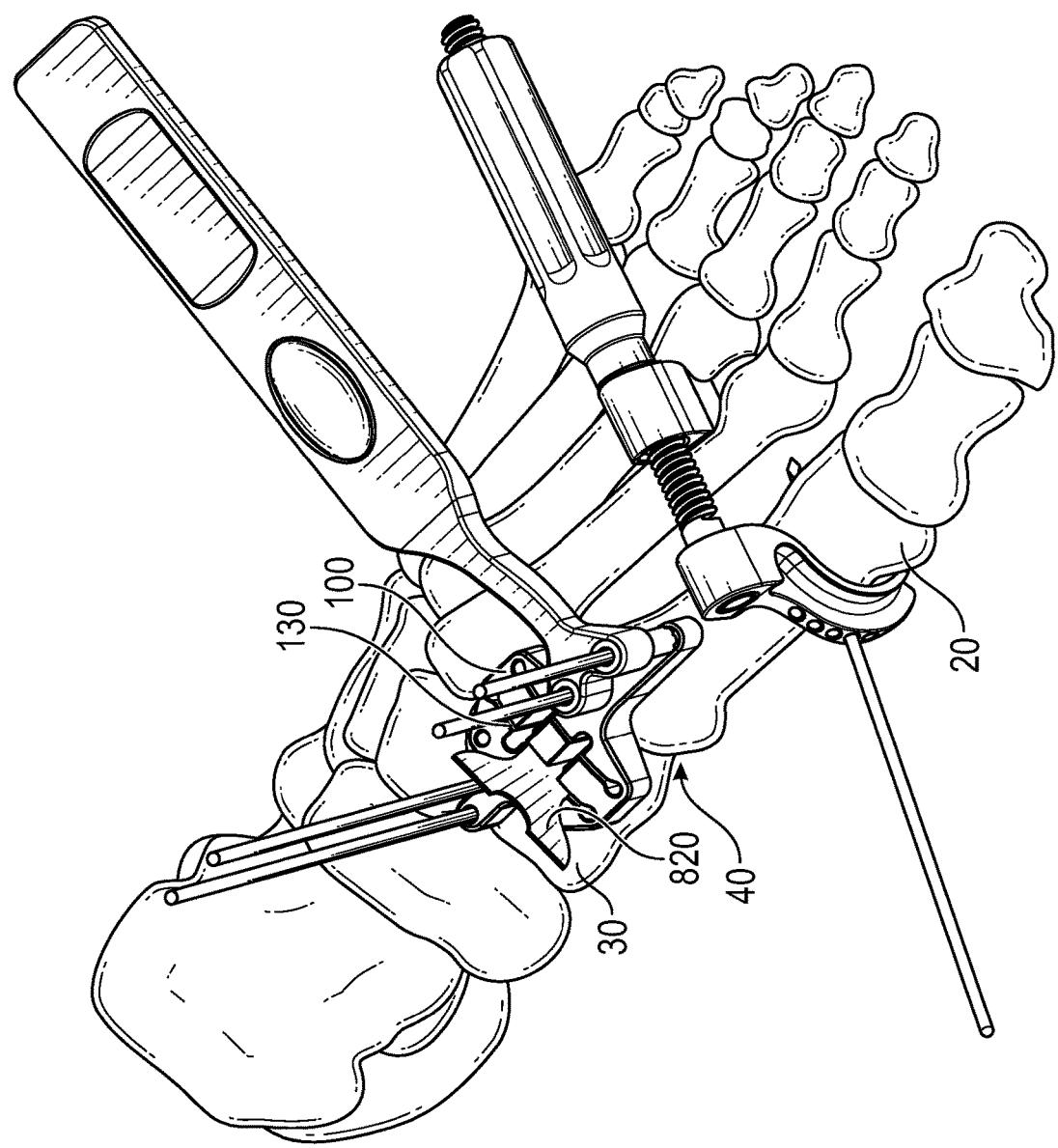

Continuing to FIG. 14, once the cuneiform pins 818 or wires are inserted, the base of the first cuneiform 30 is cut using a saw blade 820 inserted through the proximal slot 130 of the cut guide 100. Cutting the base of the first cuneiform 30 completes the excision of the first TMT joint 40. With reference to FIG. 15, the cut guide 100, the linear reducer 200, and the control handle 300 are removed from the foot 10. The control handle 300 can be removed by sliding upward until the control handle is free of the metatarsal pins 802 or wires. The cut guide 100 can similarly be removed by sliding the cut guide 100 upward until it is free of the metatarsal pins 802 or wires and the cuneiform pins 818 or wires. The linear reducer 200 is removed by removing the medial hook pin 816 and lifting the medial and lateral hooks 205, 215 away from the foot 10. In some embodiments, a quick-release medial hook 235 may be used to facilitate removal of the linear reducer. After removal of the cut guide 100, linear reducer 200, and control handle 300, the fully disarticulated first TMT joint is left with the metatarsal pins 802 or wires and cuneiform pins 818 or wires remaining in place. At this point, the surgeon may further use any desired means to distract and further prepare the joint in preparation for fusion.

Referring now to FIG. 16, the compressor block 400 is applied over the metatarsal pins 802 or wires and cuneiform pins 818 or wires. Preferably, the metatarsal pins 802 or wires are either shorter or longer than the cuneiform pins 818 or wires (e.g., by approximately the height of the compressor block 400 or more, as shown in FIG. 16). In the example of FIG. 16, the compressor block 400 is applied by first threading the proximal pin holes 410 onto the relatively longer cuneiform pins 818 or wires, followed by threading the distal pin holes 415 onto the relatively shorter metatarsal pins 802 or wires. As discussed above with reference to FIGS. 5A-5D, unlike the pin holes of the cut guide 100, the pin holes of the compressor block 400 are slightly closer together and tapered inward such that it may be difficult to attempt to insert all four pins or wires through the compressor block 400 simultaneously.

Due to the convergent angle of the proximal pin holes 410 to the distal pin holes 415, sliding the compressor block 400 downward over the cuneiform pins 818 or wires and the metatarsal pins 802 or wires pulls the metatarsal pins 802 or wires closer to the cuneiform pins 818 or wires. Thus, the application of the compressor block 400 causes the first metatarsal 20 to move along direction 822 toward the first cuneiform 30, bringing the cut face of the first metatarsal 20 into contact with the cut face of the first cuneiform 30. The angled holes cause a rotation of the pins in the sagittal plane so that the plantar side of the joint is compressed. This may be desirable, as compression on only the dorsal aspect of the bones may in some cases cause a plantar gapping of the joint which is undesirable for fusion.

Figure 19:
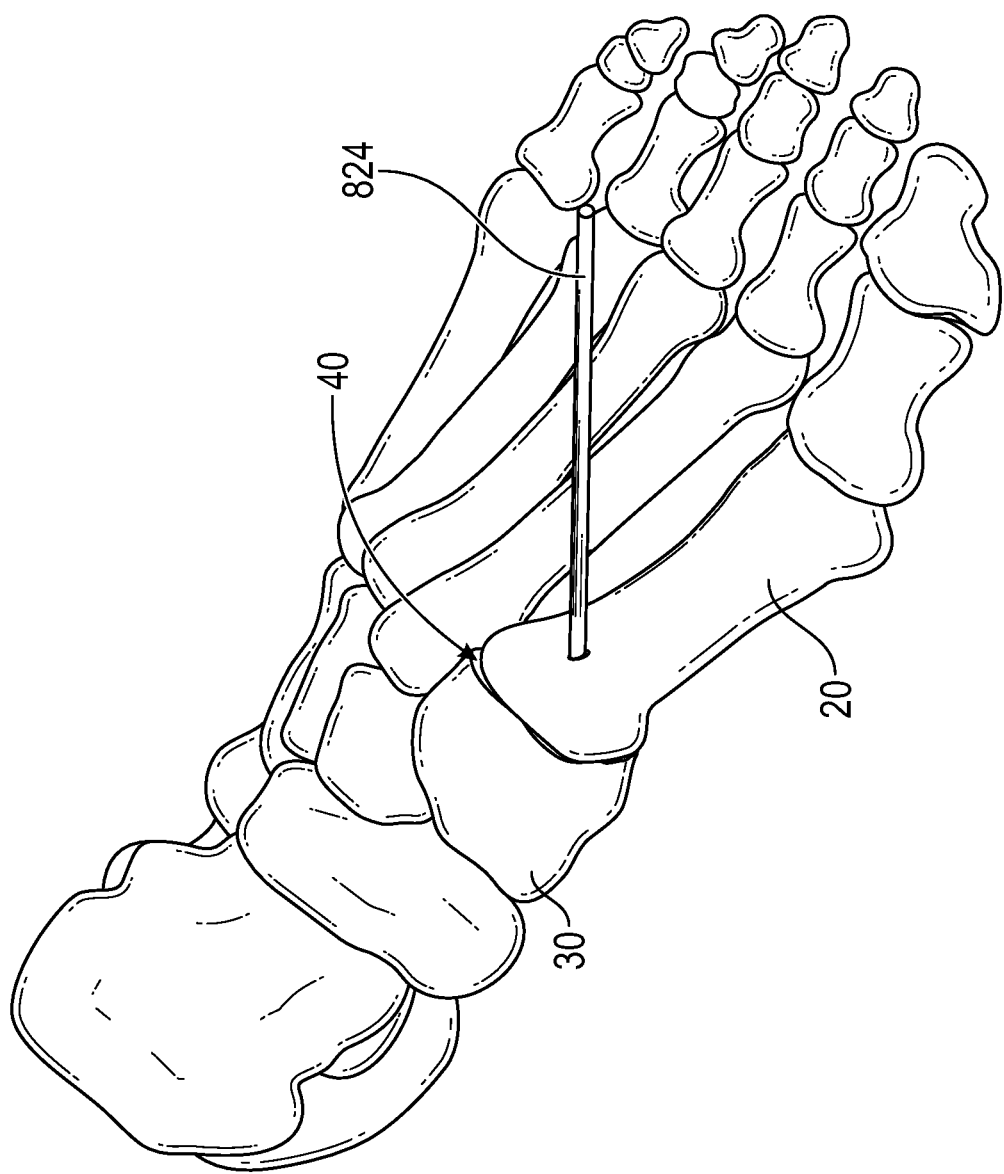

Continuing to FIG. 17, a cross pin 824 is then inserted through one of the cross pin holes 420 such that the cross pin 824 passes through the compressed joint to temporarily fix the joint in place. As shown in FIG. 18, the metatarsal pins 802 or wires and the cuneiform pins 818 or wires are removed. As shown in FIG. 19, the compressor block 400 may then be removed by sliding the compressor block outward along the cross pin 824, which remains in place to fix the joint until the bone plate 500 can be applied. Any number of cross pin hole trajectories could be applied to the compression block 400 for placement of the crossing wire. Although the cross pin 824 is shown as being inserted distally and extending proximally into the joint, in other embodiments the compression block 400 may have cross pin holes 420 located proximally instead of or in addition to distally. In such embodiments, the cross pin 824 would be inserted from a proximal end of the compression block 400 and would extend distally through the joint.

Figure 20:
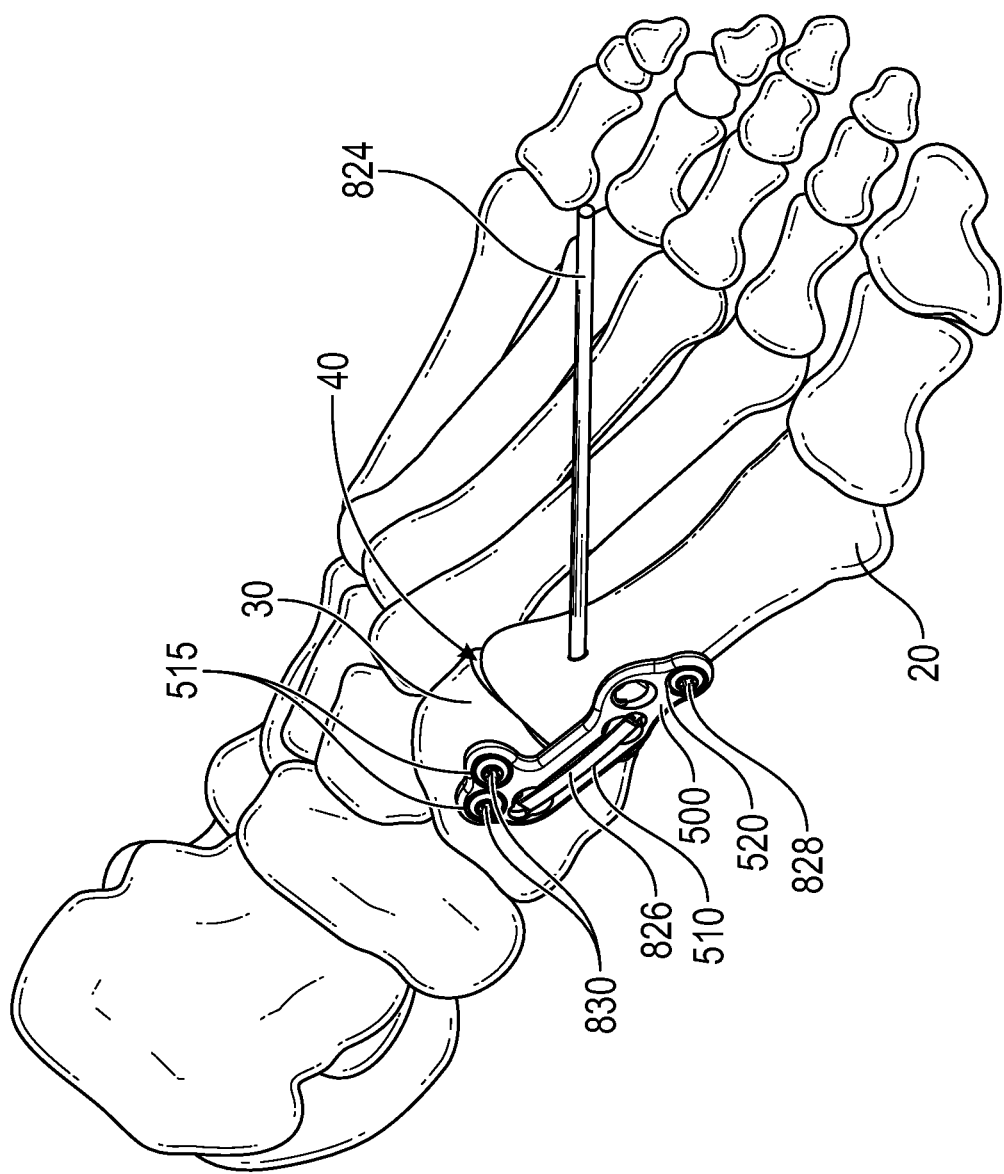
Figure 21:
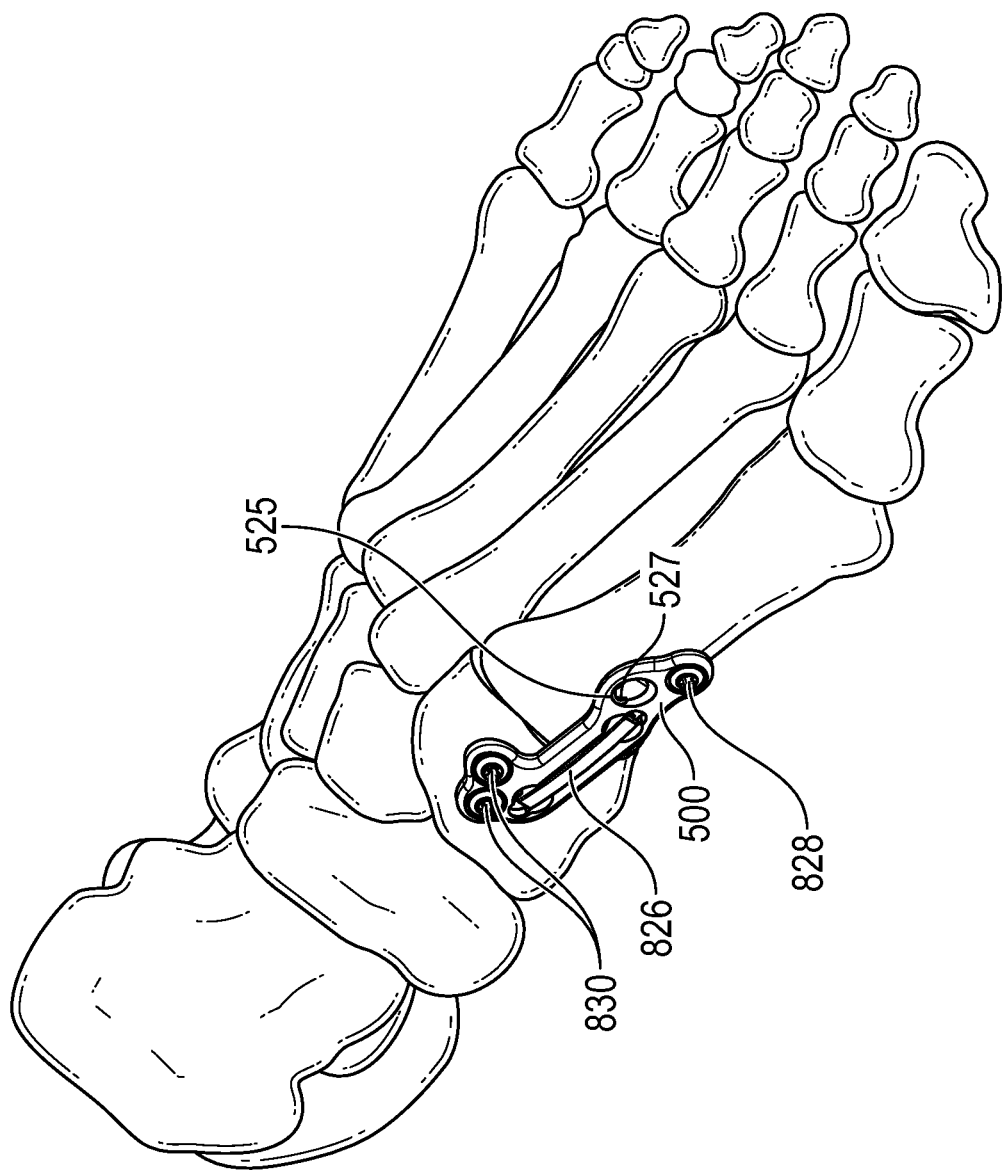

With reference to FIG. 20, while the joint is fixed in place by the cross pin 824, the bone plate 500 is placed across the resected first TMT joint 40. Pilot holes are drilled as necessary. In order to fix the first metatarsal 20 relative to the first cuneiform 30, a staple 826 is placed at the staple aperture 510, a metatarsal screw 828 is placed at the metatarsal screw aperture 520, and cuneiform screws 830 are placed at the cuneiform screw apertures 515. The staple 826, metatarsal screw 828, and cuneiform screws 830 can be placed in any order; however, it may be preferable to place the staple 826 and the metatarsal screw 828 prior to placing the cross screw 834. As shown in FIG. 21, when the first metatarsal 20 and the first cuneiform 30 have been fixed using the bone plate 500, the cross pin 824 is no longer necessary and can be removed. The staple 826 may be made of a shape-memory material. In some embodiments, the staple 826 is held in a deformed configuration wherein the staple legs are approximately parallel during insertion through the plate 500. After insertion, the staple 826 may be allowed to relax toward a non-deformed configuration, where the legs are angled towards each other. Thus, after insertion, the staple 826 provides a compression force across the TMT joint 40. More details regarding the plate-staple system may be found in U.S. Pat. No. 10,299,842, which is incorporated herein by reference in its entirety. More details regarding staples suitable for use as described herein can be found in U.S. Publication No. 2018/0317906, which is incorporated herein by reference in its entirety.

Figure 22:
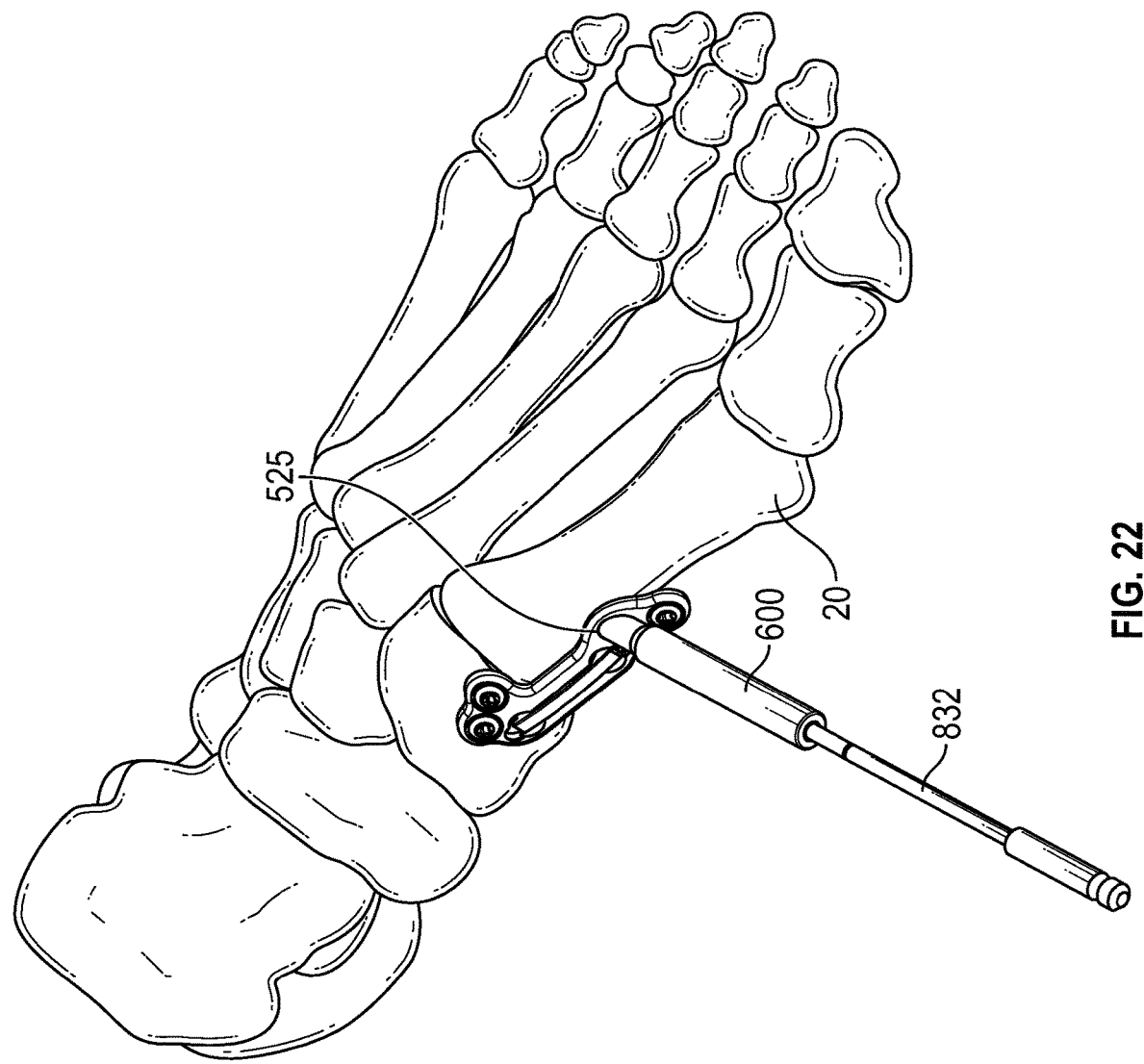

Continuing to FIG. 22, a cross screw drill guide is placed within the cross screw aperture 525 of the bone plate 500. Although the fixed-angle cross screw drill guide 600 of FIGS. 7A-7C is shown in FIG. 22, the procedure may equally be implemented using the variable-angle cross screw drill guide 650 of FIGS. 7D-7F. The cross screw drill guide 600 is seated in the cross screw aperture 525 by seating the shelf engagement surface 627 (or the shelf engagement surface 677 if the variable-angle cross screw drill guide 650 is used) against the shelf 527 of the cross screw aperture 525. A drill bit 832 is inserted through the cross screw drill guide 600 and turned to drill a pilot hole for a cross screw within the cross screw aperture 525. The drill bit 832 and the cross screw drill guide 600 are removed, and the cross screw 834 is placed at the cross screw aperture 525, completing the Lapidus bunionectomy procedure.

Figure 23:
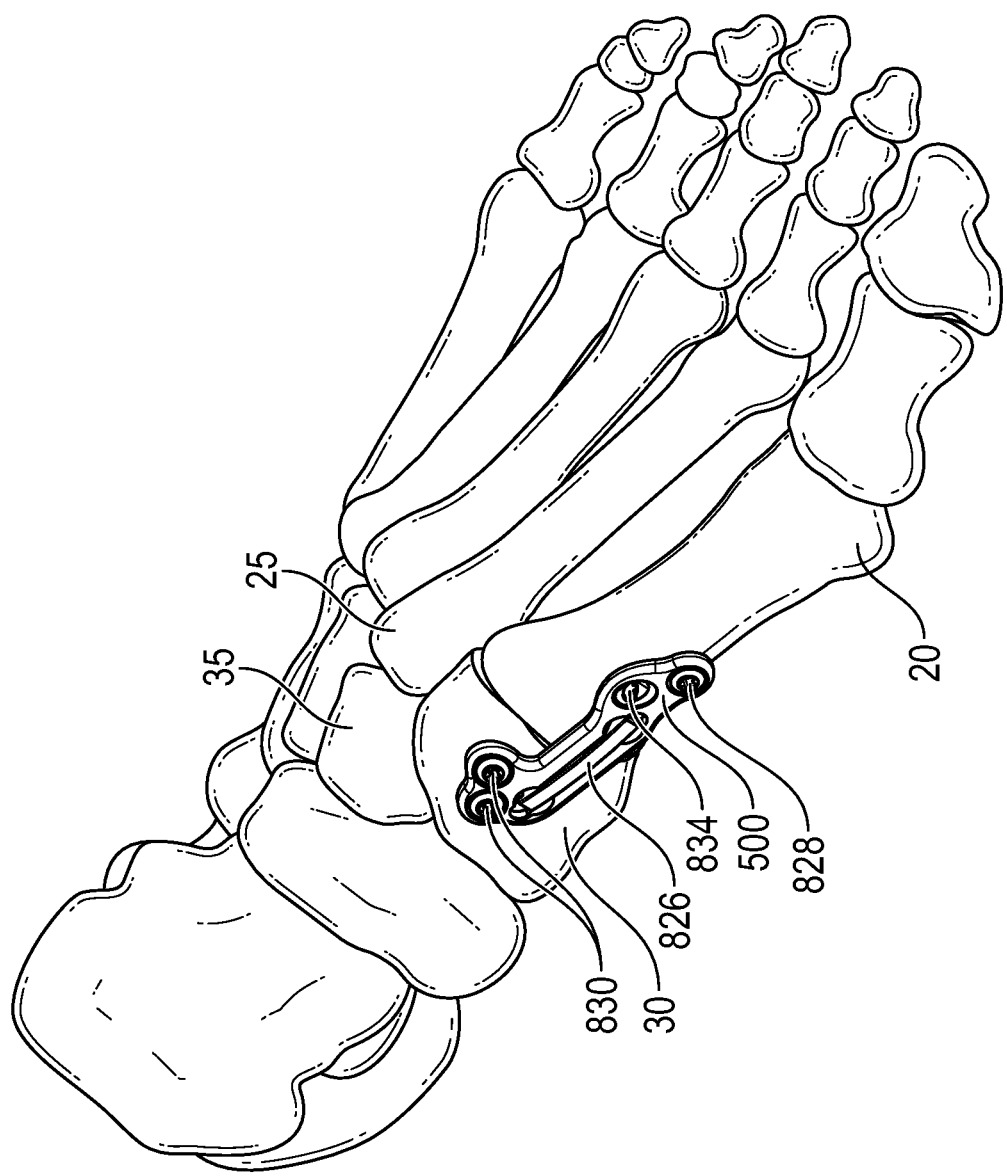
Figure 24:
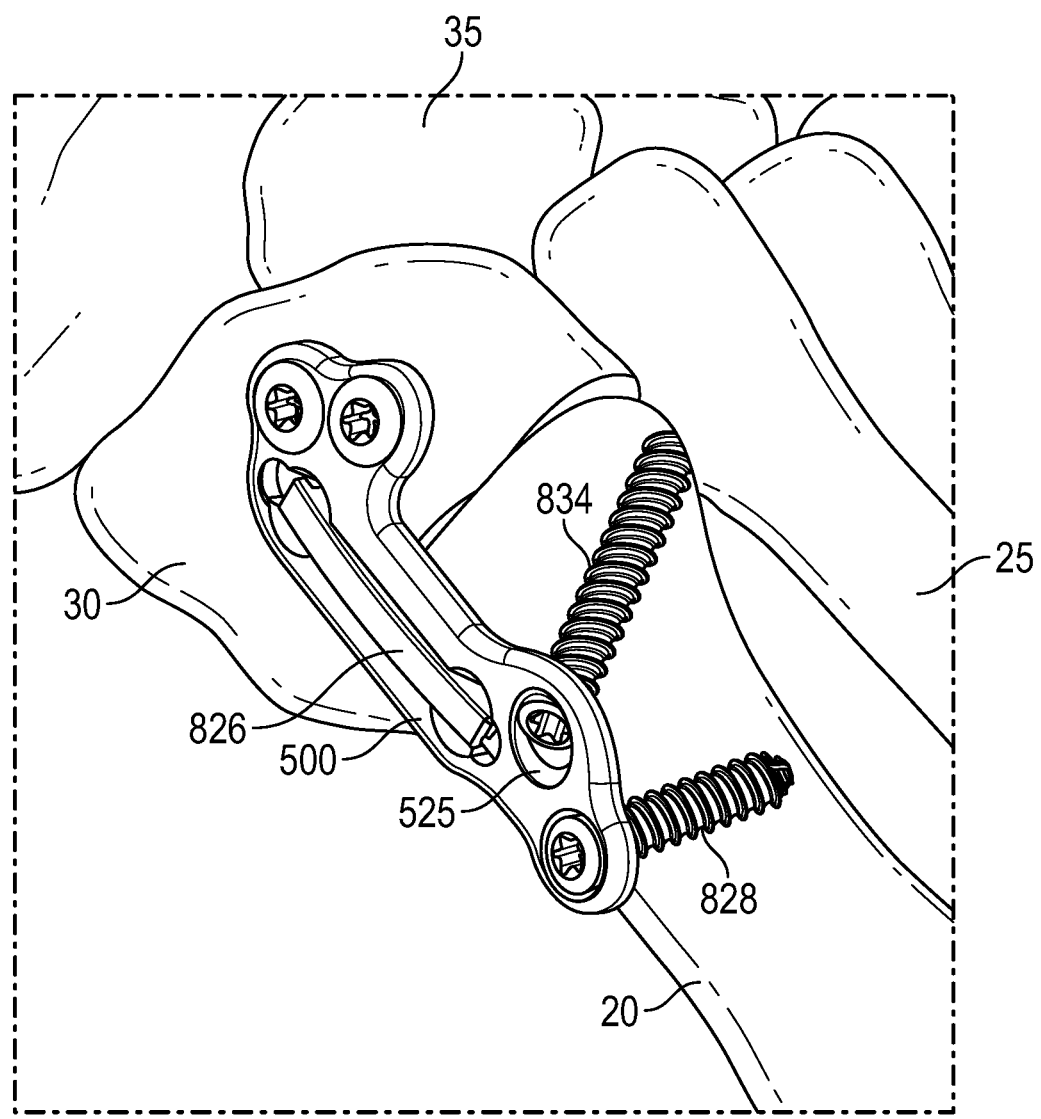

FIGS. 23 and 24 show the completed state of the Lapidus bunionectomy in accordance with the present technology. FIG. 24 is an enlarged view of a portion of the foot, in which the first metatarsal 20 is shown with transparency to illustrate the internal placement of the cross screw 834. As shown in FIGS. 23 and 24, the first metatarsal 20 is fixed in a desired orientation relative to the first cuneiform 30, with a reduced intermetatarsal angle relative to the second metatarsal 25, by the bone plate 500, the staple 826, the metatarsal screw 828, and the cuneiform screws 830.

Advantageously, the cross screw 834 further functions to prevent future recurrence of the bunion. As the foot may still experience daily pressure that could cause the bunion to return, the cross screw 834 anchors the first metatarsal 20 to either the second metatarsal 25 or the second cuneiform 35, depending on the geometry of the foot and the angle of insertion of the cross screw 834. Thus, the Lapidus bunionectomy of FIGS. 8-24 advantageously goes beyond merely repairing the bunion by providing an additional structural connection to more laterally disposed bones of the midfoot to prevent recurrence.

With reference to FIGS. 25-29, a portion of an alternative Lapidus bunionectomy using certain devices herein will be described. The portion of the Lapidus bunionectomy illustrated in FIGS. 25-29 provides an alternative method of performing the first metatarsal and first cuneiform cuts using the single-slotted cut guide 180 illustrated in FIGS. 2H-2K. Thus, as will be described in greater detail below, the portion of the Lapidus bunionectomy illustrated in FIGS. 25-29 may be used in conjunction with portions of the Lapidus bunionectomy illustrated in FIGS. 8-24 and/or with other bunionectomy procedures. Although the procedure of FIGS. 25-29 illustrates a particular implementation of a Lapidus bunionectomy using a specific subset of the devices disclosed herein, it will be understood that the components and steps illustrated and described with reference to FIGS. 25-29 may equally be applied in different sequences and/or with different combinations of components to correct a bunion.

Figure 25:
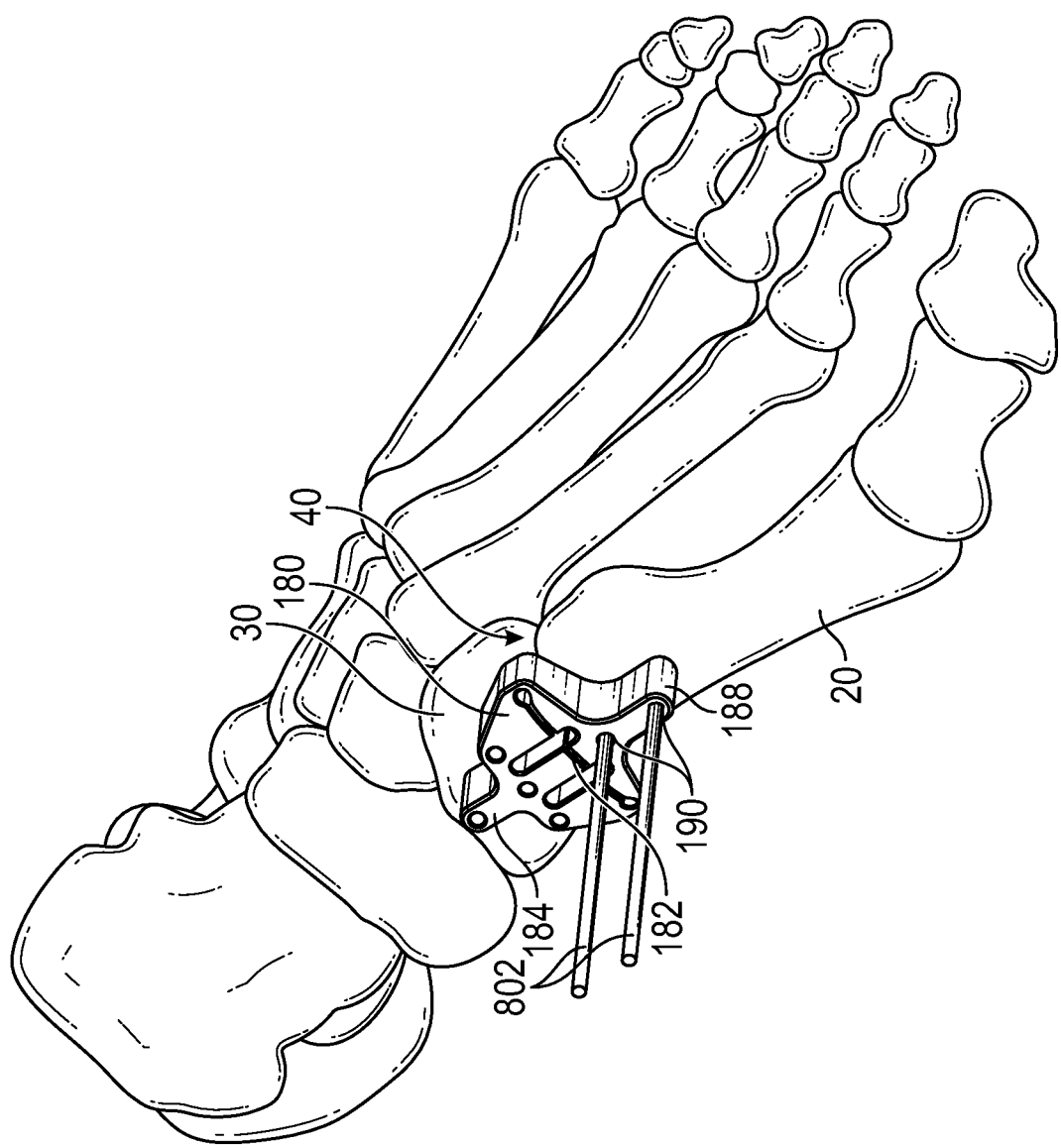
FIGS. 25-29 are perspective views of the bones of a foot, sequentially illustrating a portion of an example Lapidus bunionectomy procedure performed using the example bunionectomy devices disclosed herein.

As shown in FIG. 25, the procedure may begin by placing and temporarily securing the cut guide 180 of FIGS. 2H-2K to the foot 10. Similar to the beginning configuration of FIG. 8, the first TMT joint 40 may have been prepared by making an incision such as a dorsomedial incision to expose the first TMT joint 40 and excising soft tissue around the joint, such as the joint capsule or other soft tissue, to expose the first TMT joint 40 and create a space in which the paddle 120 (FIGS. 2H-2K) of the cut guide 180 can be seated.

Once the joint has been prepared, the cut guide 180 is placed by seating the paddle 120 (not visible in FIG. 25) within the first TMT joint 40 such that the first extension 184 sits adjacent to or against the first cuneiform 30 and the second extension 188 sits adjacent to or against the first metatarsal 20. The paddle 120 is inserted into the first TMT joint 40 such that the cut guide 180 is oriented along the axis of the first metatarsal 20 with the slot 182 positioned over the first metatarsal 20. Alternatively, in some embodiments, the cut guide 180 may be oriented with the slot 182 positioned over the first cuneiform 30, and the bunionectomy may be performed such that the first cuneiform 30 is cut before the first metatarsal 20. The alignment of the cut guide 180 may be confirmed under fluoroscopy or other suitable imaging technique before proceeding.

When the cut guide 180 has been placed and is suitably aligned, the cut guide 180 is temporarily secured relative to the first metatarsal 20 by inserting one or more metatarsal pins 802 or wires through the second pin holes 190 of the second extension 188 and into or through the first metatarsal 20. The metatarsal pins 802 or wires, as well as any of the other pins or wires described in the following description, may be, for example, a Kirschner wire ("K-wire"), or any other suitable type of wire or pin that can be placed into the bone to secure the cut guide 180. Although two metatarsal pins 802 or wires are illustrated in this example, the cut guide 180 may be suitably robust and stable when held in place by the paddle 120 and a single metatarsal pin 802 or wire.

Figure 26:
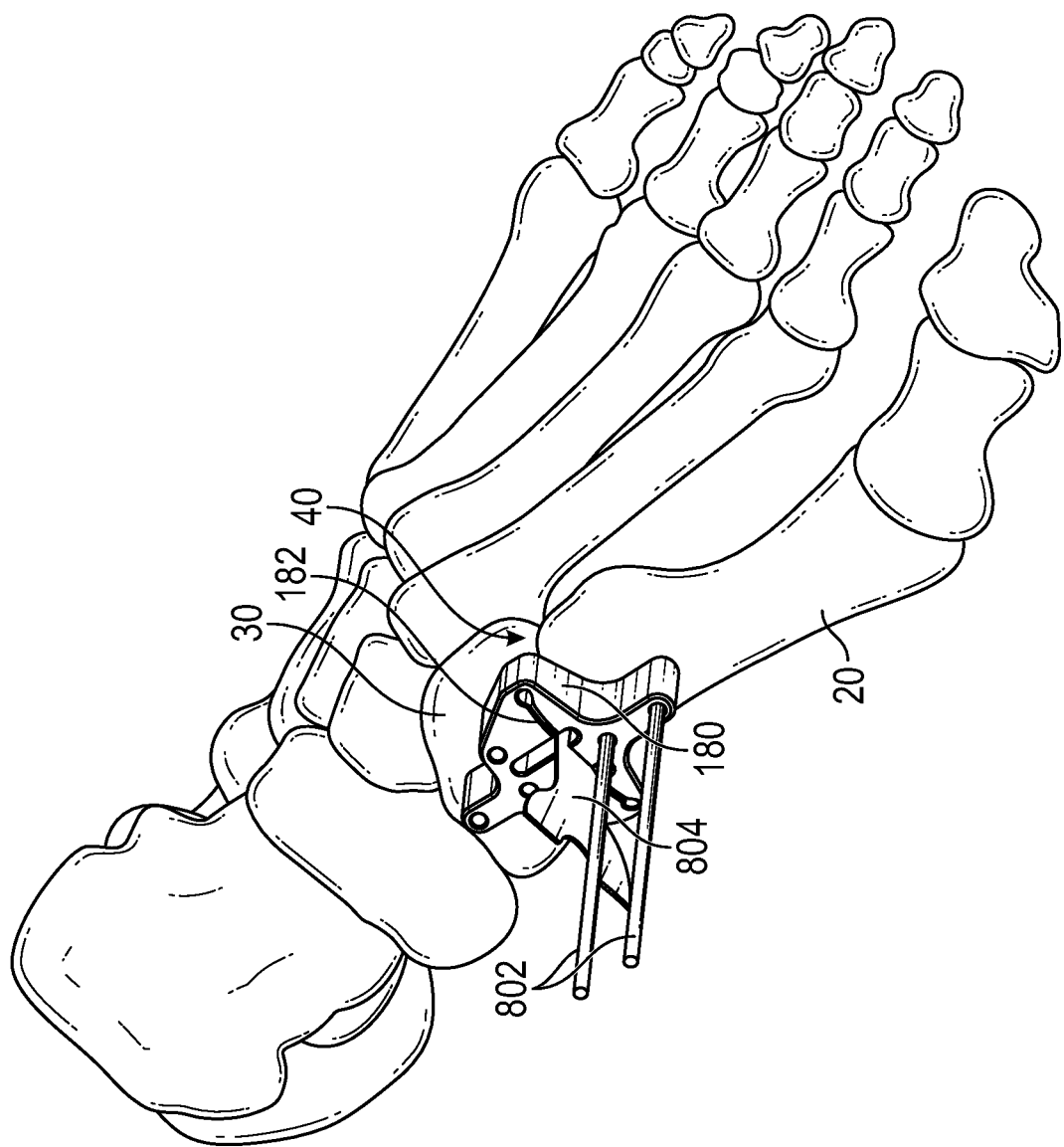

Continuing to FIG. 26, once the metatarsal pins 802 or wires are inserted, the base of the first metatarsal 20 is cut using a saw blade 804 inserted through the slot 182 of the cut guide 180.

Figure 27:
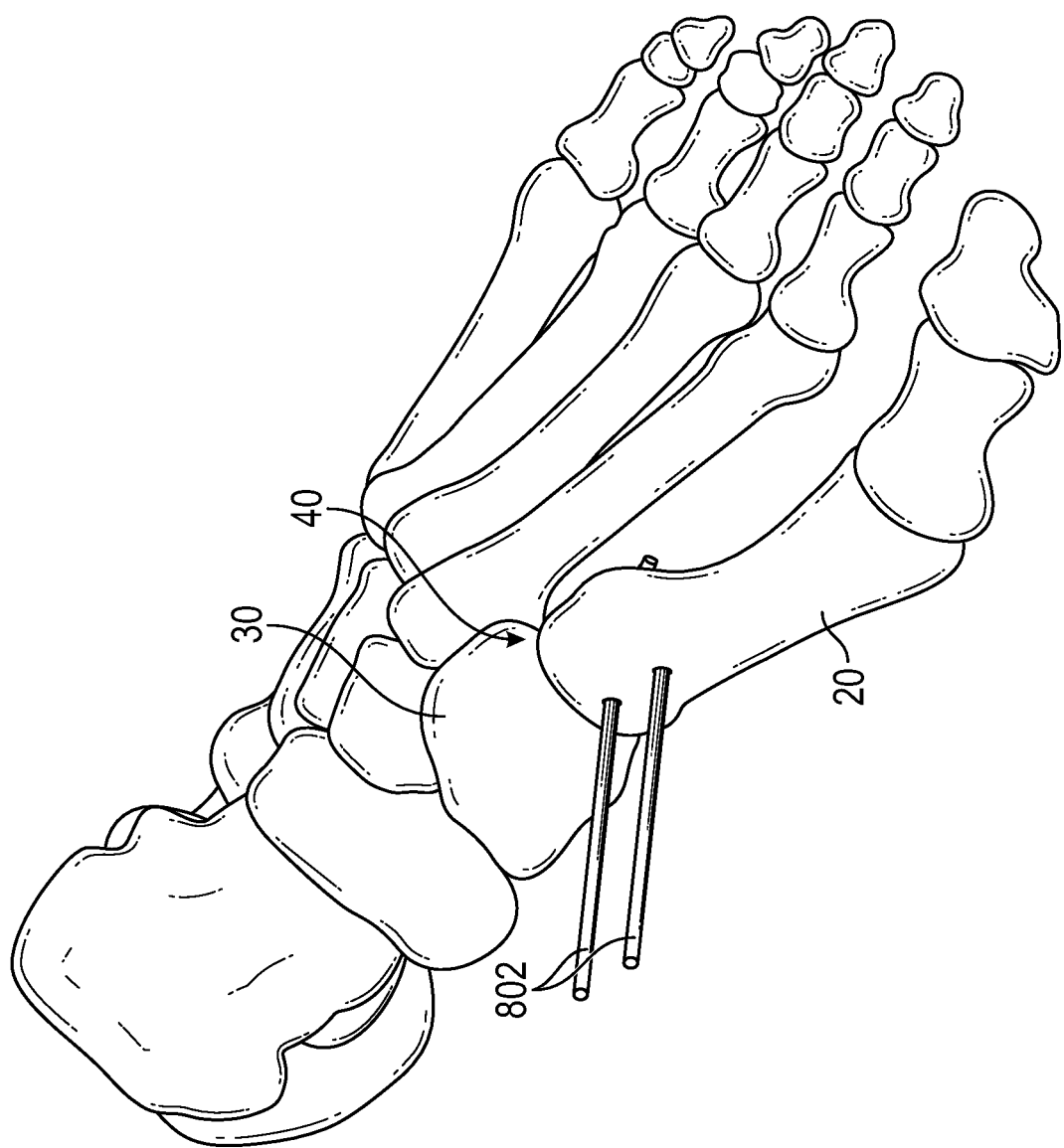
Figure 28:
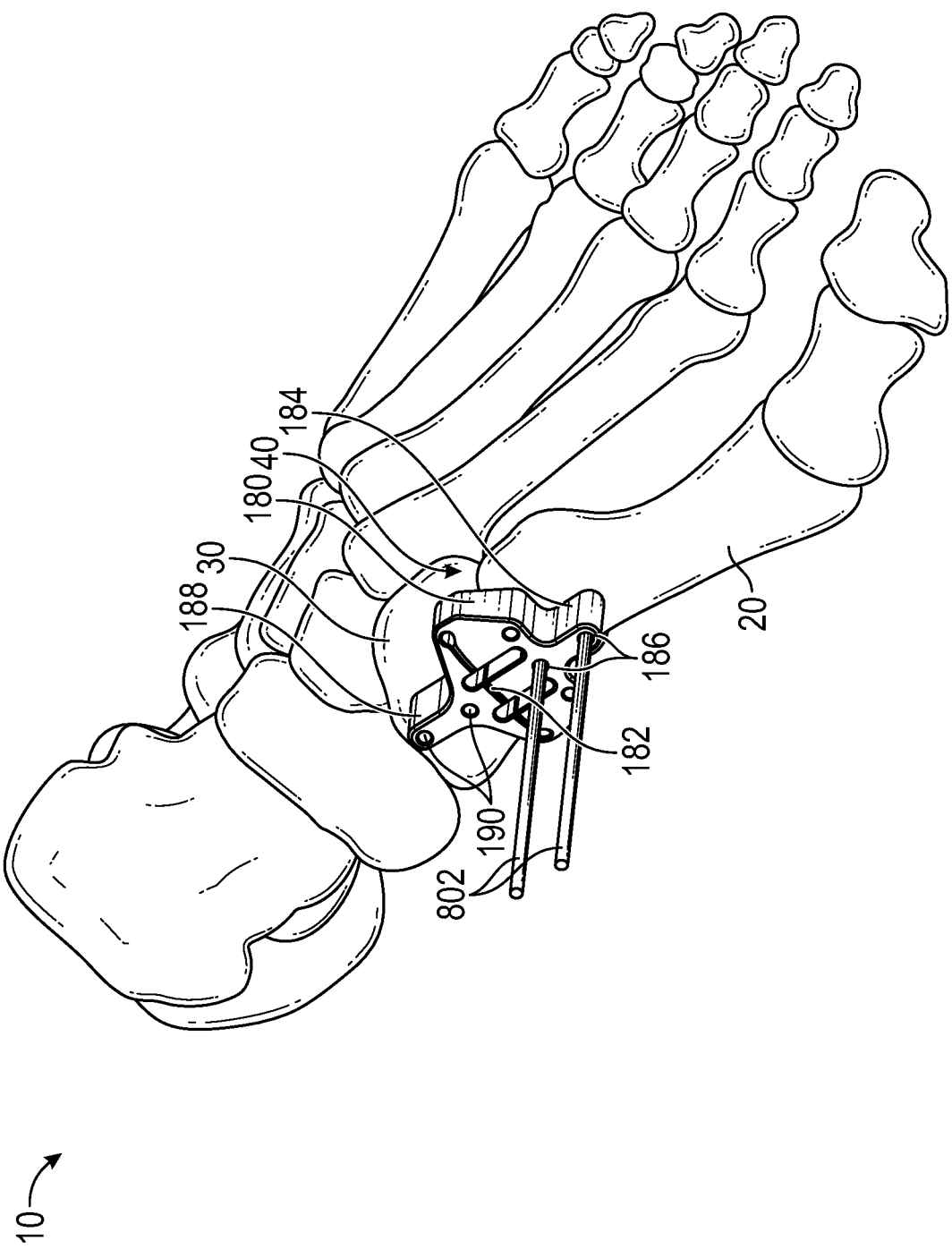

With reference to FIGS. 27 and 28, after the base of the first metatarsal 20 is cut, the cut guide 180 can be reoriented such that the same slot 182 can be used to guide the cutting of the first cuneiform 30 which occurs later in the Lapidus bunionectomy procedure. The cut guide 180 can be removed by sliding the cut guide 180 upward until the second pin holes 190 are free of the metatarsal pins 802 or wires, as shown in FIG. 27. At this stage, the resected portion of the bone from the first metatarsal 20 (or from the first cuneiform 30 if the first cuneiform 30 was cut first) can be removed from the foot 10. The cut guide 180 can then be reversed (e.g., rotated 180 degrees about an axis parallel to the metatarsal pines 802 or wires). The metatarsal pins 802 or wires may then be inserted through the first pin holes 186, and the cut guide 180 may be moved downward along the metatarsal pins 802 or wires until the paddle 120 is again seated within the first TMT joint 40, as shown in FIG. 28. In some embodiments, the first pin holes 186 and second pin holes 190 have a different spacing about the center of the paddle 120. For example, the first pin holes 186 may be closer to the paddle 120 by a distance equal to the thickness of the bone removed by the first cut, such that reversing the cut guide 180 results in the paddle 120 resting firmly against the cut surface of the first metatarsal 20.

In the configuration of FIG. 28, due to the reversal of the cut guide 180, the second holes 190 are disposed above the first cuneiform 30 and the slot 182 is positioned to guide cutting of the first cuneiform 30 rather than the first metatarsal 20. From the state illustrated in FIG. 28, the Lapidus bunionectomy procedure can proceed substantially as shown and described with reference to FIGS. 10-13 for correction of the position of the first metatarsal 20 and phalanges 50 in the frontal and transverse planes. In the same process described with reference to FIG. 13, two cuneiform pins 818 or wires are inserted through the second pin holes 190 of the cut guide 180 and into or through the first cuneiform 30. The cuneiform pins 818 or wires temporarily secure the cut guide 180 relative to the first cuneiform 30. At this point, the four pins 802 and 814 form an array that establishes and/or locks the surgeon's desired correction.

Figure 29:
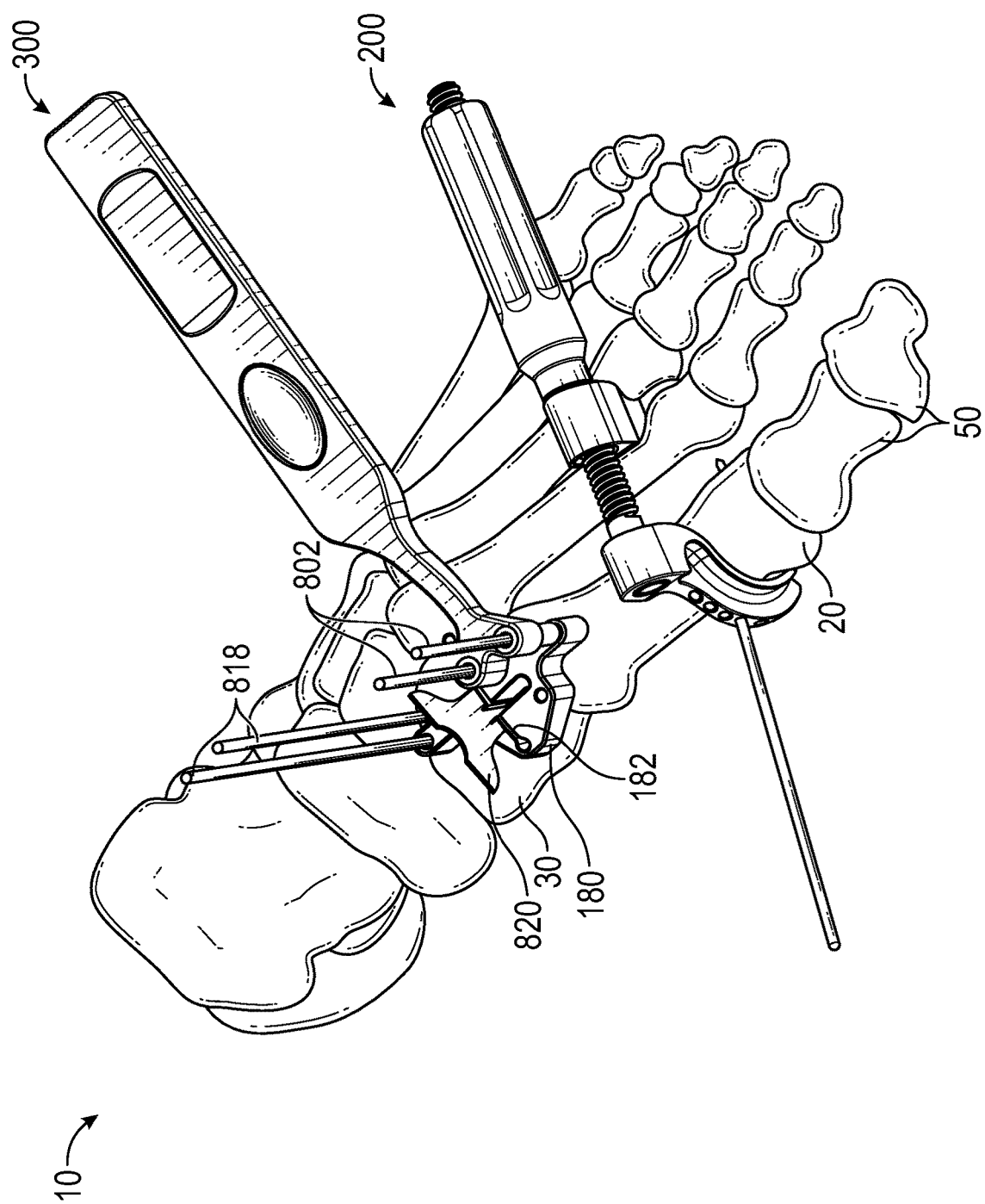

Referring now to FIG. 29, due to the reversal of the cut guide 180 following cutting of the first metatarsal 20, the slot 182 is now positioned on the cuneiform side of the first TMT joint 40. Thus, following correction of the bunion in at least the frontal and/or transverse planes and the placing of the cuneiform pins 818 or wires, the slot 182 is positioned to guide the cutting of the first cuneiform 30.

Once the cuneiform pins 818 or wires are inserted, the base of the first cuneiform 30 is cut using a saw blade 820 inserted through the slot 182 of the cut guide 180. Cutting the base of the first cuneiform 30 completes the excision of the first TMT joint 40. The cut guide 180, the linear reducer 200, and the control handle 300 may then be removed from the foot 10 by the same or similar operations to those described above with reference to FIG. 15. After removal of the cut guide 180, linear reducer 200, and control handle 300, the fully disarticulated first TMT joint 40 is left with the metatarsal pins 802 or wires and cuneiform pins 818 or wires remaining in place. At this point, the surgeon may further use any desired means to distract and further prepare the joint in preparation for fusion. The remainder of the Lapidus bunionectomy procedure may then proceed substantially as shown and described with reference to FIGS. 16-24.

With reference to FIGS. 30A-32C, various additional devices and components are provided for use with an improved Lapidus bunionectomy procedure for correcting the TMT joint deformity of FIG. 1. The devices and components of FIGS. 30A-32C may be used to perform additional optional steps in the Lapidus bunionectomy procedures described herein, such as additional removal of bone and/or additional rotational correction of the frontal plane prior to fixation. Although the following description is made with reference to the Lapidus bunionectomy procedure, it will be understood that the various devices and components described herein are not limited to such procedures and may equally be used in other orthopedic procedures as will be understood by those skilled in the art.

Figure 30A:
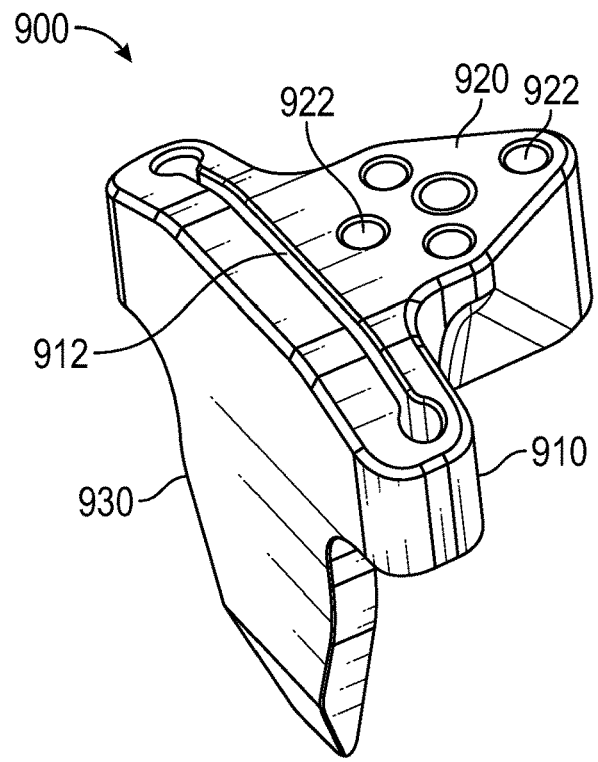
FIGS. 30A-30C depict an example cut guide configured as a re-cutting guide and a pin guide for the Lapidus bunionectomy procedures described herein.
Figure 30B:
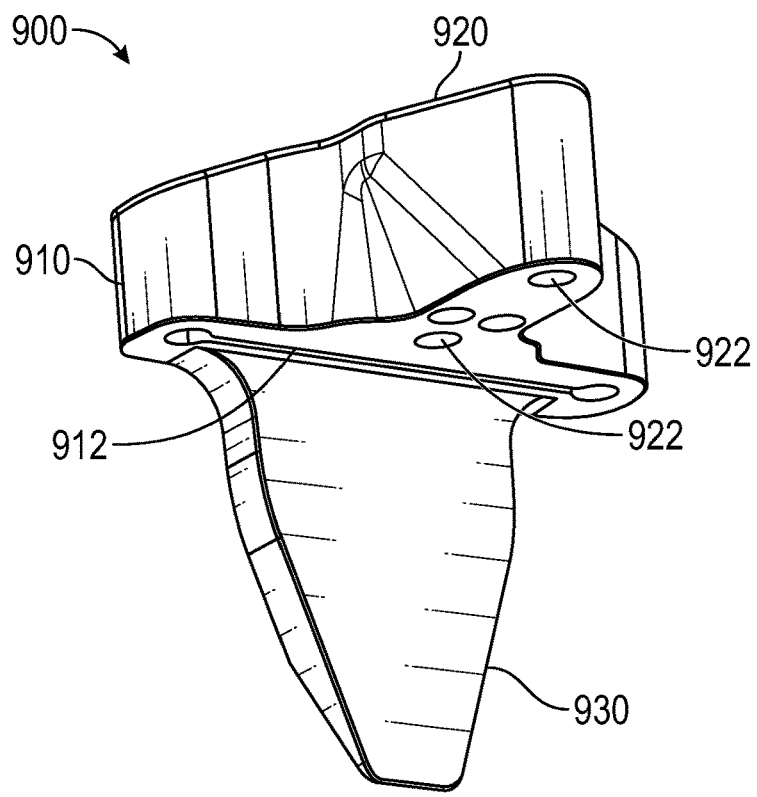
Figure 30C:
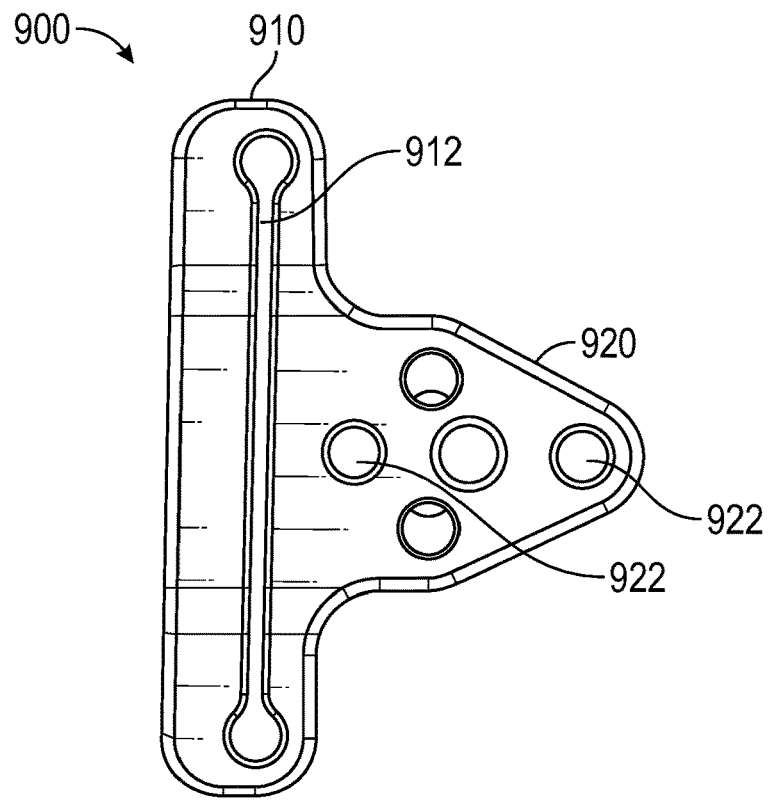

FIGS. 30A-30C depict a cut guide 900 configured as a re-cut guide and a pin guide for the Lapidus bunionectomy procedures described herein. In some Lapidus bunionectomy procedures, a surgeon may desire to remove additional bone from the first metatarsal and/or from the first cuneiform at the first TMT joint during the procedure. For example, the edges of the first metatarsal and/or first cuneiform forming the TMT joint may have varying levels of concavity in different individuals, such that some first metatarsals and/or first cuneiforms may need to have more bone cut away in order to reach a plane at which interior bone is exposed over the full cross-section of the cut area.

FIGS. 30A and 30B are upper and lower perspective views of the cut guide 900, respectively. FIG. 30C is a top plan view of the cut guide 900. The cut guide 900 may be a single integrally formed component and may comprise a metal, a plastic, or other suitable material. The cut guide 900 may be sized and shaped to be used in conjunction with (e.g., after) another cut guide such as the cut guide 181 of FIGS. 2L-2N.

The cut guide 900 generally comprises a body 910, an extension 920, and a paddle 930. The extension 920 can have a size and shape similar or identical to the second extension 188 of the cut guide 181 and can include pin holes 922 having a spacing corresponding to the spacing of second pin holes 190 of the cut guide 181. The body 910 includes a slot 912. The paddle 930 is sized and shaped to seat within a joint such as a TMT joint, for example.

To accomplish the desired re-cut functionality, the spacing between the slot 912 and the pin holes 922 of the cut guide 900 is closer than the corresponding spacing in an associated cut guide used for the initial joint cutting. For example, in a kit including a cut guide 900 and a cut guide 181 (FIGS. 2L-2N), the distance between the slot 912 and the nearer of the pin holes 922 is shorter than the distance between the slot 182 and the nearer of the second pin holes 190 of the cut guide 180. Accordingly, after cut is made using the cut guide 181 held in place by pins extending through the second pin holes 190, the cut guide 181 can be removed and the cut guide 900 can be placed over the same pins through pin holes 922 such that the slot 912 defines a cutting plane closer to the pins for re-cutting. Use of the cut guide 900 as a re-cut guide will be described in greater detail with reference to FIGS. 33-35.

Figure 31A:
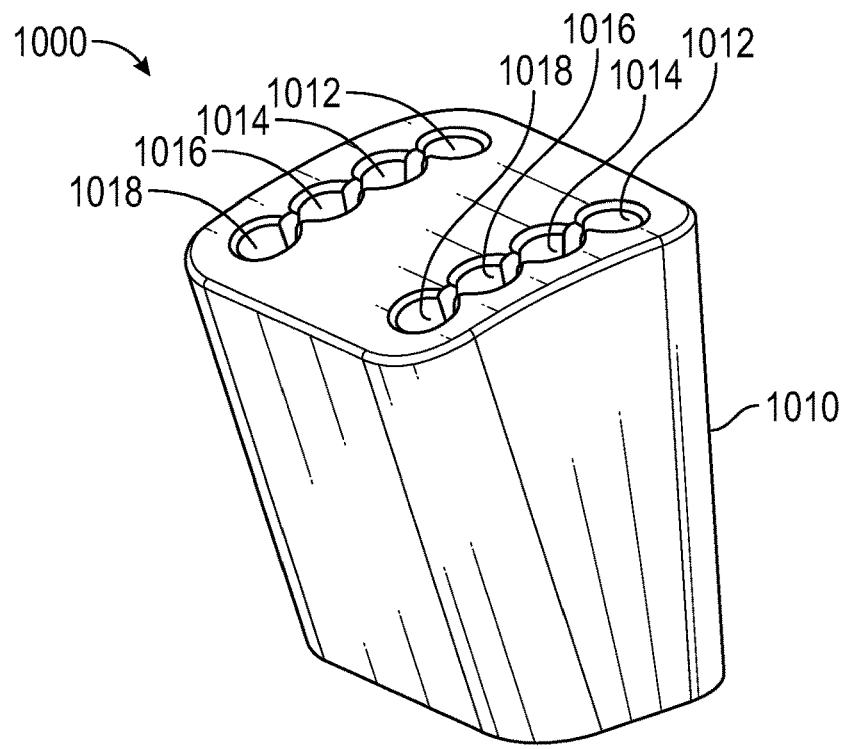
FIGS. 31A-31C depict an example realignment guide configured as a pin guide for frontal plane adjustment in the Lapidus bunionectomy procedures described herein.
Figure 31B:
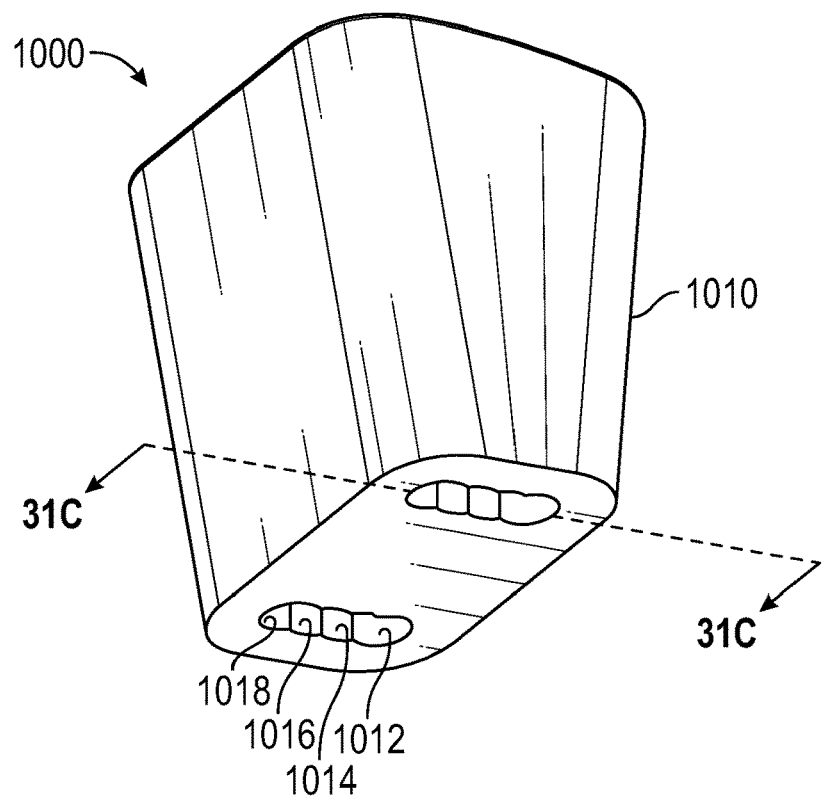
Figure 31C:
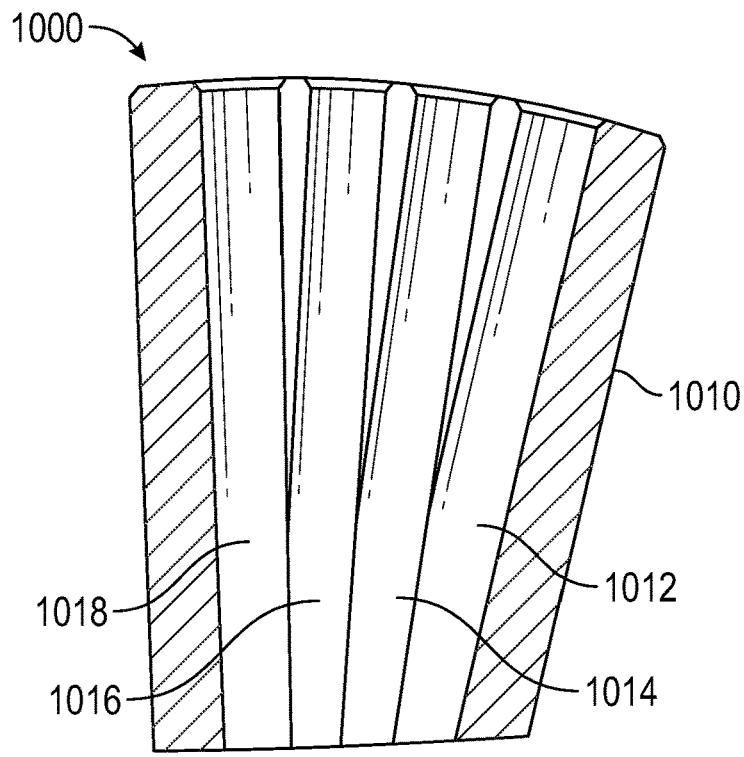

FIGS. 31A-31C depict an example realignment guide 1000 configured as a pin guide for frontal plane adjustment in the Lapidus bunionectomy procedures described herein. FIGS. 31A and 31B are upper and lower perspective views of the realignment guide 1000, respectively. FIG. 31C is a cross-sectional side elevation view of the realignment guide 100 taken about the line 31C-31C in FIG. 31B. The realignment guide 1000 includes a body 1010 having two or more pairs of pin holes therethrough. The body 1010 is generally wedge-shaped and may be integrally formed from a metal, a plastic, or other suitable material.

In the example realignment guide 1000 of FIGS. 31A-31C, the body 1010 includes four pairs of pin holes 1012, 1014, 1016, and 1018. Each pair of pin holes 1012, 1014, 1016, 1018 may be parallel, and the pairs are oriented in a converging configuration. Each pair of pin holes 1012, 1014, 1016, 1018 may be spaced apart by a distance corresponding to the pin hole spacing of an associated cut guide (e.g., cut guide 180, 181, 900, etc.). The pin holes 1012, 1014, 1016, 1018 may thus be used to implement further frontal plane correction by being placed over an existing pair of pins and serving as a guide for placement of a second pair of similarly spaced, parallel pins at a predetermined angular offset about a metatarsal bone relative to the existing pair. the use of the realignment guide 100 will be described in greater detail with reference to FIGS. 39-48.

Figure 32A:
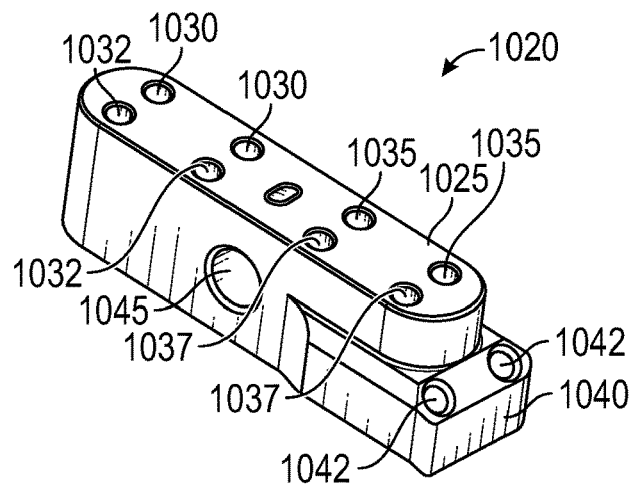
FIGS. 32A-32C depict an example realignment guide configured as a pin guide for frontal plane adjustment in the Lapidus bunionectomy procedures described herein.
Figure 32B:
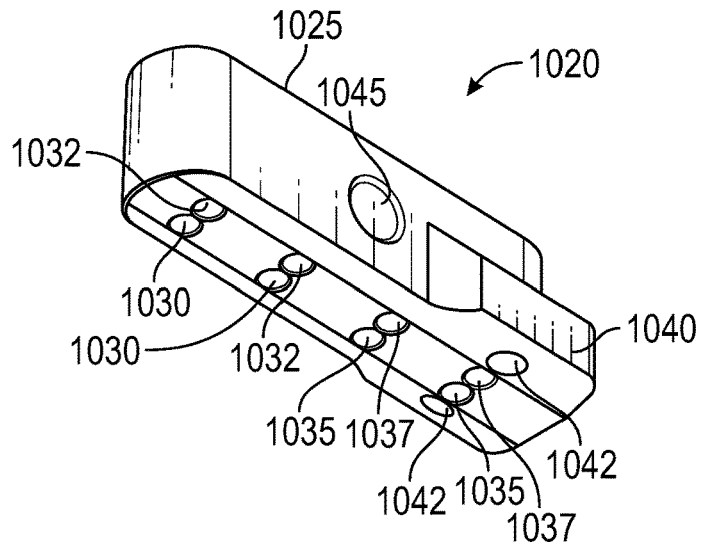
Figure 32C:
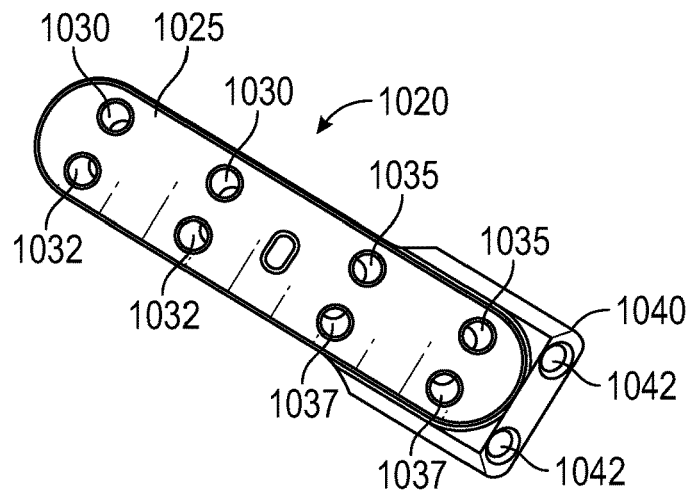

FIGS. 32A-32C depict an example realignment guide 1020 configured as a pin guide and a compression block for frontal plane adjustment in the Lapidus bunionectomy procedures described herein. FIGS. 32A and 32B are upper and lower perspective views of the realignment guide 1020, respectively. FIG. 32C is a top plan view of the realignment guide 1020. The realignment guide 1020 may be integrally formed form a metal, a plastic, or other suitable material. The realignment guide 1020 may have a shape generally similar to the compressor block 400 and can function as both a realignment guide and a compressor block in operation.

The realignment guide 1020 includes a body 1025 having two pairs of proximal pin holes 1030, 1032 and two pairs of distal pin holes 1035, 1037. Similar to the proximal pin holes 410 and the distal pin holes 415 of the compressor block 400, the proximal pin holes 1030, 1032 and distal pin holes 1035, 1037 are convergent toward the middle of the realignment guide 1020. A widened section 1040 can include cross pin holes 1042 for additional stabilization and/or for temporary fixation while permanent fixation devices are placed. As will be described in greater detail with reference to FIGS. 36-38, the realignment guide 1020 may be used to implement additional frontal plane correction of the first metatarsal without requiring the insertion of additional pins into the bone.

Figure 34:
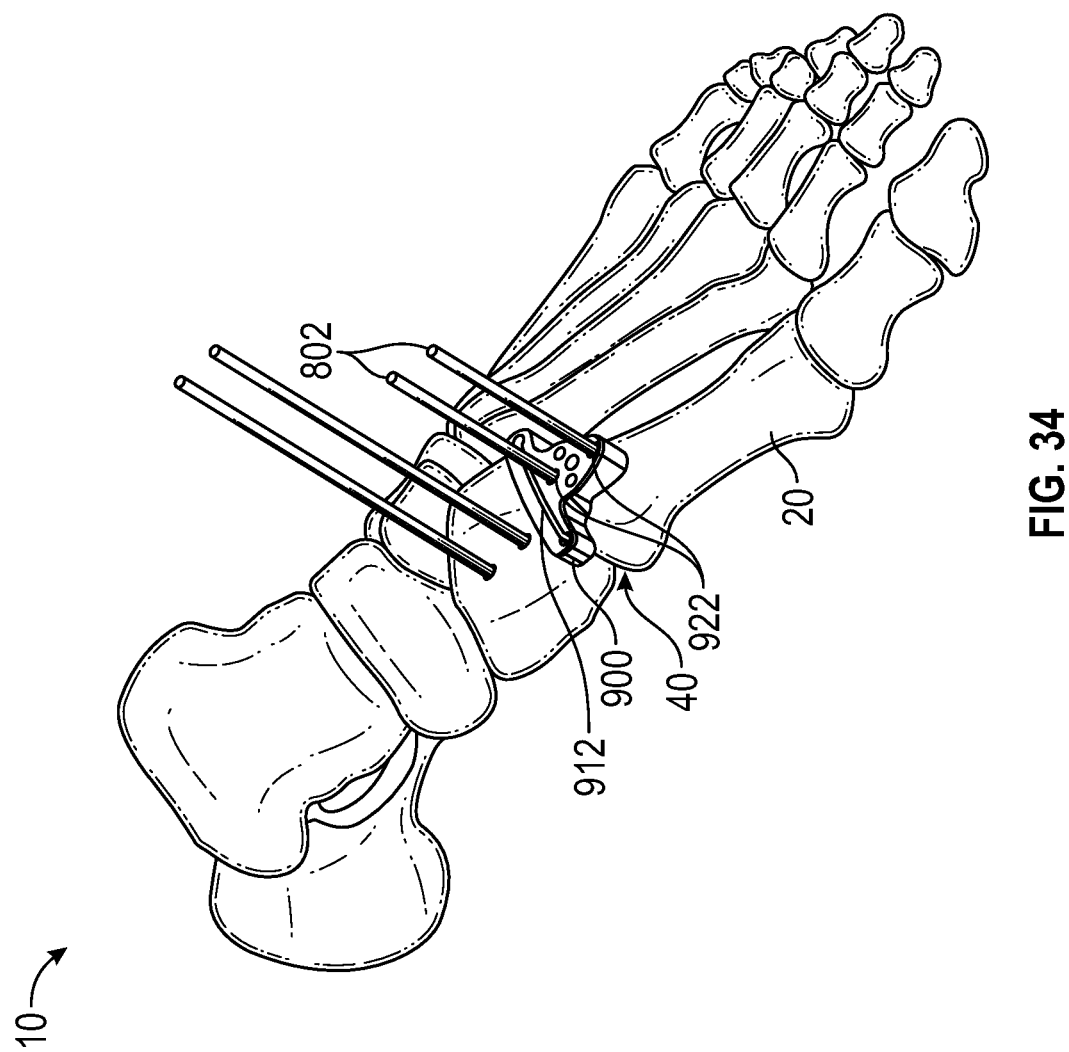
Figure 35:
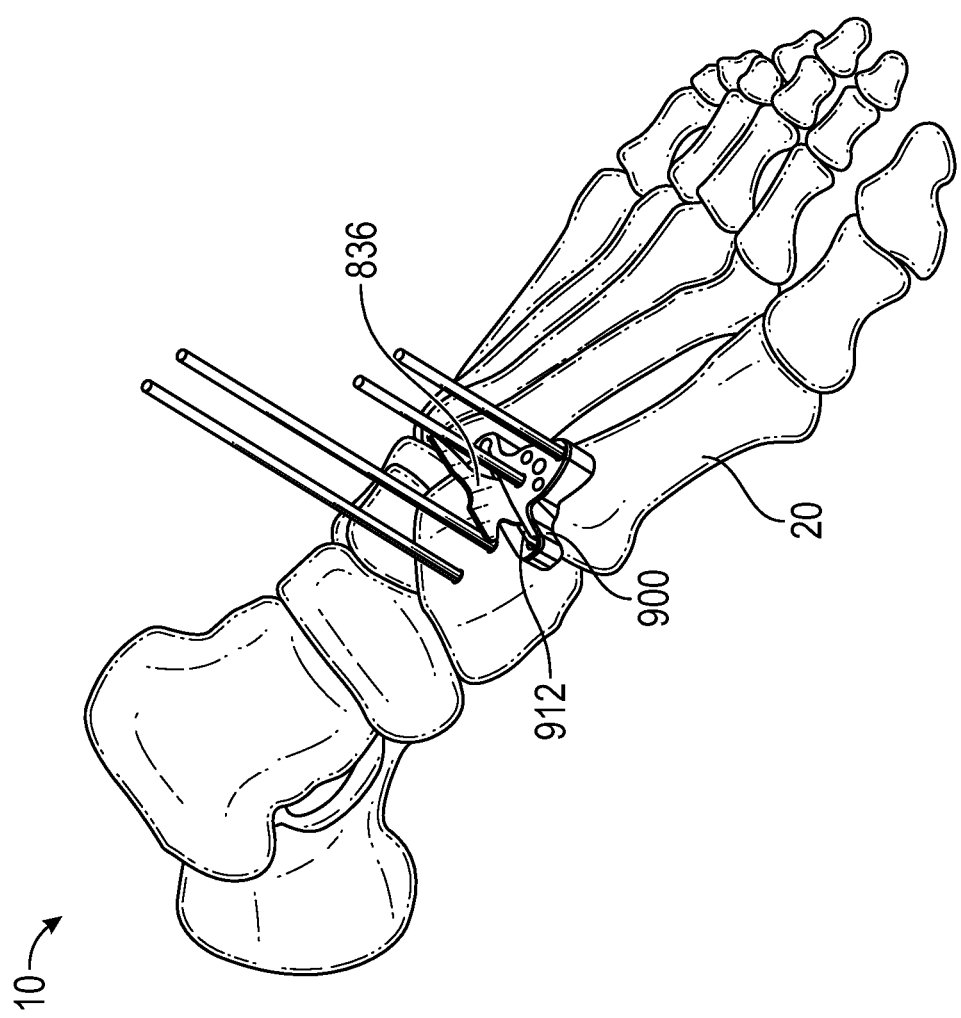

FIGS. 33-35 are perspective views of the bones of a foot 10, sequentially illustrating a re-cutting portion of an example Lapidus bunionectomy procedure performed using the example bunionectomy devices disclosed herein. The re-cutting portion of the Lapidus bunionectomy illustrated in FIGS. 33-35 may be performed at any time after an initial cut has been made to the first metatarsal 20 and/or to the first cuneiform 30, where further removal of bone is desired. For example, in some procedures, a surgeon may examine the cut end of a first metatarsal 20 and/or first cuneiform 30 and determine that further bone should be removed due to concavity of the bone or a desired spacing. Thus, as will be described in greater detail below, the portion of the Lapidus bunionectomy illustrated in FIGS. 33-35 may be used in conjunction with any of the other Lapidus bunionectomy procedures described herein.

As shown in FIG. 33, the re-cutting portion may begin with the foot 10 in a configuration similar to that of FIG. 15. In the configuration of FIG. 33, a cut guide (e.g., cut guide 100, cut guide 180, cut guide 181, etc. as disclosed elsewhere herein) may have been used to remove a portion of the first metatarsal 20 and/or the first cuneiform 30. Metatarsal pins 802 and/or cuneiform pins 818 may remain in the foot 10 following removal of the cut guide that was used to make the initial cuts to the first metatarsal 20 and/or first cuneiform 30. In the example re-cutting portion illustrated in FIGS. 33-35, it is desired to remove an additional portion of the first metatarsal 20 facing the first TMT joint 40.

Continuing to FIG. 34, the cut guide 900, configured as a re-cut guide, is placed by inserting the metatarsal pins 802 through the pin holes 922 of the cut guide 900 and sliding the cut guide 900 onto the metatarsal pins 802 until the cut guide 900 is seated against the previously cut face of the first metatarsal 20. In this configuration of FIG. 34, the slot 912 of the cut guide 900 is aligned closer to the metatarsal pins 802 than the TMT joint-facing end of the first metatarsal 20 due to the closer spacing of the cut guide 900 relative to that of the cut guides 100, 180, 181. Once the cut guide 900 is placed, the base of the first metatarsal 20 can be re-cut using a saw blade 836 inserted through the slot 912 of the cut guide 900. The remainder of the Lapidus bunionectomy procedure may the proceed substantially as shown and described with reference to FIGS. 16-24 or as described elsewhere herein. It will be understood that the re-cutting described above may be applied equally to the first metatarsal 20 or to the first cuneiform 30.

Figure 36:
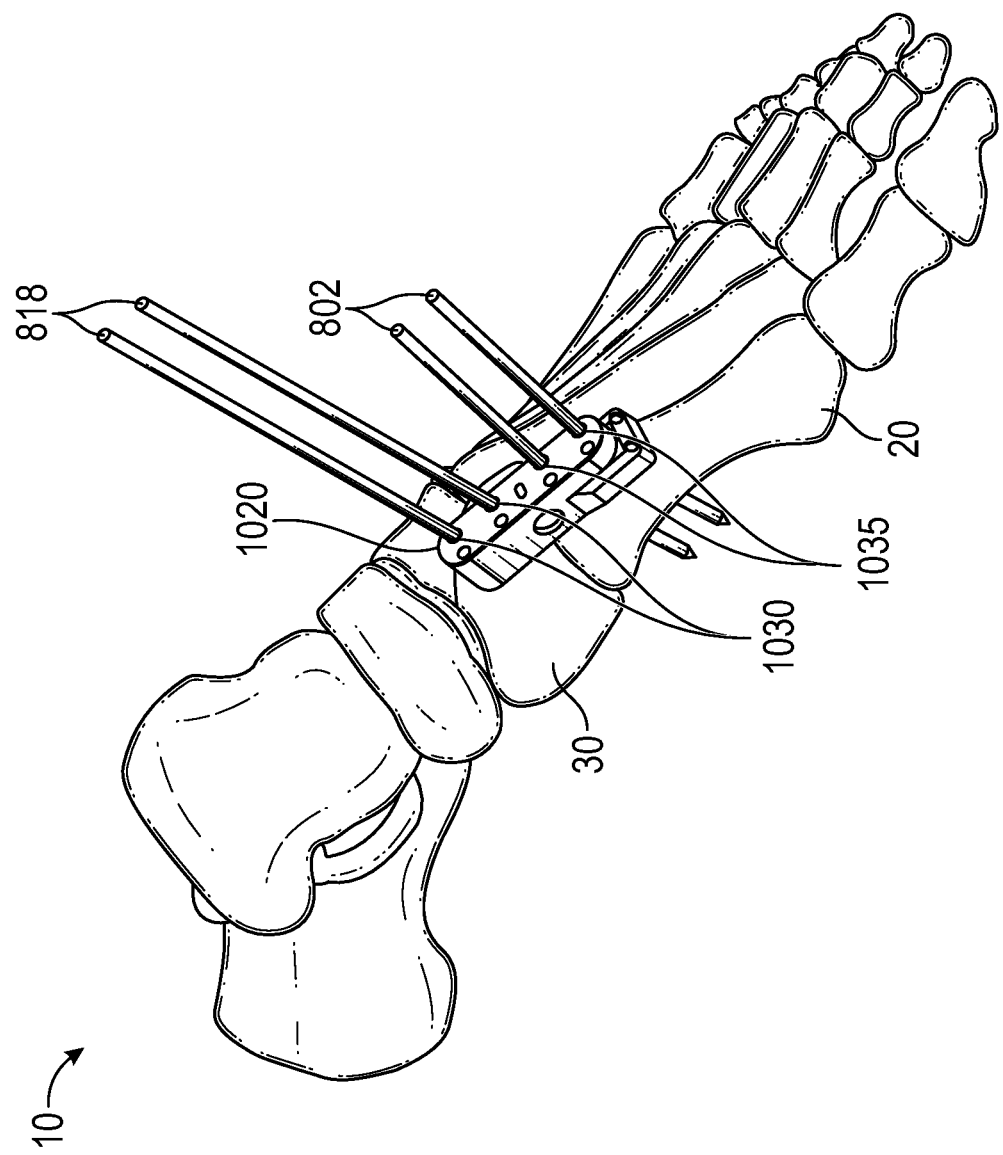
FIGS. 36-38 are perspective views of the bones of a foot, sequentially illustrating a frontal plane realignment portion of an example Lapidus bunionectomy procedure using the example bunionectomy devices disclosed herein.
Figure 37:
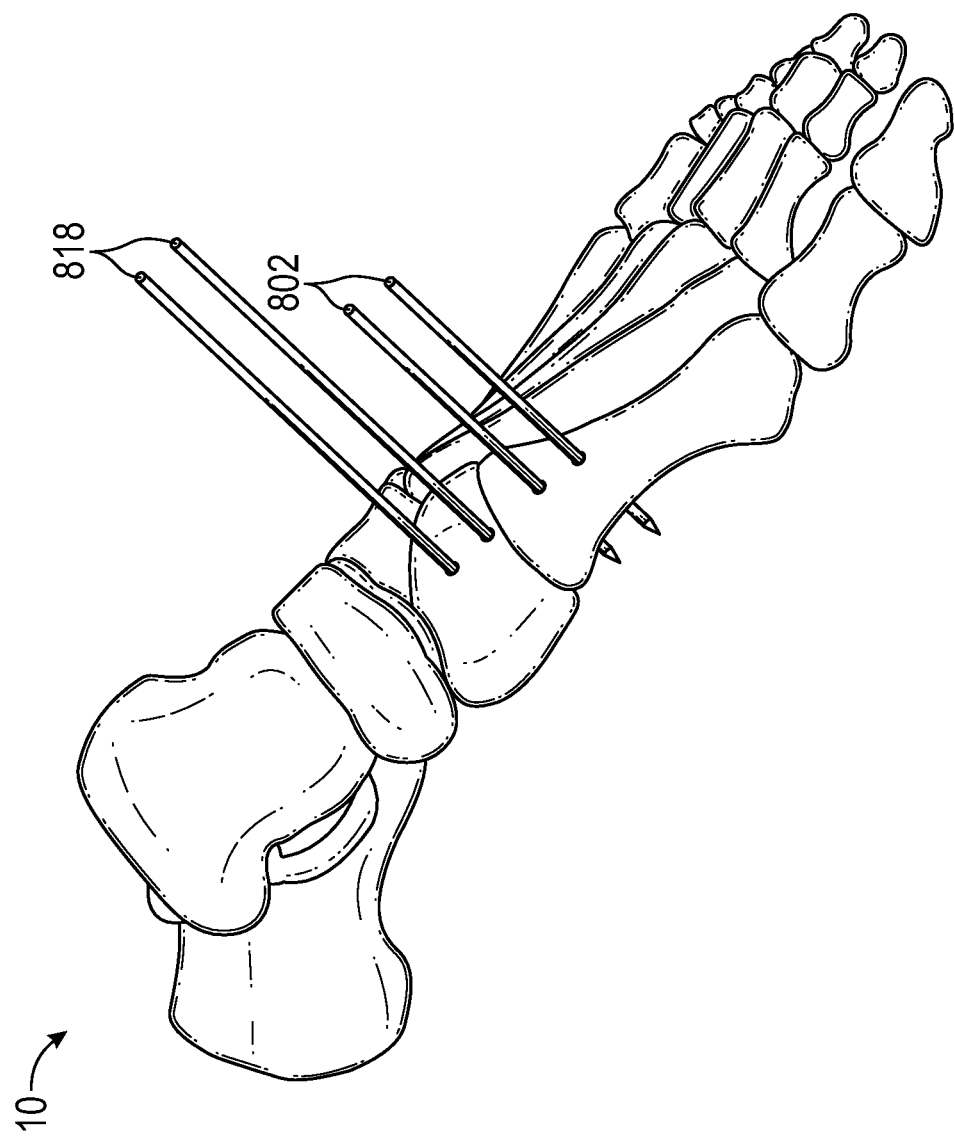
Figure 38:
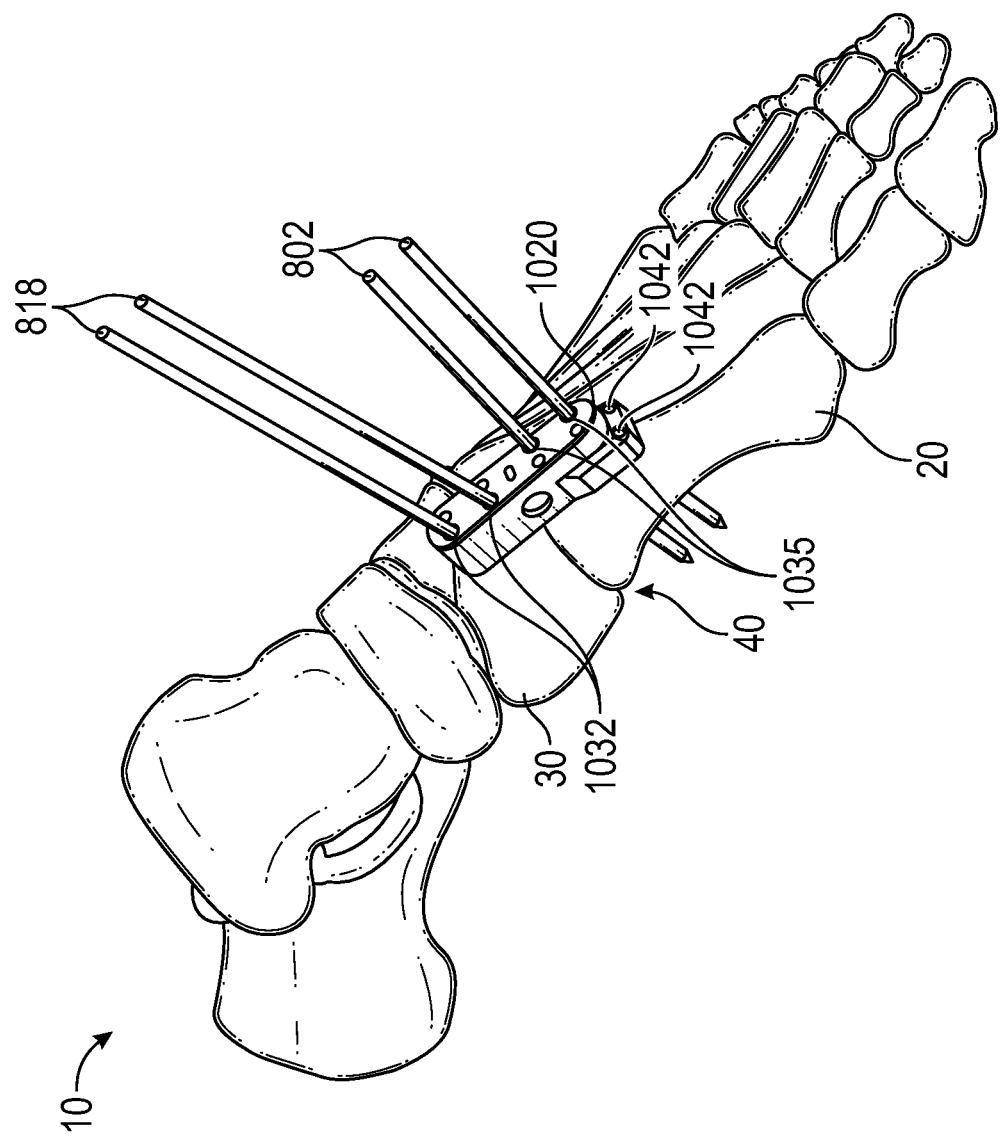
Figure 39:
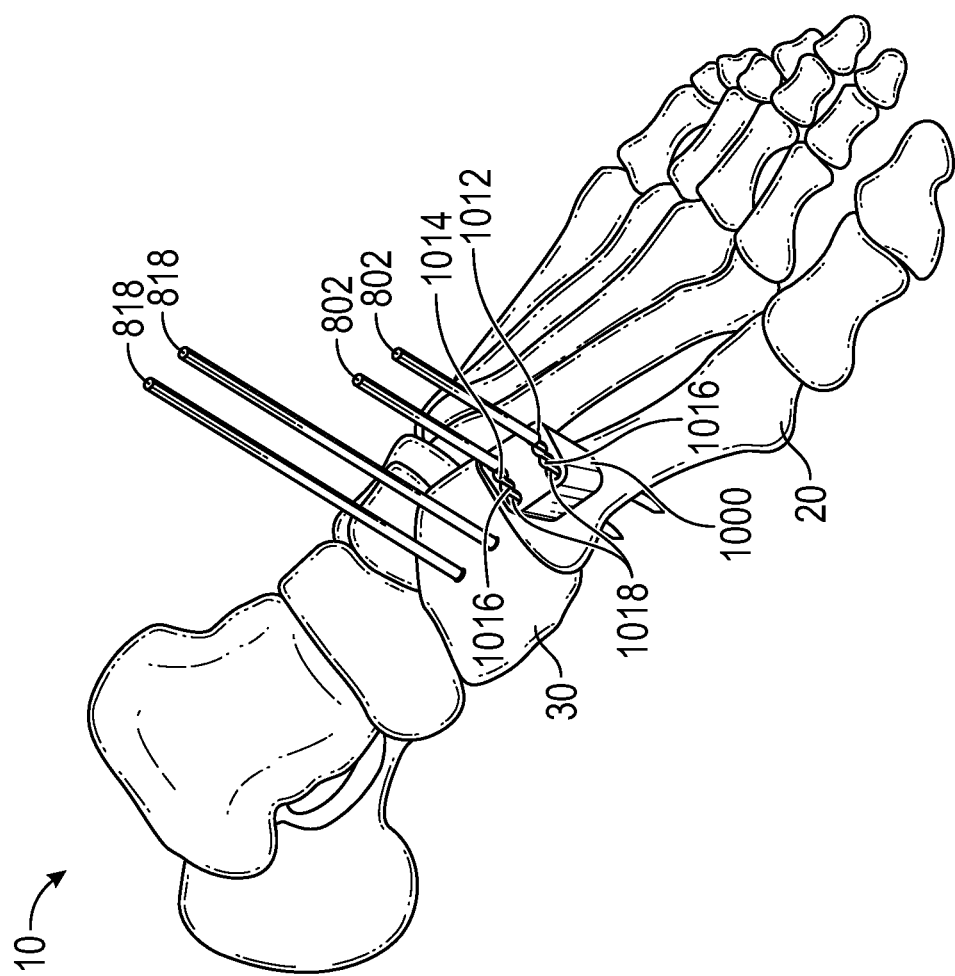
FIGS. 39-48 are perspective views of the bones of a foot, sequentially illustrating a frontal plane realignment portion of an example Lapidus bunionectomy procedure using the example bunionectomy devices disclosed herein.

FIGS. 36-38 are perspective views of the bones of a foot 10, sequentially illustrating a frontal plane realignment portion of an example Lapidus bunionectomy procedure using the realignment guide 1020 illustrated in FIGS. 32A-32C. The frontal plane realignment portion of the Lapidus bunionectomy illustrated in FIGS. 36-38 may be performed at any time after the first metatarsal 20 and the first cuneiform 30 have been cut, and prior to fixation, as described elsewhere herein. As the realignment guide 1020 is configured as both a pin guide and a compression block for frontal plane realignment, the realignment portion illustrated in FIGS. 36-38 may be performed instead of or in addition to (e.g., before or after) the compression portion of the Lapidus bunionectomy as illustrated in FIGS. 16-18. For example, in some procedures, a surgeon may perform an initial frontal plane correction and may subsequently determine, such as when initially fitting the compression block as shown in in FIG. 16, that further correction or realignment of the first metatarsal 20 in the frontal plane is needed.

The frontal plane realignment begins with the foot 100 in a configuration as illustrated in FIG. 15 or 33 described above, in which metatarsal pins 802 remain in the first metatarsal 20 and cuneiform pins 818 remain in the first cuneiform 30 following cutting of the bones using the cut guides described herein. The realignment portion continues to the configuration shown in FIG. 36, as the realignment guide 1020 is placed by inserting the metatarsal pins 802 through a first pair of distal pin holes 1035 and inserting the cuneiform pins 818 through a first pair of proximal pin holes 1030. When the metatarsal pins 802 and the cuneiform pins 818 are disposed within pairs of holes on the same side of the realignment guide 1020 as shown in FIG. 36, the realignment guide 1020 functions similarly to the compression block 400, compressing the cut ends of the first metatarsal 20 and the first cuneiform 30 without applying any frontal plane realignment. At the stage illustrated in FIG. 36, the surgeon may determine that the initial frontal plane adjustment was insufficient, and that the first metatarsal 20 should be realigned by further clockwise rotation to reach a desired alignment.

As shown in FIGS. 37 and 38, the realignment guide 1020 is removed from the foot 10 (FIG. 37) and replaced over the cuneiform pins 818 and metatarsal pins 802. However, in replacing the realignment guide 1020, the cuneiform pins 818 are inserted through the second pair of proximal pin holes 1032, which are angularly displaced relative to the first pair of proximal pin holes 1030. The metatarsal pins 802 are inserted through the same first pair of distal pin holes 1035 through which they were previously inserted in FIG. 36. Thus, the replacement of the realignment guide 1020 effects a further clockwise rotational adjustment of the first metatarsal 20 and compresses the TMT joint 40 for fixation. Alternatively, a counterclockwise adjustment may be performed by reinserting the cuneiform pins 818 through the same first pair of proximal pin holes 1030 and inserting the metatarsal pins 802 through the second set of distal pin holes 1037. Following realignment as shown in FIGS. 36-38, the Lapidus bunionectomy procedure can proceed to fixation of the bones of the TMT joint 40, for example, as shown and described with reference to FIGS. 17-24. The cross pin 824 for temporary fixation, as shown in FIGS. 18-20, can be inserted through either of the cross pin holes 1042.

FIGS. 39-48 are perspective views of the bones of a foot, sequentially illustrating a frontal plane realignment portion of an example Lapidus bunionectomy procedure using the realignment guide 1000 illustrated in FIGS. 31A-31C. The frontal plane realignment portion of the Lapidus bunionectomy illustrated in FIGS. 39-48 may be performed at various stages of the procedure, for example, prior to placement of the compression block as illustrated in FIG. 16. In some embodiments, the frontal plane realignment portion of the Lapidus bunionectomy illustrated in FIGS. 39-48 may be performed after an initial placement of the compression block 400 indicates that more or less frontal plane correction is needed prior to fixation. As will be described in greater detail, realignment using the realignment guide 1000 differs from realignment using the realignment guide 1020 (e.g., FIGS. 36-38) in that the realignment guide 1000 guides the placement of a second pair of metatarsal pins, rotationally displaced relative to the initial pair of metatarsal pins, which may then be used in combination with the compression block 400 to complete the frontal plane realignment.

The frontal plane realignment begins with the foot 100 in a configuration as illustrated in FIG. 15 or 33 described above, in which metatarsal pins 802 remain in the first metatarsal 20 and cuneiform pins 818 remain in the first cuneiform 30 following cutting of the bones using the cut guides described herein. The realignment portion continues to the configuration shown in FIG. 39, as the realignment guide 1000 is placed by inserting the metatarsal pins 802 through a first pair of pin holes 1012 of the realignment guide 1000. In this configuration, the other three pairs of pin holes 1014, 1016, 1018 define pin placement locations for three increasing amounts of clockwise frontal plane realignment. Alternatively, if counterclockwise frontal plane realignment is desired, the realignment guide 1000 would be placed by inserting the metatarsal pins 802 through the fourth pair of pin holes 1018 such that the other three pairs of pin holes 1012, 1014, 1016 would define pine placement locations for counterclockwise frontal plane realignment.

Figure 40:
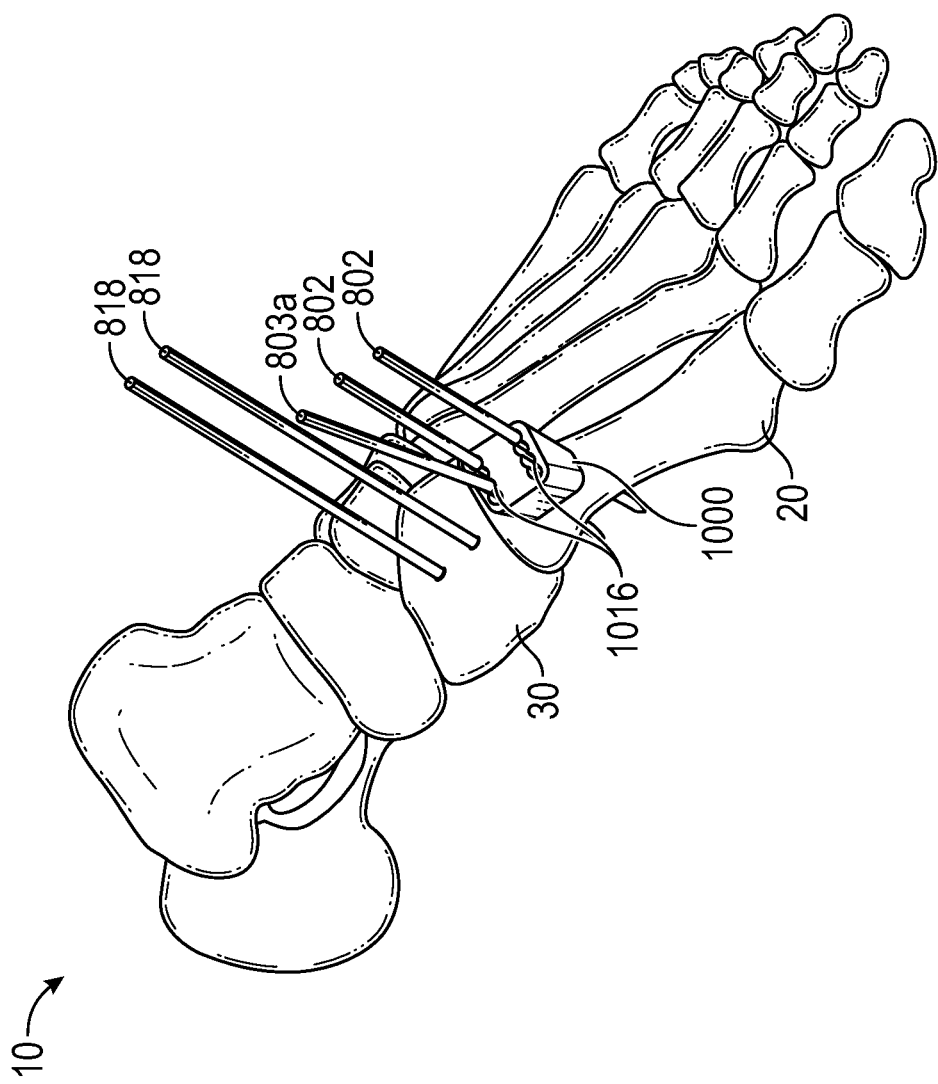

After the realignment guide 1000 is placed, the process continues to FIG. 40 as a first substitute metatarsal pin 803a is partially inserted into the first metatarsal 20 through one of the pair of pin holes 1016. Due to the convergence of the paths of the pin holes 1012, 1014, 1016, 1018 within the first metatarsal 20, it may be impossible or undesirable to fully insert substitute metatarsal pin while the metatarsal pins 802 remain inserted. Accordingly, the first substitute metatarsal pin 803a may be only partially inserted such that the first substitute metatarsal pin 803a does not impinge upon the corresponding metatarsal pin 802. Preferably, the first substitute metatarsal pin 803a extends sufficiently into the bone so as to retain the position and orientation of the realignment guide 1000 relative to the first metatarsal 802 if one of the metatarsal pins 802 is removed.

Figure 41:
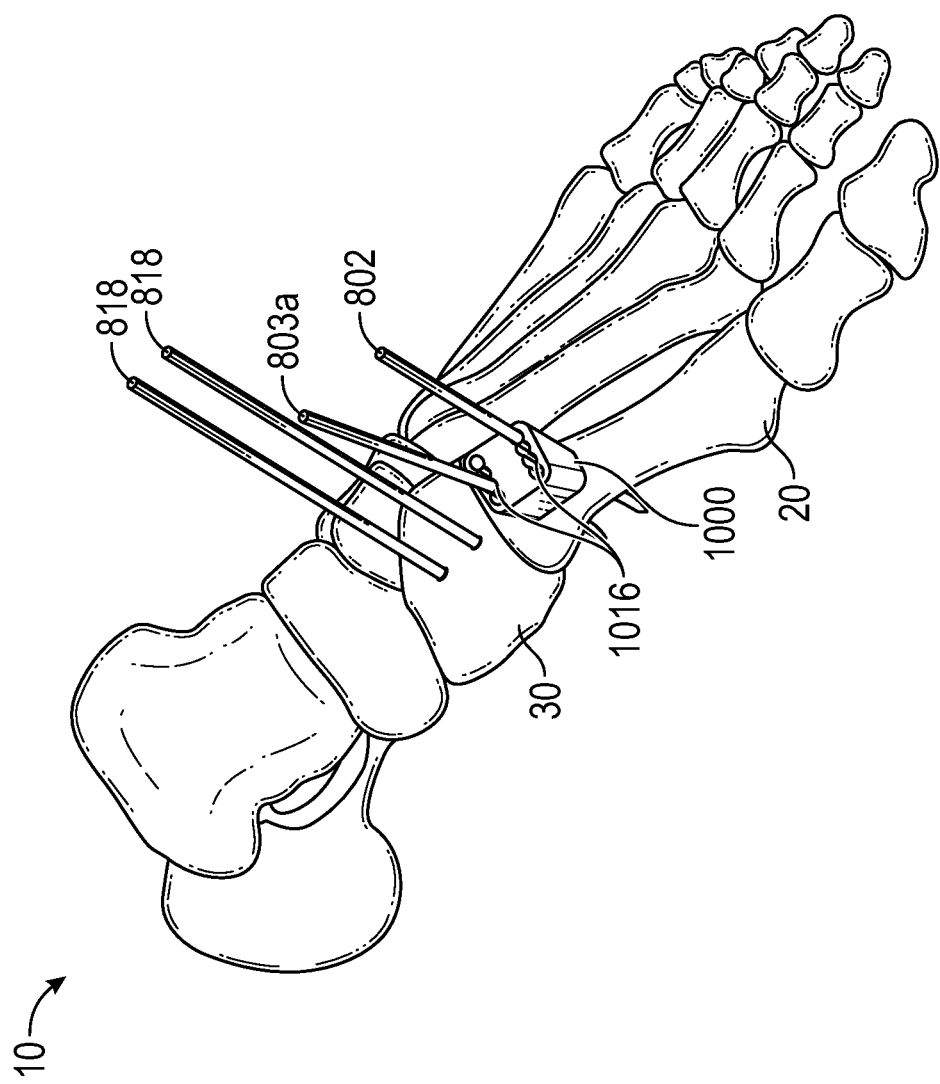
Figure 42:
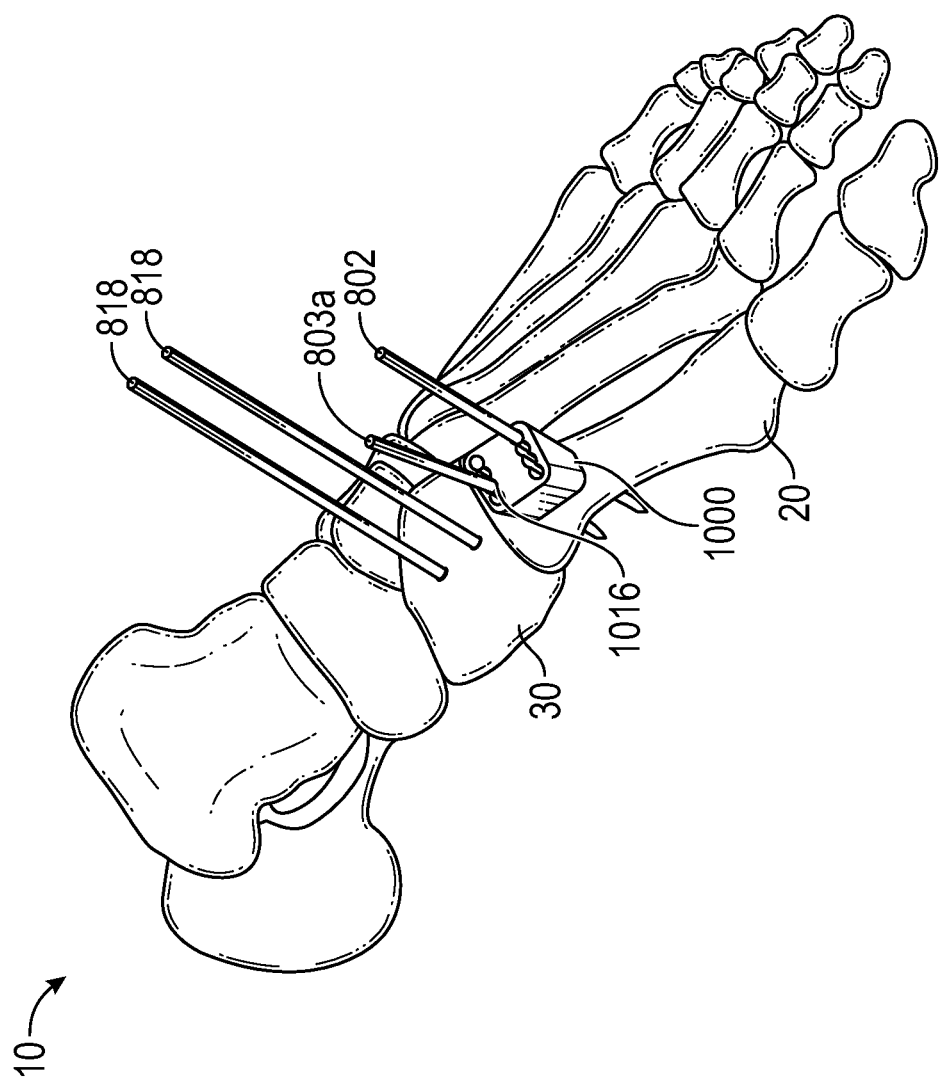

Continuing to FIG. 41, the proximal metatarsal pin 802 corresponding to the first substitute metatarsal pin 803a is removed from the first metatarsal 20. In this configuration, the partially inserted first substitute metatarsal pin 803a and the remaining metatarsal pin 802 are sufficient to maintain the position and orientation of the realignment guide 1000 relative to the first metatarsal. As shown in FIG. 42, the first substitute metatarsal pin 803a can then be inserted further through the pin hole 1016 and the first metatarsal to a fully inserted position, with the realignment guide 1000 serving as a pin placement guide for the first substitute metatarsal pin 803a.

Figure 43:
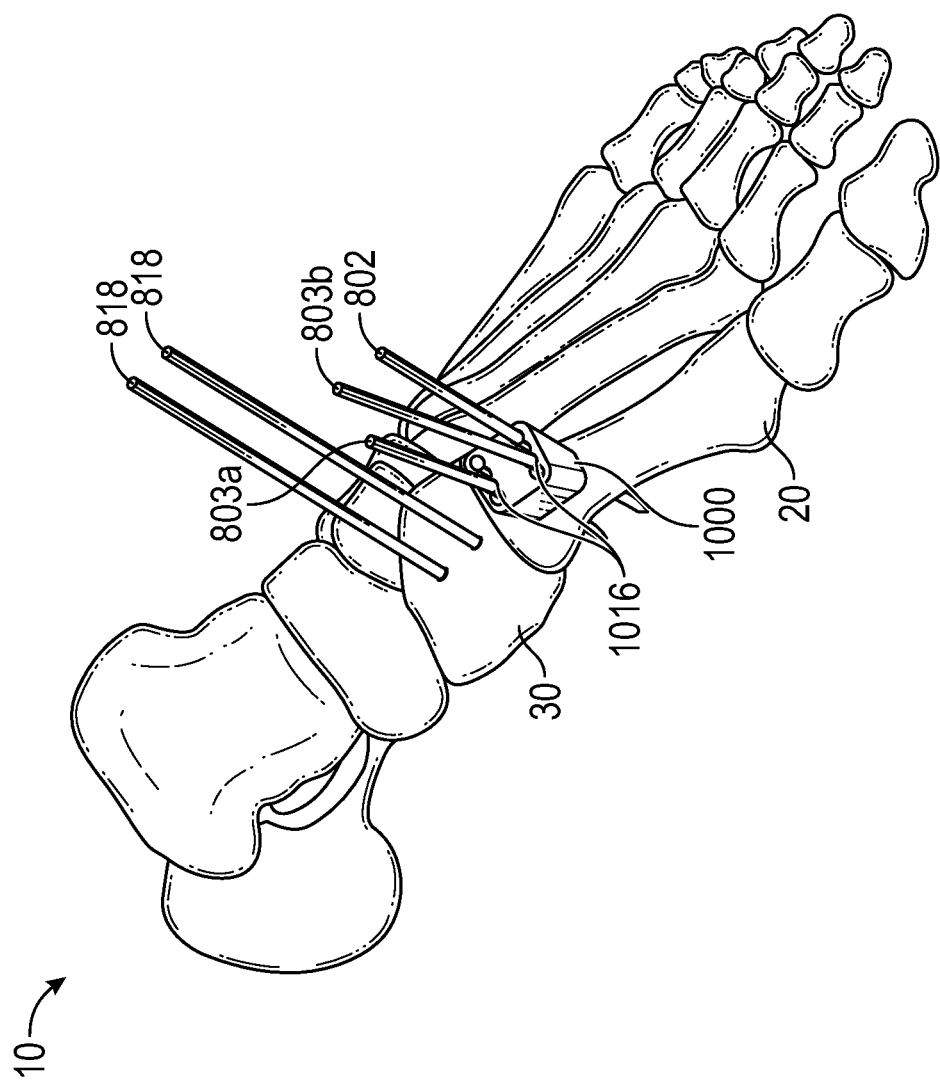
Figure 44:
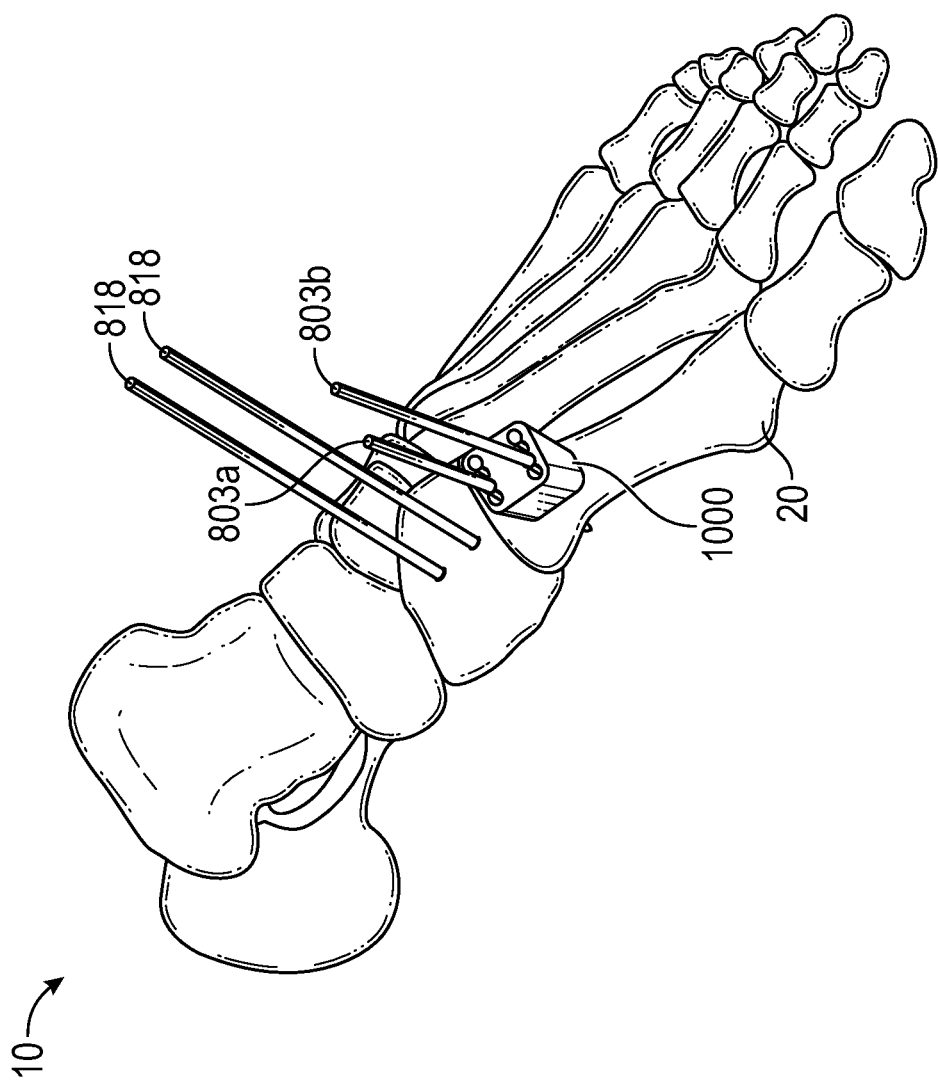
Figure 45:
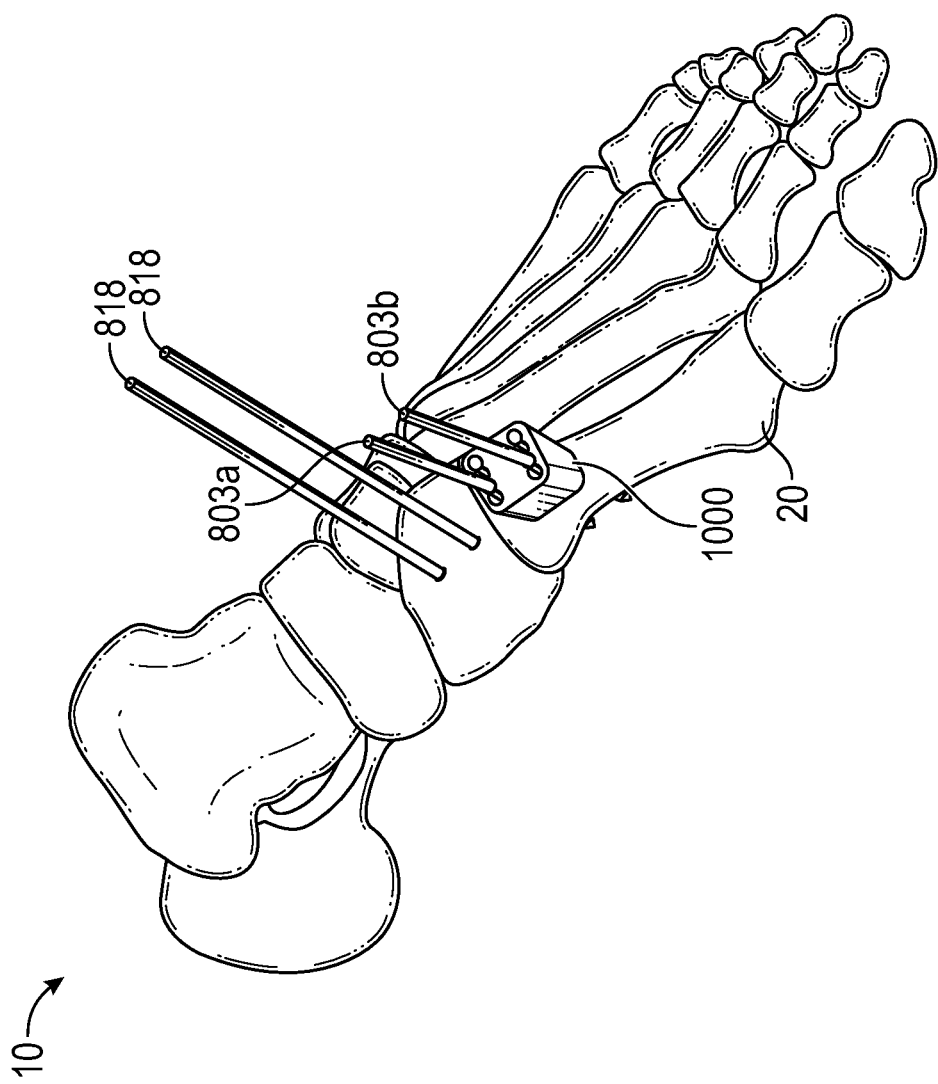

Continuing to FIGS. 43-45, a similar replacement procedure is performed for the remaining metatarsal pin 802. As shown in FIG. 43, a second replacement metatarsal pin 803b is partially inserted through the other pin hole of the pair of pin holes 1016. As shown in FIG. 44, the remaining metatarsal pin 802 is removed to allow the second replacement metatarsal pin 803b to be fully inserted. As shown in FIG. 45, the second replacement metatarsal pin 803b is further inserted through the realignment guide 1000.

Figure 46:
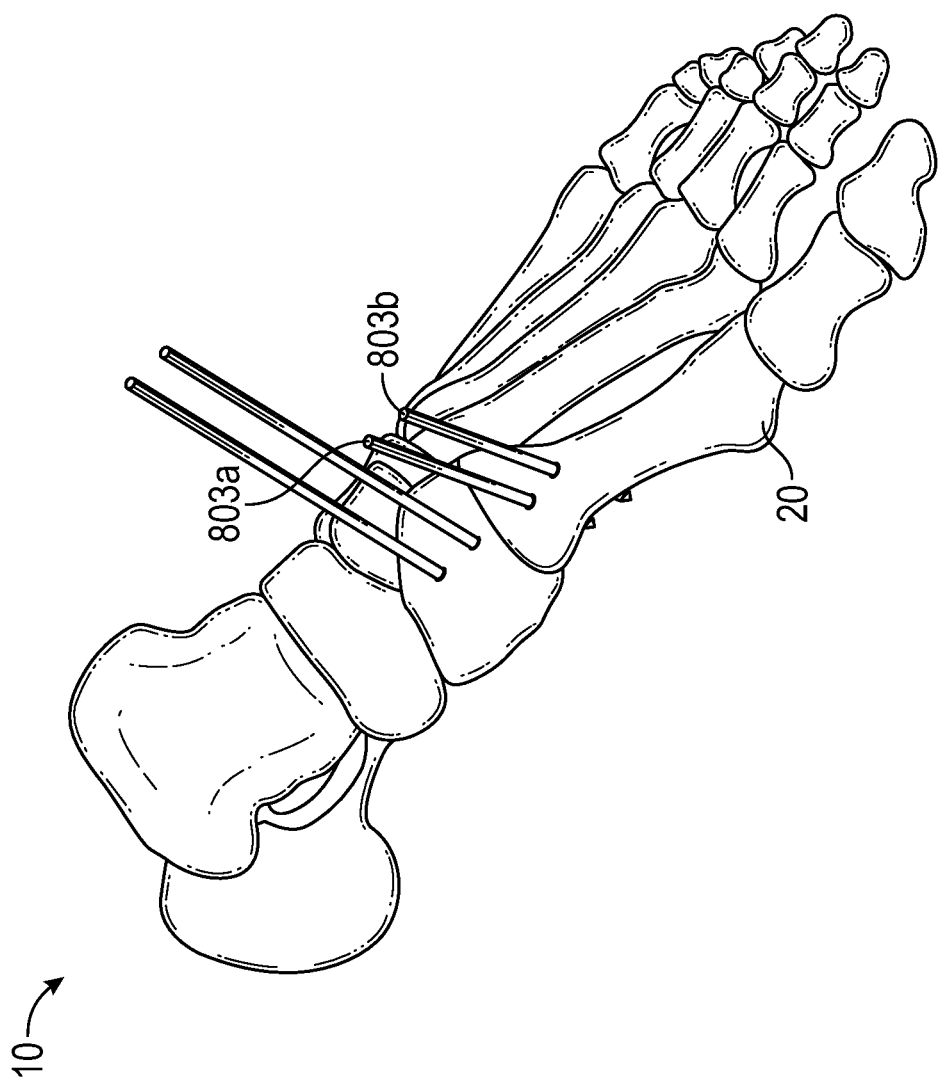
Figure 47:
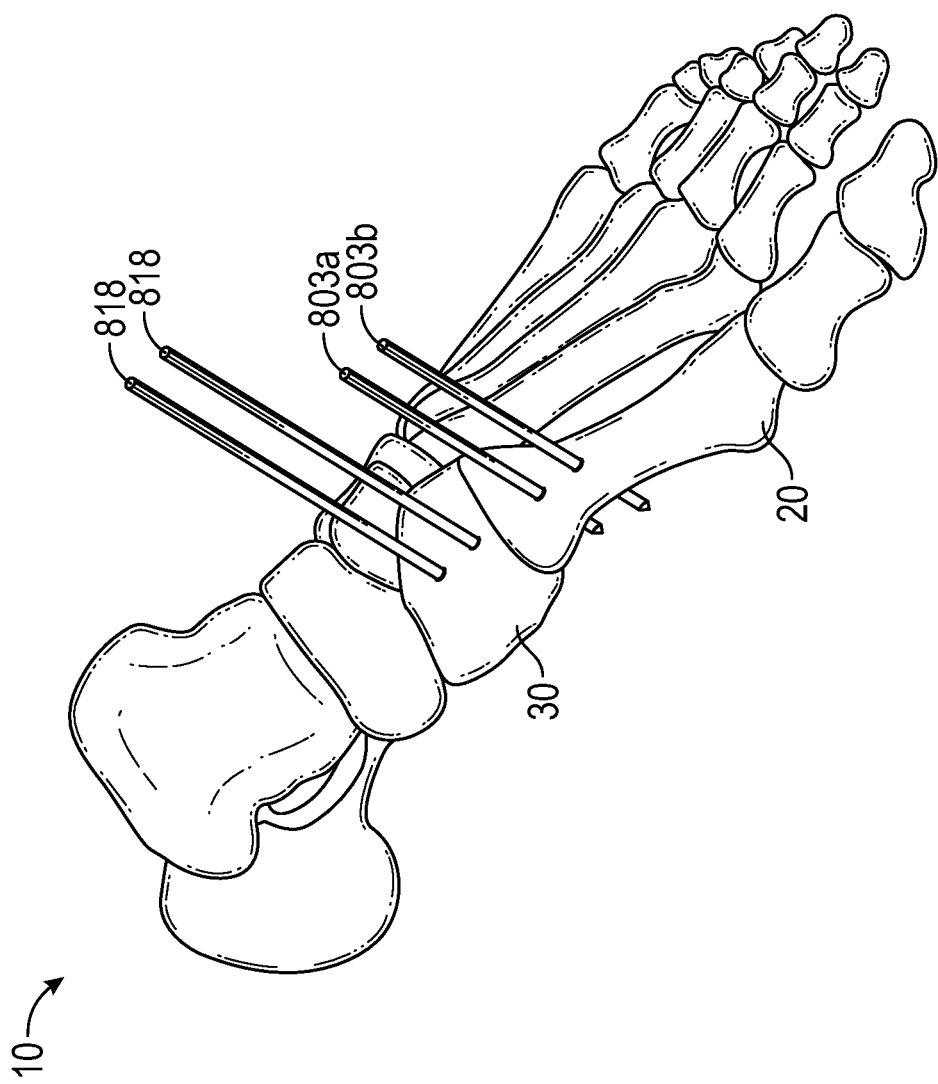
Figure 48:
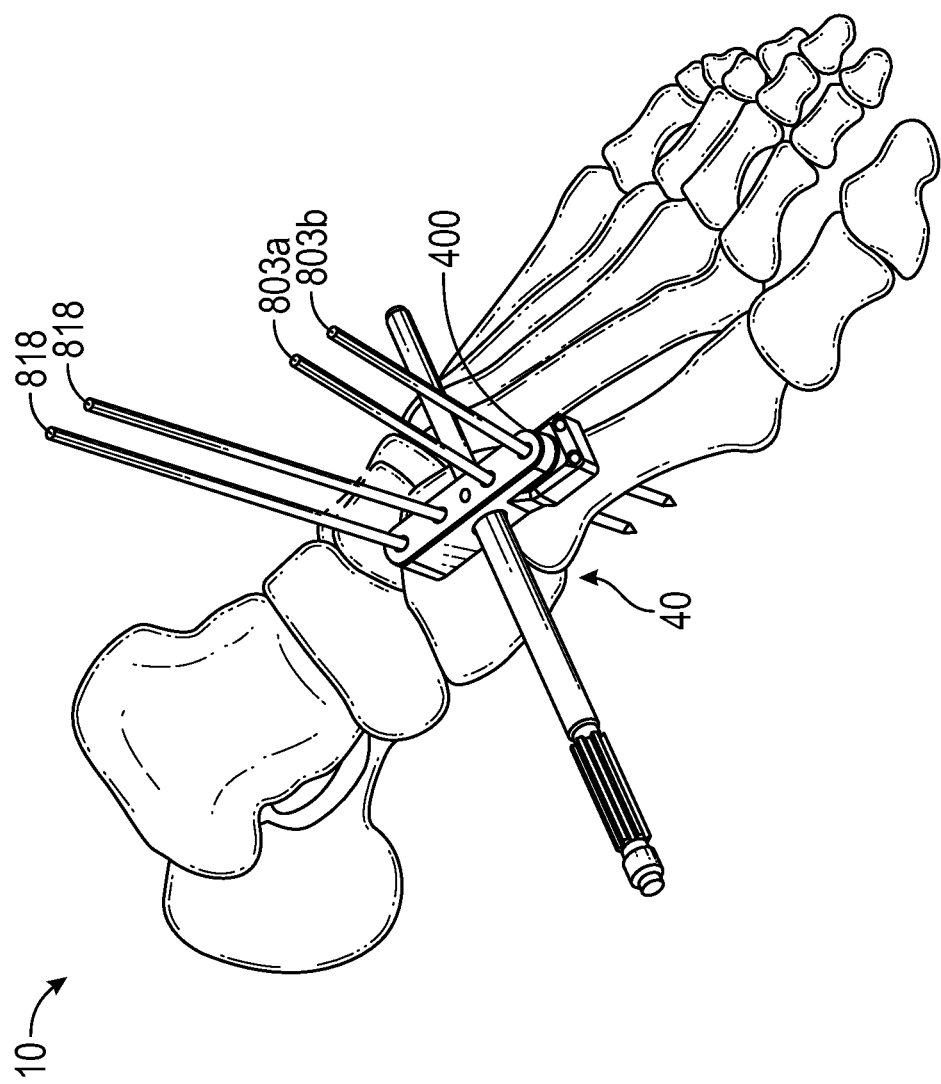

Continuing to FIG. 46, the realignment guide 1000 is removed from the foot 10 such that the replacement metatarsal pins 803a, 803b remain in the first metatarsal 20 with the same spacing but angularly displaced relative to the metatarsal pins 802 that were removed. As shown in FIG. 47, the first metatarsal 20 is then rotated within the frontal plane relative to the first cuneiform 30 into the final orientation in which the replacement metatarsal pins 803a, 803b are aligned with the cuneiform pins 818. Following this final frontal plane realignment process, a compression block such as compression block 400 may then be placed over the cuneiform pins 818 and the replacement metatarsal pins 803a, 803b to compress the TMT joint 40 for fixation. The Lapidus bunionectomy procedure may then proceed to conclusion, for example, as shown and described with reference to FIGS. 17-24.

The embodiments described herein are exemplary. Modifications, rearrangements, substitute processes, etc. may be made to these embodiments and still be encompassed within the teachings set forth herein. Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently rather than sequentially.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements, and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y and/or Z). Thus, such disjunctive language is not generally intended to, and should not, imply that certain embodiments require at least one of X, at least one of Y or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A in conjunction with a second processor configured to carry out recitations B and C.

While the above detailed description has shown, described, and pointed out novel features as applied to illustrative embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

Example Embodiments

1. A method of correcting a bunion, the method comprising:
  inserting a plurality of metatarsal pins into a first metatarsal of a foot at a first predetermined spacing relative to a first tarsometatarsal (TMT) joint;
  excising the first TMT joint of the foot, the excising comprising:
    cutting a base of the first metatarsal proximate the first TMT joint; and
    cutting a base of a first cuneiform of the foot proximate the first TMT joint;
  inserting a plurality of cuneiform pins into the first cuneiform at a second predetermined spacing relative to the first TMT joint;
  compressing the first TMT joint using a compressor block such that a cut face of the first metatarsal contacts a cut face of the first cuneiform; and
  fixing the first TMT joint.

2. The method of Example 1, wherein the first TMT joint is fixed using a bone plate and a plurality of bone screws, and wherein at least one of the plurality of bone screws is a cross screw extending at an angle of less than 90 degrees relative to the bone plate 3. The method of Example 2, wherein the cross screw extends through the bone plate, the first metatarsal, and at least a portion of a second metatarsal of the foot or a second cuneiform of the foot.

4. The method of Example 1, further comprising placing a staple through the bone plate such that a first leg of the staple is seated within the first cuneiform and a second leg of the staple is seated within the first metatarsal.

5. The method of Example 4, wherein the bone plate comprises a cross screw aperture shaped to guide placement of the cross screw such that the second leg of the staple does not impede placement of the cross screw.

6. The method of Example 1, wherein the plurality of metatarsal pins are inserted prior to excising the first TMT joint.

7. The method of Example 1, wherein the plurality of cuneiform pins are inserted prior to cutting the base of the first cuneiform.

8. The method of Example 1, further comprising placing a cut guide across a dorsal side of the first TMT joint prior to inserting the plurality of metatarsal pins and the plurality of cuneiform pins, the cut guide comprising:
 a body;
 a plurality of proximal pin holes extending parallel through the body;
 a plurality of distal pin holes extending through the body parallel to the proximal pin holes; and
 a joint-seeking paddle extending downward from the body between the proximal pin holes and the distal pin holes such that, when the joint-seeking paddle is at least partially disposed within the first TMT joint, the distal pin holes define the first predetermined spacing relative to the first TMT joint and the proximal pin holes define the second predetermined spacing relative to the first TMT joint.

9. The method of Example 8, wherein the cut guide further comprises a proximal slot extending through the body and a distal slot extending through the body on an opposite side of the joint-seeking paddle relative to the proximal slot, such that the distal slot defines a cutting plane for cutting the base of the first metatarsal and the proximal slot defines a cutting plane for cutting the base of the first cuneiform.

10. The method of Example 1, further comprising, prior to compressing the first TMT joint:
 adjusting an alignment of the first metatarsal within a frontal plane of the foot using a control handle coupled to the plurality of metatarsal pins; and
 adjusting an alignment of the first metatarsal within a transverse plane of the foot using a linear reducer comprising a medial hook disposed on a medial side of the first metatarsal and a lateral hook disposed on a lateral side of a second metatarsal of the foot, the lateral hook having an adjustable spacing relative to the medial hook.

11. The method of Example 10, further comprising inserting a medial hook pin through an aperture of the medial hook and into the first metatarsal to rotationally fix the first metatarsal relative to the medial hook prior to adjusting the alignment of the first metatarsal within the transverse plane.

12. The method of Example 10, wherein at least one of the medial hook and the lateral hook comprises a radiolucent material.

13. The method of Example 10, wherein the control handle comprises a handle portion and an engagement portion, the engagement portion comprising a plurality of pin apertures spaced apart at a same spacing as a distance between the metatarsal pins.

14. The method of Example 13, wherein adjusting the alignment of the first metatarsal within the frontal plane comprises:
 sliding the pin apertures over the metatarsal pins such that the engagement portion is proximate the first metatarsal; and
 rotating the first metatarsal about a longitudinal axis of the first metatarsal by applying torque to the control handle.

15. The method of Example 10, wherein adjusting the alignment of the first metatarsal within the transverse plane comprises reducing the adjustable spacing between the lateral hook and the medial hook to bring a distal end of the first metatarsal closer to the second metatarsal.

16. The method of Example 15, wherein the transverse plane alignment of the first metatarsal is adjusted while the first metatarsal is rotationally fixed relative to the medial hook of the linear reducer.

17. The method of Example 10, wherein the plurality of cuneiform pins are inserted subsequent to adjusting the alignment of the first metatarsal in the frontal plane and the transverse plane.

18. The method of Example 1, wherein the compressor block comprises:
 a body comprising a top surface and a bottom surface;
 a plurality of proximal pin holes extending through the body from the top surface to the bottom surface at a first angle of less than 90 degrees relative to the top surface and the bottom surface; and
 a plurality of distal pin holes extending through the body from the top surface to the bottom surface at the first angle relative to top surface and the bottom surface such that the proximal and distal pin holes are more closely spaced at the bottom surface relative to the top surface.

19. The method of Example 18, wherein compressing the first TMT joint comprises:
 inserting the cuneiform pins into the proximal pin holes at the bottom surface;
 inserting the metatarsal pins into the distal pin holes at the bottom surface; and
 sliding the compressor block along the cuneiform pins and the metatarsal pins toward the first TMT joint.

20. The method of Example 18, wherein the compressor block further comprises at least one cross pin hole extending therethrough, each of the at least one cross pin holes defining a linear path passing diagonally through the first TMT joint when the compressor block is aligned proximate the first TMT joint on the cuneiform pins and the metatarsal pins.

21. The method of Example 20, further comprising, after compressing the first TMT joint:
 inserting a cross pin through the at least one cross pin hole to temporarily fix the first TMT joint;
 removing the cuneiform pins and the metatarsal pins from the foot; and
 removing the compressor block by sliding the compressor block away from the first TMT joint along the cross pin.

22. The method of Example 21, further comprising removing the cross pin after at least partially fixing the first TMT joint.

23. The method of Example 1, further comprising placing a reversible cut guide across a dorsal side of the first TMT joint prior to inserting the plurality of metatarsal pins and the plurality of cuneiform pins, the reversible cut guide comprising:
  a body;
  a plurality of first pin holes extending parallel through the body;
  a plurality of second pin holes extending through the body parallel to the proximal pin holes;
  a joint-seeking paddle extending downward from the body between the proximal pin holes and the distal pin holes such that, when the joint-seeking paddle is at least partially disposed within the first TMT joint, the first pin holes define the first predetermined spacing relative to the first TMT joint; and a slot extending through the body parallel to a plane of the joint-seeking paddle such that the slot defines a cutting plane for cutting the base of the first metatarsal or the base of the first cuneiform.

24. The method of Example 23, wherein the base of the first metatarsal and the base of the first cuneiform are cut through the slot, the method further comprising, after cutting the base of the first metatarsal and prior to cutting the base of the first cuneiform:
  removing the reversible cut guide from the first TMT joint; and
  placing the reversible cut guide across the dorsal side of the first TMT joint in a reversed orientation such that the slot defines a cutting plane for cutting the base of the first cuneiform.

25. The method of Example 1, further comprising, prior to fixing the first TMT joint, re-cutting the base of the first metatarsal or the base of the first cuneiform to remove additional tissue.

26. The method of Example 25, wherein the re-cutting is performed using a re-cut guide disposed on the metatarsal pins or the cuneiform pins, the re-cut guide defining a predetermined re-cut spacing smaller than a predetermined spacing defined by a cut guide used for the excising of the first TMT joint.

27. The method of Example 1, further comprising, prior to fixing the first TMT joint, performing a frontal plane realignment comprising additional rotation within the frontal plane of the first metatarsal.

28. The method of Example 27, wherein the frontal plane realignment is performed simultaneously with the compressing of the first TMT joint, and wherein the compressor block is configured as a realignment guide comprising angularly displaced pin holes such that placing the compressor block compresses the first TMT joint and maintains the additional rotation.

29. The method of Example 27, wherein the frontal plane realignment is performed prior to the compressing of the first TMT joint, and wherein the frontal plane realignment comprises:
  inserting, through a realignment guide, a plurality of replacement metatarsal pins at the first predetermined spacing relative to the first TMT joint, the replacement metatarsal pins being angularly displaced relative to the metatarsal pins; and
  aligning the replacement metatarsal pins linearly with the cuneiform pins prior to compressing the first TMT joint.

30. A method of correcting a bunion, the method comprising:
  placing a cut guide across a dorsal side of a first tarsometatarsal (TMT) joint of a foot such that a plurality of first pin holes of the cut guide are disposed proximate a first metatarsal of the foot, a plurality of second pin holes of the cut guide are disposed proximate a first cuneiform of the foot, and a joint-seeking paddle of the cut guide is at least partially disposed within the first TMT joint;
  inserting a plurality of metatarsal pins into the first metatarsal through the first pin holes;
  cutting a base of the first metatarsal proximate the first TMT joint through a slot extending through the cut guide between the first pin holes and the joint-seeking paddle;
  removing the cut guide from the foot;
  replacing the cut guide across the dorsal side of the first TMT joint in a reversed configuration in which the metatarsal pins extend through the second pin holes;
  adjusting an alignment of the first metatarsal within at least one of a frontal plane and a transverse plane of the foot;
  inserting a plurality of cuneiform pins into the first cuneiform through the first pin holes;
  cutting a base of the first cuneiform proximate the first TMT joint through the slot;
  compressing the first TMT joint using a compressor block such that a cut face of the first metatarsal contacts a cut face of the first cuneiform; and
  fixing the first TMT joint.

30. A bunion correction kit comprising:
a cut guide comprising:
  a body;
  a plurality of first pin holes extending parallel through the body and spaced apart at a first distance;
  a plurality of second pin holes extending through the body parallel to the first pin holes, the plurality of second pin holes spaced apart at the first distance;
  a joint-seeking paddle extending from the body between the proximal pin holes and the distal pin holes; and
  a slot extending through the body parallel to the joint-seeking paddle between the joint-seeking paddle and the first pin holes, the slot configured to guide cutting of a base of a first metatarsal or a first cuneiform when the joint-seeking paddle is at least partially disposed within a tarsometatarsal (TMT) joint;
a linear reducer comprising a medial hook and a lateral hook, wherein a spacing between the medial hook and the lateral hook is adjustable to implement a transverse plane correction when the medial hook is seated against a medial side of the first metatarsal and the lateral hook is seated against a lateral side of a second metatarsal;
a control handle comprising a handle portion and an engagement portion, the engagement portion comprising pin apertures spaced apart at the first distance; and
a compressor block comprising:
  a body having a top surface and a bottom surface;
  a plurality of proximal pin holes extending through the body from the top surface to the bottom surface at a first angle of less than 90 degrees relative to the top surface and the bottom surface; and
  a plurality of distal pin holes extending through the body from the top surface to the bottom surface at the first angle relative to the top surface and the bottom surface, wherein the distal pin holes are convergent relative to the proximal pin holes such that the proximal and distal pin holes are more closely spaced at the bottom surface relative to the top surface.

32. The bunion correction kit of Example 31, further comprising a re-cut guide, the re-cut guide comprising:

a body;
a plurality of pin holes extending through the body and spaced apart at the first distance;
a joint-seeking paddle extending from the body; and
a slot extending through the body parallel to the joint-seeking paddle between the joint-seeking paddle and the pin holes, wherein the slot of the re-cut guide is closer to the pin holes of the re-cut guide as compared to a corresponding distance between the slot of the cut guide and the first pin holes of the cut guide.

33. The bunion correction kit of Example 31, wherein the compressor block is configured as a frontal plane realignment guide, at least two of the plurality of proximal pin holes being angularly displaced relative to at least two of the plurality of distal pin holes.

34. The bunion correction kit of Example 31, further comprising one or more bone screws and a bone plate configured to receive the one or more bone screws, wherein the bone plate is configured to receive at least one of the one or more bone screws as a cross screw extending at an angle of less than 90 degrees relative to the bone plate.

35. A linear reducer configured for adjusting a transverse plane alignment of a first metatarsal, the linear reducer comprising:
a shaft having a proximal end and a distal end;
a medial hook coupled to the shaft at the distal end, at least a portion of the medial hook comprising a concave curved surface shaped to seat against a medial side of a first metatarsal;
a lateral hook slidably coupled to the shaft at an intermediate position between the proximal and distal ends, at least a portion of the medial hook comprising a concave curved surface shaped to seat against a lateral side of a second metatarsal while the medial hook is seated against the medial side of the first metatarsal; and
a handle coupled to the shaft adjacent to a proximal side of the lateral hook, the linear position of the handle being adjustable along the shaft to move the lateral hook relative to the medial hook so as to implement a transverse plane correction when the medial hook is seated against a medial side of the first metatarsal and the lateral hook is seated against a lateral side of the second metatarsal.

36. The linear reducer of Example 35, wherein the shaft comprises a threaded exterior surface and wherein the handle comprises a threaded aperture extending therethrough and engaged with the threaded exterior surface of the shaft such that the linear position of the handle is adjustable by twisting the handle about the shaft.

37. The linear reducer of Example 35, wherein the medial hook comprises one or more apertures extending through the concave curved surface so as to accommodate a pin extending therethrough into the first metatarsal.

38. The linear reducer of Example 37, wherein the medial hook is coupled to the shaft by a quick-release coupling movable from a locked position to an unlocked position and wherein, in the unlocked position, the medial hook is slidable along a longitudinal axis of the shaft.

39. The linear reducer of Example 37, wherein at least one of the medial hook and the lateral hook comprises a radiolucent material.

40. The linear reducer of Example 39, wherein the radiolucent material comprises carbon fiber.

41. A cut guide configured to guide cutting of a first metatarsal and a first cuneiform in a bunion correction procedure, the cut guide comprising:

a body comprising a first end and a second end opposite the first end along a longitudinal axis of the cut guide;
a plurality of first pin holes extending parallel through the body proximate the first end, the first pin holes spaced apart along the longitudinal axis at a predetermined spacing;
a plurality of second pin holes extending through the body proximate the second end and parallel to the first pin holes, the second pin holes spaced apart along the longitudinal axis at the predetermined spacing;
a cutting slot extending through the body perpendicular to the longitudinal axis at a first intermediate location between the first pin holes and the second pin holes, the cutting slot sized and shaped to guide cutting of a bone by a sawblade inserted therethrough; and
a joint-seeking paddle extending from a bone-facing surface of the body perpendicular to the longitudinal axis at a second intermediate location between the cutting slot and the second pin holes such that the cut guide can be placed across a first tarsometatarsal (TMT) joint with the joint-seeking paddle seated within the first TMT joint in either a metatarsal cutting orientation in which the cutting slot guides cutting a base of the first metatarsal or a cuneiform cutting orientation in which the cutting slot guides cutting a base of the first cuneiform.

42. The cut guide of Example 41, further comprising one or more longitudinal apertures extending through the body perpendicular to and intersecting the cutting slot.

43. The cut guide of Example 41, wherein the cut guide does not include a second cutting slot.

44. The cut guide of Example 41, further comprising one or more convergent pin holes extending through the body at locations laterally displaced relative to the longitudinal axis, wherein each convergent pin hole meets the bone-facing surface at a first distance from the longitudinal axis and meets an upper surface of the body opposite the bone-facing surface at a second distance from the longitudinal axis, the second distance being greater than the first distance.

45. The cut guide of Example 41, wherein the cutting slot comprises an intermediate section having a first width and terminal sections at opposite ends of the intermediate section, the terminal sections having a second width greater than the first width.

What is claimed is:

1. A method of correcting a bunion, the method comprising:
inserting a plurality of metatarsal pins into a first metatarsal of a foot at a first predetermined spacing relative to a first tarsometatarsal (TMT) joint;
excising the first TMT joint of the foot, the excising comprising:
cutting a base of the first metatarsal proximate the first TMT joint; and
cutting a base of a first cuneiform of the foot proximate the first TMT joint;
inserting a plurality of cuneiform pins into the first cuneiform at a second predetermined spacing relative to the first TMT joint;
compressing the first TMT joint using a compressor block such that a cut face of the first metatarsal contacts a cut face of the first cuneiform; and
fixing the first TMT joint, wherein the first TMT joint is fixed using a bone plate and a plurality of bone screws, and wherein at least one of the plurality of bone screws is a cross screw extending at an angle of less than 90 degrees relative to the bone plate.

2. The method of claim 1, wherein the cross screw extends through the bone plate, the first metatarsal, and at least a portion of a second metatarsal of the foot or a second cuneiform of the foot.

3. The method of claim 1, further comprising placing a staple through the bone plate such that a first leg of the staple is seated within the first cuneiform and a second leg of the staple is seated within the first metatarsal.

4. The method of claim 3, wherein the bone plate comprises a cross screw aperture shaped to guide placement of the cross screw such that the second leg of the staple does not impede placement of the cross screw.

5. The method of claim 1, wherein the plurality of metatarsal pins are inserted prior to excising the first TMT joint.

6. The method of claim 1, wherein the plurality of cuneiform pins are inserted prior to cutting the base of the first cuneiform.

7. The method of claim 1, further comprising placing a reversible cut guide across a dorsal side of the first TMT joint prior to inserting the plurality of metatarsal pins and the plurality of cuneiform pins, the reversible cut guide comprising:
   a body;
   a plurality of first pin holes extending parallel through the body;
   a plurality of second pin holes extending through the body parallel to the proximal pin holes;
   a joint-seeking paddle extending downward from the body between the proximal pin holes and the distal pin holes such that, when the joint-seeking paddle is at least partially disposed within the first TMT joint, the first pin holes define the first predetermined spacing relative to the first TMT joint; and
   a slot extending through the body parallel to a plane of the joint-seeking paddle such that the slot defines a cutting plane for cutting the base of the first metatarsal or the base of the first cuneiform.

8. The method of claim 7, wherein the base of the first metatarsal and the base of the first cuneiform are cut through the slot, the method further comprising, after cutting the base of the first metatarsal and prior to cutting the base of the first cuneiform:
   removing the reversible cut guide from the first TMT joint; and
   placing the reversible cut guide across the dorsal side of the first TMT joint in a reversed orientation such that the slot defines a cutting plane for cutting the base of the first cuneiform.

9. The method of claim 1, further comprising, prior to fixing the first TMT joint, re-cutting the base of the first metatarsal or the base of the first cuneiform to remove additional tissue.

10. The method of claim 1, further comprising, prior to fixing the first TMT joint, performing a frontal plane realignment comprising additional rotation within the frontal plane of the first metatarsal.

11. A method of correcting a bunion, the method comprising:
   inserting a plurality of metatarsal pins into a first metatarsal of a foot at a first predetermined spacing relative to a first tarsometatarsal (TMT) joint;
   excising the first TMT joint of the foot, the excising comprising:
   cutting a base of the first metatarsal proximate the first TMT joint; and
   cutting a base of a first cuneiform of the foot proximate the first TMT joint;
   inserting a plurality of cuneiform pins into the first cuneiform at a second predetermined spacing relative to the first TMT joint;
   compressing the first TMT joint using a compressor block such that a cut face of the first metatarsal contacts a cut face of the first cuneiform; and
   fixing the first TMT joint,
   the method further comprising placing a cut guide across a dorsal side of the first TMT joint prior to inserting the plurality of metatarsal pins and the plurality of cuneiform pins, the cut guide comprising:
   a body;
   a plurality of proximal pin holes extending parallel through the body;
   a plurality of distal pin holes extending through the body parallel to the proximal pin holes; and
   a joint-seeking paddle extending downward from the body between the proximal pin holes and the distal pin holes such that, when the joint-seeking paddle is at least partially disposed within the first TMT joint, the distal pin holes define the first predetermined spacing relative to the first TMT joint and the proximal pin holes define the second predetermined spacing relative to the first TMT joint.

12. The method of claim 11, wherein the cut guide further comprises a proximal slot extending through the body and a distal slot extending through the body on an opposite side of the joint-seeking paddle relative to the proximal slot, such that the distal slot defines a cutting plane for cutting the base of the first metatarsal and the proximal slot defines a cutting plane for cutting the base of the first cuneiform.

13. A method of correcting a bunion, the method comprising:
   inserting a plurality of metatarsal pins into a first metatarsal of a foot at a first predetermined spacing relative to a first tarsometatarsal (TMT) joint;
   excising the first TMT joint of the foot, the excising comprising:
   cutting a base of the first metatarsal proximate the first TMT joint; and
   cutting a base of a first cuneiform of the foot proximate the first TMT joint;
   inserting a plurality of cuneiform pins into the first cuneiform at a second predetermined spacing relative to the first TMT joint;
   compressing the first TMT joint using a compressor block such that a cut face of the first metatarsal contacts a cut face of the first cuneiform; and
   fixing the first TMT joint,
   the method further comprising, prior to compressing the first TMT joint:
   adjusting an alignment of the first metatarsal within a frontal plane of the foot using a control handle coupled to the plurality of metatarsal pins; and
   adjusting an alignment of the first metatarsal within a transverse plane of the foot using a linear reducer comprising a medial hook disposed on a medial side of the first metatarsal and a lateral hook disposed on a lateral side of a second metatarsal of the foot, the lateral hook having an adjustable spacing relative to the medial hook.

14. The method of claim 13, further comprising inserting a medial hook pin through an aperture of the medial hook and into the first metatarsal to rotationally fix the first metatarsal relative to the medial hook prior to adjusting the alignment of the first metatarsal within the transverse plane.

15. The method of claim 13, wherein at least one of the medial hook and the lateral hook comprises a radiolucent material.

16. The method of claim 13, wherein the control handle comprises a handle portion and an engagement portion, the engagement portion comprising a plurality of pin apertures spaced apart at a same spacing as a distance between the metatarsal pins.

17. The method of claim 16, wherein adjusting the alignment of the first metatarsal within the frontal plane comprises:
sliding the pin apertures over the metatarsal pins such that the engagement portion is proximate the first metatarsal; and
rotating the first metatarsal about a longitudinal axis of the first metatarsal by applying torque to the control handle.

18. The method of claim 13, wherein adjusting the alignment of the first metatarsal within the transverse plane comprises reducing the adjustable spacing between the lateral hook and the medial hook to bring a distal end of the first metatarsal closer to the second metatarsal.

19. The method of claim 18, wherein the transverse plane alignment of the first metatarsal is adjusted while the first metatarsal is rotationally fixed relative to the medial hook of the linear reducer.

20. The method of claim 13, wherein the plurality of cuneiform pins are inserted subsequent to adjusting the alignment of the first metatarsal in the frontal plane and the transverse plane.

21. A method of correcting a bunion, the method comprising:
inserting a plurality of metatarsal pins into a first metatarsal of a foot at a first predetermined spacing relative to a first tarsometatarsal (TMT) joint;
excising the first TMT joint of the foot, the excising comprising:
cutting a base of the first metatarsal proximate the first TMT joint; and
cutting a base of a first cuneiform of the foot proximate the first TMT joint;
inserting a plurality of cuneiform pins into the first cuneiform at a second predetermined spacing relative to the first TMT joint;
compressing the first TMT joint using a compressor block such that a cut face of the first metatarsal contacts a cut face of the first cuneiform; and
fixing the first TMT joint,
wherein the compressor block comprises:
a body comprising a top surface and a bottom surface;
a plurality of proximal pin holes extending through the body from the top surface to the bottom surface at a first angle of less than 90 degrees relative to the top surface and the bottom surface; and
a plurality of distal pin holes extending through the body from the top surface to the bottom surface at the first angle relative to top surface and the bottom surface such that the proximal and distal pin holes are more closely spaced at the bottom surface relative to the top surface.

22. The method of claim 21, wherein compressing the first TMT joint comprises:
inserting the cuneiform pins into the proximal pin holes at the bottom surface;
inserting the metatarsal pins into the distal pin holes at the bottom surface; and
sliding the compressor block along the cuneiform pins and the metatarsal pins toward the first TMT joint.

23. The method of claim 21, wherein the compressor block further comprises at least one cross pin hole extending therethrough, each of the at least one cross pin holes defining a linear path passing diagonally through the first TMT joint when the compressor block is aligned proximate the first TMT joint on the cuneiform pins and the metatarsal pins.

24. The method of claim 23, further comprising, after compressing the first TMT joint:
inserting a cross pin through the at least one cross pin hole to temporarily fix the first TMT joint;
removing the cuneiform pins and the metatarsal pins from the foot; and
removing the compressor block by sliding the compressor block away from the first TMT joint along the cross pin.

25. The method of claim 24, further comprising removing the cross pin after at least partially fixing the first TMT joint.

26. A method of correcting a bunion, the method comprising:
inserting a plurality of metatarsal pins into a first metatarsal of a foot at a first predetermined spacing relative to a first tarsometatarsal (TMT) joint;
excising the first TMT joint of the foot, the excising comprising:
cutting a base of the first metatarsal proximate the first TMT joint; and
cutting a base of a first cuneiform of the foot proximate the first TMT joint;
inserting a plurality of cuneiform pins into the first cuneiform at a second predetermined spacing relative to the first TMT joint;
compressing the first TMT joint using a compressor block such that a cut face of the first metatarsal contacts a cut face of the first cuneiform;
re-cutting the base of the first metatarsal or the base of the first cuneiform to remove additional tissue; and
fixing the first TMT joint subsequent to the re-cutting,
wherein the re-cutting is performed using a re-cut guide disposed on the metatarsal pins or the cuneiform pins, the re-cut guide defining a predetermined re-cut spacing smaller than a predetermined spacing defined by a cut guide used for the excising of the first TMT joint.

27. A method of correcting a bunion, the method comprising:
inserting a plurality of metatarsal pins into a first metatarsal of a foot at a first predetermined spacing relative to a first tarsometatarsal (TMT) joint;
excising the first TMT joint of the foot, the excising comprising:
cutting a base of the first metatarsal proximate the first TMT joint; and
cutting a base of a first cuneiform of the foot proximate the first TMT joint;
inserting a plurality of cuneiform pins into the first cuneiform at a second predetermined spacing relative to the first TMT joint;
compressing the first TMT joint using a compressor block such that a cut face of the first metatarsal contacts a cut face of the first cuneiform;
performing a frontal plane realignment comprising additional rotation within the frontal plane of the metatarsal; and
fixing the first TMT joint subsequent the frontal plane realignment, wherein the frontal plane realignment is performed simultaneously with the compressing of the first TMT joint, and wherein the compressor block is configured as a realignment guide comprising angularly displaced pin holes such that placing the compressor block compresses the first TMT joint and maintains the additional rotation.

28. A method of correcting a bunion, the method comprising:
inserting a plurality of metatarsal pins into a first metatarsal of a foot at a first predetermined spacing relative to a first tarsometatarsal (TMT) joint;
excising the first TMT joint of the foot, the excising comprising:
cutting a base of the first metatarsal proximate the first TMT joint; and
cutting a base of a first cuneiform of the foot proximate the first TMT joint;
inserting a plurality of cuneiform pins into the first cuneiform at a second predetermined spacing relative to the first TMT joint;
compressing the first TMT joint using a compressor block such that a cut face of the first metatarsal contacts a cut face of the first cuneiform;
performing a frontal plane realignment comprising additional rotation within the frontal plane of the metatarsal; and
fixing the first TMT joint subsequent the frontal plane realignment,
wherein the frontal plane realignment is performed prior to the compressing of the first TMT joint, and wherein the frontal plane realignment comprises:
inserting, through a realignment guide, a plurality of replacement metatarsal pins at the first predetermined spacing relative to the first TMT joint, the replacement metatarsal pins being angularly displaced relative to the metatarsal pins; and
aligning the replacement metatarsal pins linearly with the cuneiform pins prior to compressing the first TMT joint.

29. A method of correcting a bunion, the method comprising:
placing a cut guide across a dorsal side of a first tarsometatarsal (TMT) joint of a foot such that a plurality of first pin holes of the cut guide are disposed proximate a first metatarsal of the foot, a plurality of second pin holes of the cut guide are disposed proximate a first cuneiform of the foot, and a joint-seeking paddle of the cut guide is at least partially disposed within the first TMT joint;
inserting a plurality of metatarsal pins into the first metatarsal through the first pin holes;
cutting a base of the first metatarsal proximate the first TMT joint through a slot extending through the cut guide between the first pin holes and the joint-seeking paddle;
removing the cut guide from the foot;
replacing the cut guide across the dorsal side of the first TMT joint in a reversed configuration in which the metatarsal pins extend through the second pin holes;
adjusting an alignment of the first metatarsal within at least one of a frontal plane and a transverse plane of the foot;
inserting a plurality of cuneiform pins into the first cuneiform through the first pin holes;
cutting a base of the first cuneiform proximate the first TMT joint through the slot;
compressing the first TMT joint using a compressor block such that a cut face of the first metatarsal contacts a cut face of the first cuneiform; and
fixing the first TMT joint.

* * * * *